US007481997B1

(12) United States Patent
Hardy

(10) Patent No.: US 7,481,997 B1
(45) Date of Patent: Jan. 27, 2009

(54) SNOW MOUNTAIN VIRUS GENOME SEQUENCE, VIRUS-LIKE PARTICLES AND METHODS OF USE

(75) Inventor: Michele E. Hardy, Bozeman, MT (US)

(73) Assignee: Montana State University, Bozeman, MT (US)

( * ) Notice: Subject to any disclaimer, the term of this patent is extended or adjusted under 35 U.S.C. 154(b) by 121 days.

(21) Appl. No.: 11/058,030

(22) Filed: Feb. 14, 2005

Related U.S. Application Data

(60) Provisional application No. 60/544,386, filed on Feb. 12, 2004.

(51) Int. Cl.
*A61K 35/00* (2006.01)
*A61K 39/395* (2006.01)
*C12N 15/63* (2006.01)

(52) U.S. Cl. ................. 424/93.1; 435/320.1; 435/91.33

(58) Field of Classification Search ....................... None
See application file for complete search history.

(56) References Cited

U.S. PATENT DOCUMENTS

| | | | |
|---|---|---|---|
| 4,469,863 | A | 9/1984 | Ts'o et al. |
| 4,816,567 | A | 3/1989 | Cabilly et al. |
| 5,034,506 | A | 7/1991 | Summerton et al. |
| 5,216,141 | A | 6/1993 | Benner |
| 5,235,033 | A | 8/1993 | Summerton et al. |
| 5,270,184 | A | 12/1993 | Walker et al. |
| 5,292,658 | A | 3/1994 | Cormier et al. |
| 5,386,023 | A | 1/1995 | Sanghvi et al. |
| 5,418,155 | A | 5/1995 | Cormier et al. |
| 5,422,252 | A | 6/1995 | Walker et al. |
| 5,455,166 | A | 10/1995 | Walker |
| 5,470,723 | A | 11/1995 | Walker et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,602,240 | A | 2/1997 | De Mesmaeker et al. |
| 5,625,126 | A | 4/1997 | Lonberg et al. |
| 5,633,425 | A | 5/1997 | Lonberg et al. |
| 5,637,684 | A | 6/1997 | Cook et al. |
| 5,644,048 | A | 7/1997 | Yau |
| 5,654,010 | A | 8/1997 | Johnson et al. |
| 5,661,016 | A | 8/1997 | Lonberg et al. |
| 5,683,888 | A | 11/1997 | Campbell |
| 5,741,668 | A | 4/1998 | Ward et al. |
| 5,777,079 | A | 7/1998 | Tsien et al. |
| 5,804,387 | A | 9/1998 | Cormack et al. |
| 5,854,033 | A | 12/1998 | Lizardi |
| 5,874,304 | A | 2/1999 | Zolotukhin et al. |
| 5,876,995 | A | 3/1999 | Bryan |
| 5,925,558 | A | 7/1999 | Tsien et al. |
| 6,245,892 | B1 | 6/2001 | Oaks et al. |
| 6,277,379 | B1 | 8/2001 | Oaks et al. |
| 6,403,597 | B1 | 6/2002 | Wilson et al. |
| 6,680,374 | B2 | 1/2004 | Oaks et al. |

FOREIGN PATENT DOCUMENTS

| | | | |
|---|---|---|---|
| WO | WO 92/15673 | A1 | 9/1992 |
| WO | WO 95/07463 | A1 | 3/1995 |
| WO | WO 96/07399 | A1 | 3/1996 |
| WO | WO 96/40072 | A2 | 12/1996 |
| WO | WO97/03692 | A1 | 2/1997 |
| WO | WO 98/14605 | A1 | 4/1998 |
| WO | WO 98/26277 | A2 | 6/1998 |
| WO | WO 99/49019 | A2 | 9/1999 |
| WO | WO 01/94638 | A2 | 12/2001 |
| WO | WO 02/94190 | A2 | 11/2002 |

OTHER PUBLICATIONS

Ball J. Virol. 1998, vol. 72, No. 2, pp. 1345-1353.*
Altschul et al., "Gapped BLAST and PSI-BLAST: a new generation of protein database search programs," *Nucleic Acids Res.* 25(17):3389-3402 (1997).
Altschul et al., "Local Alignment Statistics" *Methods in Enzymology* 266:460-480 (1996).
Altschul et al., "Basic Local Alignment Search Tool," *J.Mol.Biol.* 403-410 (1990).
Ando et al. "Comparison of the polymerase region of small round structured virus strains previously classified in three antigenic types by solid-phase immune electron microscopy" *Arch Virol.*, 135(102):217-26 (1994).
Baric et al., "Expression and Self-Assembly of Norwalk Virus Capsid Protein from Venezuelan Equine Encephalitis Virus Replicons," *J. Virol*; 76(6):3023-30 (Mar. 2002).
Benson et al. "GenBank" *Nucleic Acids Research*, vol. 28, No. 1 (2000).
Berge et al. "Pharmaceutical Salts" *J. Pharm. Sci.* 66:1-19 (1977).
Bertolotti-Ciarlet et al., "Structural Requirements for the Assembly of Norwalk Virus-Like Particles," *J. Virol* 76(8):4044-55 (Apr. 2002).
Boerner et al., "Production of Antigen-Specific Human Monoclonal Antibodies from in vitro-primed Human Splenocytes," *J. Immunol.* 147(1):B6-95 (1991).
Boniotti et al., "Identification and Characterization of a 3C-Like Protease from Rabbit Hemorrhagic Disease Virus, a Calicivirus," *J. Virol.* 68(10):6487-95 (Oct. 1994).

(Continued)

*Primary Examiner*—Bruce Campell
*Assistant Examiner*—Bao Qun Li
(74) *Attorney, Agent, or Firm*—Cooley Godward Kronish LLP

(57) ABSTRACT

Snow Mountain Virus (SMV) belongs to the Norovirus genus of the Caliciviridae family. SMV is a genogroup II (GII) reference strain of human enteric caliciviruses associated with epidemic gastroenteritis. The positive sense RNA genome sequence of SMV was determined to be 7,537 nucleotides in length excluding the 3' polyadenylated tract. The genome is organized into three open reading frames. Pairwise sequence alignments showed SMV ORF1 is highly conserved with other GII noroviruses, and most closely related to GII strains Melksham and Hawaii viruses. Comparative sequence analyses showed the SMV is a recombinant norovirus. VP1/NP2 proteins assembled into virus-like particles (VLPs) when expressed in insect cells by a recombinant baculovirus. Characterization of one clone that expressed VP1 but failed to assemble into VLPs, identified histidine residue 91 as important for particle assembly.

29 Claims, 13 Drawing Sheets

OTHER PUBLICATIONS

Brill et al., "Synthesis of Oligodeoxynucleoside Phosphorodithioates via Thioamidites," *J.Am.Chem.Soc.* 111:2321 (1989).
Carlsson et al. "Screening for Genetic Mutations," *Nature* 380:207(1996).
Carter et al., "Humanization of an anti-p185$^{HER2}$ antibody for human cancer therapy," *Proc. Natl. Acad. Sci. USA* 89(10):4285-9 (1992).
Chalfie, et al. "Green Fluorescent Protein as a Marker for Gene Expression," *Science* 263 (5148):802-805 (Feb. 11, 1994).
Clarke et al., "Organization and Expression of Calicivirus Genes," *J. Infect. Dis.* 181 Suppl. 2:S309-16 (2000).
Dedman et al., "Surveillance of small round structured virus (SRSV) infection in England and Wales, 1990-5," *Epidomiol. Infect.* 121(1):139-149 (1998).
Dempcy et al., "Synthesis of a thymidyl pentamer of deoxyribonucleic guanidine and binding studies with DNA homopolynucleotides," *Proc. Natl. Acad. Sci. USA* 92(3):6097(1995).
Dingle et al. "Human enteric *Calicviridae*: the complete genome sequence and expression of virus-like particles from a genetic group II small round structured virus" *J.Gen Virol.* 76(Pt.9):2349-55 (Sep. 1995).
Dolin et al. "Detection by Immune Electron Microscopy of the Snow Mountain Agent of Acute Viral Gastroenterities," *J. Infect Dis.* 146(2):184-9 (Aug. 1982).
Duggal et al., "Genetic recombination of a poliovirus in a cell-free system," *Proc Natl Acad Sci USA* 94(25):13786-91 (Dec. 1997).
Duggal et al., "Genetic Recombination of Poliovirus in Vitro and in Vivo: Temperature-Dependent Alteration of Crossover Sites," *Virology* 25:258(1):30-41 (May 1999).
Dunham et al., "Genomic mapping of a calicivirus VPg," *Arch Virol* 143(12):2421-30 (1998).
Egholm et al., "Peptide Nucleic Acids (PNA). Oligonucleotide Analogues with an Achiral Peptide Backbone," *J.Am.Chem.Soc.* 114:1895 (1992).
Egholm, et al., "PNA hybridizes to complementary oligonucleotides obeying the Watson-Crick hydrogen bonding rules," *Nature* 365:566-568 (1993).
Epub Jan. 3, 2002.
Evan et al., "Isolation of Monoclonal Antibodies Specific for Human c-*myc* Proto-Oncogene Product," *Molecular and Cellular Biology* 5:3610-3616 (1985).
Fankhauser et al., "Molecular Epidemiology of "Norwalk-like Virues" in Outbreaks of Gastroenteritis in the United States," *J. Infect. Dis.* 178(6):1751-1578 (1998).
Feng and Doolittle, "Progressive Sequence Alignment as a Prerequisite to Correct Phylogenetic Trees," *J.Mol. Evol.* 25(4):351-360 (1987).
Field et al., "Purification of *RAS*-Responsive Adenylyl Cyclase Complex from *Saccharomyces cervisiae* by Use of an Epitope Addition Method," *Mol. Cell. Biol.*, 8:2159-2165(1988).
Fishwild et al. "High-avidity human IgGk monoclonal antibodies from a novel strain of minilocus transgenic mice" *Nature Biotechnology* 7:845-51 (1996).
Gao et al. "Unusual conformation of a 3'-thioformacetal linkage in a DNA duplex" *J. Biomolecular NMR* 4(1):17-34 (1994).
Glass et al., "Norwalk Virus Open Reading Frame 3 Encodes a Minor Structural Protein," *J. Virol.* 74(14):6581-91(Jul. 2000).
Green et al., "A Predominant Role for Norwalk-like Viruses as Agents of Epidemic Gastroenteritis in Maryland Nursing homes for the Elderly," *J. Infect Dis.* 185(2):133-46 (Jan. 15, 2002).
Green et al., "Capsid Protein Diversity among Norwalk-like Viruses," *Virus Genes* 20(3):227-36 (2000).
Green et al., "Expression and Self-Assembly of Recombinant Capsid protein from the Antigenically Disticnt Hawaii Human Calicivirus," *J. Clin. Microbiol.* 35(7):1909-14 (Jul. 1997).
Guo et al., "Molecular Characterization of a Porcine Enteric Calicivirus Genetically Related to Sapporo-Like Human Caliciviruses," *J. Virol.* 73(11):9625-31 (Nov. 1999).
Hale et al. "Expression and Self-Assembly of Grimsby Virus: Antigenic Distinction from Norwalk and Mexico Viruses," *Clin Diagn. Lab Immunol.* 6(1):142-5 (Jan. 1999).
Hardy et al. "Specific Proteolytic Cleavage of Recombinant Norwalk Virus Capsid Protein" *Virus Genes* 26(1):71-82, (2003).
Hardy et al. "Human Calicivirus Genogroup II Capsid Sequence Diversity Revealed by Analyses of the Prototype Snow Mountain Agent," *Arch Virol.* 142(7):1469-79 (1997).
Hardy et al., "Specific Proteolytic Cleavage of Recombinant Norwalk Virus Capsid Protein," *J. Virol.* 69(3); 145:1693-8 (Mar. 1995).
Hardy et al., "Substrate specificity of the Norwalk virus 3c-like proteinase," *Virus Res.* 89(1):29-39 (Oct. 2002).
Hardy et al., "Completion of the Norwalk Virus Genome Sequence," *Virus Genes* 12(3):287-90 (1996).
Harrington et al., "Binding of Norwalk Virus-Like Particles to ABH Histo-Blood Group Antigens is Blocked by Antisera from Infected Human Volunteers or Experimentally Vaccinated Mice," *J. Virol.* 76(23):12335-12343 (2002).
Heim, et al., "Engineering green fluorescent protein for improved brightness, longer wavelengths and fluorescent resonance energy transfer," *Curr.Biol.* 6(2):178-182 (1996).
Hest et al., "Efficient introduction of aldene functionality into proteins in vivo," *FEBS Lett.* 428(1-2):68-70 (1998).
Higgins and Sharp, "Fast and Sensitive Multiple Sequence Alignments on a Microcomputer," *CABIOS* 5:151:153 (1989).
Hoogenboom and Winter, "By-passing Immunisation Human Antibodies from Synthetic Repertoires of Germline $V_H$ Gene Segments Rearranged in Vitro," *J Mol. Biol.* 227(2):381-388 (1992).
Hopp et al. *Bio Technology* 6:1204-1210(1988).
Hora et al. *Bio/Technology* 8:755-758 (1990).
Horn et al., "Oligonucleotides with Alternating Anionic and Cationic Phosphoramidate Linkages: Synthesis and Hybridization of Stereo-uniform Isomers," *Tetrahedron Lett.* 37(6):743-746 (1996).
Ichiki et al., "Regulation of the Expression of Human C$\epsilon$ Germline Transcript," *J. Immunol.* 150 (12):5408-5417 (1993).
Jenkins et al., "The Biosynthesis of Carbocyclic Nucleosides," *Chem. Soc. Rev.* 169-176, (1995).
Jiang et al., "Characterization of a novel human calicivirus that may be a naturally occuring recombinant," *Arch Virol* 144(12):2377-87 (1999).
Jiang et al., "Expression and characterization of Sapporo-like human calicivirus capsid proteins in baculovirus," *J. Virol Methods.* 78 (1-2):81-91 (Mar. 1999).
Jiang et al., "Expression, Self-Assembly, and Antigenicity of a Snow Mountain Agent-Like Calicivirus Capsid Protein," *J. Clin Microbiol.* 33(6):1452-5 (Jun. 1995).
Jiang et al., "Sequence and Genomic Organization of Norwalk Virus," *Virology* 195(1):51-61 (Jul. 1993).
Johnson et al., "A month-long effect from a single injection of microencapsulated human growth hormone" *Nat. Med.*, 2:795-799 (1966).
Jones et al., "Replacing the complementary-determining regions in a human antibody with those from a mouse," *Nature* 321:522-525 (1986).
Jung et al. et al. "Hybridization of Alternating Cationic/Anionic Oligonucleotides to RNA Segments" *Nucleoside & Nucleotide* 13:1597 (1994).
Karlin et al., "Applications and statistics for multiple high-scoring segments in molecular sequences," *Proc. Natl. Acad. Sci. USA* 90:5873-5787(1993).
Kiedrowshi et al., *Angew Chem. Intl. English* 30:423 (1991).
King et al., "Sequence Analysis of the Gene Encoding the Capsid Protein of the Snow Mountain Human Calicivisur," *Virus Genes.* 15(1):5-7 (1997).
Kirkegaard et al., "The Mechanism of RNA Recombinant in Poliovirus," *Cell 47*(3):433-43 (Nov. 7, 1986).
Kitamoto, N. et al., "Cross-Reactivity among Several Recombinant Calicivirus Lirus-Like Particles (VLPs) with Monoclonal Antibodies Obtained from Mice Immunized Orally with One Type of VLP," *J. Clin Microbiol.*, 40(7):2459-2465 (2002).
Kohler and Milstein, "Continuous Cultures of Fused Cells Secreting Antibody of Predefined Specificity," *Nature* 256:495-7(1975).
Koopmans et al., "Molecular Epidemiolosy of Human Enteric Caliciviruses in the Netherlands," *J. Infect. Dis.* 181 Suppl. 2:S262-69 (2000).

Kozak, "Possible role of flanking nucleotides in recognition of the AUG initiator codon by eukaryotic ribosomes," *Nucleic Acids Res.* 24;9(20):5233-52 (Oct. 1981).
Lambden et al. "Sequence and Genome Organization of a Human Small Round-Structured (Norwalk-like) Virus" *Science* 22;259(5094):516-9 (Jan. 1993).
Laurent et al., "Recombinant Rabbit Hemorrhagic Disease Virus Capsid Protein Expressed in Baculovirus Self-Assembles into Virus-like Particles and Induces Protection," *J. Virol.* 68(10):6794-8 (Oct. 1994).
Leite et al. "Characterization of Toronto Virus Capsid Protein Expressed in baculovirus," *Arch Virol.* 141(5):865-75 (1996).
Letsinger et al., "Cationic Oligonucleotides," *J. Am. Chem. Soc.* 110:4470 (1988).
Letsinger et al., "Effects of pendant groups at phosphorous on binding properties of d-ApA analogues," *Nucl. Acids. Res.* 14:3487 (1986).
Letsinger, "Phosphoramidate Analogs of Oligonucleotides," *J. Org. Chem.* 35(11):3800 (1970).
Lew et al. "Molecular characterization of Hawaii virus and other Norwalk-like viruses: evidence for genetic polymorphism among human caliciviruses," *J. Infect Dis.* 170(3):535-42 (Sep. 1994).
Liu et al., "Identification of further proteolytytic cleavage sites in the Southampton calicivirus polyprotein by expression of the viral protease in *E. coli," J. Virol.* 80(Pt2):291-6 (Feb. 1999).
Liu et al., "Polyprotein Processing in Southampton Virus: Identification of 3C-Like protease Cleavage Sites by in Vitro Mutagenesis," *J. Virol.* 70(4):2605-10 (Apr. 1996).
Lizardi et al., "Mutation detection and single-molecule counting using isothermal rolling-circle amplification," *Nat. Genetics* 19 (3):225-232 (1998).
Lochridge, V. et al., "Snow Mountain Virus Genome Sequence and Virus-like Particle Assembly," *Virus Genes*, 26(1): 71-82 (2003).
Lonberg and Huszar, "Human antibodies from transgenic mice," *Intern. Rev. Immunol.* 13(1):65-93 (1995).
Lonberg et al., "Antigen-specific human antibodies from mice comprising four distinct genetic modifications," *Nature* 368:856-859 (1994).
Lutz-Freyermuth et al., "Quantitative determination that one of two potential RNA-binding domains of the A protein component of the U1 small nuclear ribonucleoprotein complex binds with high affinity to stem-loop II of U1 RNA," *Proc. Natl. Acad. Sci. USA* 87:6393-6397 (1990).
Mag et al., "Sythesis and selective cleavage of an oligodeoxynucleotide containing a bridged internucleotide 5'-phosphorothioate linkage," *Nucleic Acids Res.* 19:1437 (1991).
Marin et al., "ATP Binding and ATPase Activities Associated with Recombinant Rabbit Hemorrhagic Disease Virus 2C-Like Polypeptide," *J. Virol.* 74(22):10846-51 (Nov. 2000).
Marks et al. "By-passing immunization: building high affinity human antibodies by chain shuffling," *Biotechnology* 10:779-783 (1992).
Marks et al., "By-Passing Immunization: Human Antibodies from V-gene Libraries Displayed on Phage," *J. Mol. Biol.* 222(3):581 (1991).
Martin et al., "GAP Domains Responsible for Ras p21-Dependnatn Inhibition of Muscarinic Atrial K+ Channel Currents," *Science* 255:192-194 (1992).
Mathews et al. "Expanded Sequence Dependence of Thermodynamic Parameters Improves Prediction of RNA Secondary Structure" *J.Mol. Biol.* 21;288(5):911-40 (May 1999).
Meier et al. "Peptide Nucleic Acids (PNAs)—Unusual Properties of Noniomic Oligonucleotide Analogues," *Chem. Int. Ed. Eng.* 31:1008-10 (1992).
Mendez et al., "A comparative analysis of Freon substitutes in the purification of reovirus and calicivirus," *J. Virol Methods* 90(1):59-67 (Oct. 2000).
Mesmaeker et al., "Comparison of Rigid and Flexible Backbones in Antisense Oligonucleotides," *Bioorganic & Medicinal Chem. Lett.* 4:395 (1994).
Morens et al. "A waterbone outbreak of gastroenteritis with secondary person-to-person spread. Association with a viral agent," *Lancet* 1(8123):964-6 (May 5, 1979).
Morrison, "Success in Specification," *Nature* 368:812-13 (1994).
Nadeau et al., "Real-Time, Sequence-Specific Detection of Nucleic Acids during Strand Displacement Amplification," *Anal. Biochem* 276(2):177-187 (1999).
Nagy et al., "Dissecting RNA recombinant in vitro: role of RNA sequences and the viral replicase," *EMBO J.* 17(8):2392-403 (Apr. 15, 1998).
Nagy et al., "In Vitro Characterization of Late Step of RNA Recombination in Turnip Crinkle Virus," *Virology* 249(2):393-405 (Sep. 30, 1998).
Nagy et al., "In Vitro Characterization of Late Steps of RNA Recombinant in Turnip Crinkle Virus," *Virology* 249(2):379-92 (Sep. 30, 1998).
Nagy et al., "New Insights into the Mechanisms of RNA Recombination," *Virology* 235(1):1-9 (Aug. 18, 1997).
Nagy et al., "RNA elements required for RNA recombinant function as replication enhancers in vitro and in vivo in a plus-strand RNA virus," *EMBO J.* 18(20):5653-65 (Oct. 15, 1999).
Needleman & Wunsch, "A General Method Applicable to the Search for Similarities in the Amino Acid Sequence of Two Proteins," *J. Mol. Biol.* 48(3):433-453 (1970).
Neill, "Nucleotide sequence of the capsid protein gene of two serotypes of San Miguel sea lion virus: Identification of conserved and non-conserved amino acid sequences among calicivirus capsid proteins," *Virus Res* 24(2):211-22 (Jul. 1992).
Neuberger "Generating high-avidity human Mabs in Mice" *Nature Biotechnology* 14:826 (1996).
Noel et al., "Identification of a Distinct Common Strain of 'Norwalk-like Viruses' Having a Global Distribution," *J. Infect. Dis.* 179(6):1334-1344 (1999).
Nolan et al., "Fluorescence-activates cell analysis and sorting of viable mammalian cells based on β-D-galactosidase activity after transduction of *Escherichia coli lacZ," Proc. Natl. Acad. Sci USA* 85(8):2603-2607 (Apr. 1988).
O'Connor et al., "Humanization of an antibody against human protein C and calcium-dependance involving framework residues," *Protein Eng.* 11:321-8 (1998).
Oggioni et al. "Protocol for Real-Time PCR Identification of Anthrax Spores from Nasal Swabs after Broth Enrichment" *J. Clinical Microbiol.*, 3956-3963 (Nov. 2002).
Paborsky et al. "Mammalian cell transient expression of tissue factor for the production of antigen" *Protein Engineering* 3(6):547-553 (1990).
Pauwels et al. "Biological Activity of New 2-5A Analogues" *Chemica Scripta* 26:1419 (1986).
Pearson and Lipman, Improved tools for biological sequence *Proc. Natl. Acad. Sci. USA* 85:2444 (1988).
Pfister et al., "Polypeptide p41 of a Norwalk-Like Virus Is a Nucleic Acid-Independent Nucleoside Triphosphatese," *J. Virol* 75(4):1611-9 (Feb. 2001).
Pletneva et al., "The Genome of Hawaii Virus and its Relationship with other Members of the *Caliciviridae," Virus Genes*. 23(1):5-16 (2001).
Prasad et al. "X-ray Crystallographic Structure of the Norwalk Virus Capsid," *Science* 8;286(5438):287-90 (Oct. 1999).
Presta, "Antibody Engineering" *Curr. Op. Struct. Biol.* 2:593-596 (1992).
Queen et al., "A humanized antibody that binds to the interleukin 2 receptor," *Proc. Natl. Sci. USA* 86:10029-33 (1989).
Riechmann et al., "Reshaping human antibodies for therapy," *Nature* 332:323-329 (1988).
Sawai et al. "Synthesis and Properties of Oligodenylic Acids Containing 2'-5' Phosphoramide Linkage" *Chem. Lett.* 805 (1984).
Schreier et al., "Molecular epidemiology of outbreaks of gastroenteritis associated with small round structured viruses in Germany in 1997/98," *Arch Virol.* 145(3):443-53 (2000).
Seah et al., "Open Reading Frame 1 of the Norwalk-Like Virus Camberwell: Completion of Sequence and Expression in Mammalian Cells," *J. Virol.* 73(12):10531-5 (Dec. 1999).
Seah et al., "Variation in ORF3 of genogroup 2 Norwalk-like viruses," *Arch Virol.* 144(5):1007-14 (1999).
Siepel et al., "A computer program designed to screen rapidly for HIV type 1 intersubtype recombinant sequences," *AIDS Res Hum Retroviruses* 11(11):1412-6 (Nov. 1995).

Simon et al., "Peptoids: A modular approach to drug discovery," *PNAS USA* 89(20):9367 (1992).

Skinner et al., "Use of the Glu-Glu-Phe C-terminal Epitope for Rapid Purification of the Catalytic Domain of Normal and Mutant *ras* GTPase- activating Proteins," *J.Biol.Chem.* 266(22):14163-14166 (1991).

Smith and Waterman, "Comparison of Biosequences," *Adv. Appl. Math.* 2:482 (1981).

Someya et al., "Complete Nucleotide Sequence of the Chiba Virus Genome and Functional Expression of the 3C-Like Protease in *Escherichia coli," Virology* 278(2):490-500 (Dec. 20, 2000).

Sosnovtsev et al., "Cleavage of the Feline Calicivirus Capsid Precursor is Mediated by a Virus-Encoded Proteinase," *J. Virol* 72(4):3051-9 (Apr. 1998).

Sosnovtsev et al., "Identification and Genomic Mapping of the ORF3 and VPg Proteins in Feline Calicivirus Virions," *Virology* 277(1):193-203 (Nov. 10, 2000).

Sprinzl et al., "Enzymatic Incorporation of ATP and CTP Analogues into the 3'End of tRNA," *Eur. J. Biochem* 81(3):579-589 (1977).

Stauber, R.H., "Development and applications of enhanced green fluorescent protein mutants," *Biotechniques* 24(3):462-471 (1998).

Stein, "Overcoming obstacles to monoclonal antibody product development and approval," *Trends in Biotechnol.* 15(3):88-90 (1997).

Tang et al. *Abstr. Pap. Am. Chem.* S218:U138 Part 2 (Aug. 22, 1999).

Thompson et al., "Clustal W: improving the sensitivity of progressive multiple sequence alignment through sequence weighting, position-specific gap penalties and weight matrix choice," *Nucleic Acids Res.* 22(22):4673-80 (1994).

Vazquez et al., "Expression of Enzymatically Active: Rabbit Hemorrhagic Disease Virus RNA-Dependent RNA Polymerase in *Escherichia coli," J. Virol.* 72(4):2999-3004 (Apr. 1998).

Verhoeyen et al. "Reshaping human antibodies: grafting an antilysozyme activity" *Science* 239:1534-1536 (1998).

Vinge et al., "Genetic polymorphism across regions of the three open reading frames of ;Norwalk-like viruses," *Arch Virol.* 145(2):223-41 (2000).

Walker et al., "Isothermal in vitro amplification of DNA by a restriction enzyme/DNA polymerase system," *PNAS* 89:392-396 (1992).

Walker et al., "Strand displacement amplification-an isothermal, in vitro DNA amplification technique," *Nucl. Acids. Res.* 20 (7):1691-1696 (1992).

Wang et. al., "Sequence Diversity of Small, round-Structured Viruses in the Norwalk Virus Goup," *J. Virol.* 68(9):5982-90 (1994).

Wirblich et al., "3C-Like Protese if Rabbit Hemorrhagic Disease Virus: Identification of Cleavage Sites in the ORF1 Polyprotein and Analysis of Cleavage Specificity," *J. Virol* 69(11):7159-68 (1995).

Wirblich et al., "Genetic Map of the Calicivirus Rabbit hemorrhagid Disease Virus as Deduced from in Vitro Translation Studies," *J. Virol.* 70(11):7974-83 (1996).

* cited by examiner

A.

B.

| | | | | | | |
|---|---|---|---|---|---|---|
| SMV | (331) LQGP | (697) LQGP | (876) PEGK | (1009) FEAP | (1190) LEGG | |
| SHV | (400) LGGP | (763) LGGK | (962) MEGK | (1100) FEAP | (1281) LEGG | |
| CV | (331) LQGP | (697) LQGP | (876) TEGK | (1009) FEAP | (1190) LEGG | |
| NV | (399) LQGP | (762) LQGP | (963) PEGK | (1101) FEAP | (1282) LEGG | |
| HeV | (393) LQGP | (756) MGGP | (958) HEGK | (1096) FEAP | (1277) LEGG | |
| HV | (331) LQGP | (697) LQGP | (876) VEGK | (1009) FEAP | (1190) LEGG | |
| LV | (331) LQGP | (697) LQGP | (876) TEGK | (1009) FEAP | (1190) LEGG | |

FIG. 4

```
1     atgaag atggcgtcta acgacgcttc cgctgccgct gctgtcaaca gcaacaacga
61    caacgcaaaa tcttcaagtg acggagtact atctagtatg gctgtcactt ttaaacgagc
121   ccttggggcc cggcctaaac agccgccccc gagggaaata ccacaaaggc ccccaaggcc
181   acccacccca gaactggtga aaaagatccc acctcccccg cccaacggag aagacgaacc
241   ggtcgttcat tatagtgcta aagatggcat aactgggctg cccgaactta caacagtgag
301   gcagccagaa gaggccgcta cagcattcag cgtcccaccc ctcgaccaga gagagaatag
361   ggacgctaaa gagccattga ccggcaccat cttggagatg tgggatggcg agatttacca
421   ttatggccta tatgtggagc gagggctggt gcttggcgtg cacaaaccac cagccgccat
481   cagcctcgct aaagttgagt taacacctct atctttgtat tggagaccag tgtacacccc
541   ccagtacctc atcgctcctg acaccctcag gaaactgcac ggggagttat ttccatacac
601   ggcctttgat aacaactgct atgccttctg ctgctgggtg ttggacttaa acgattcttg
661   gttgagcaga aggatgatac agagaacaac tggctttttc aggccttacc aagattggaa
721   taggaagccc ctccccacca tggatgactc caagttgaag aaggtggcca acatactttt
781   gtgtgccttg tcatcactat tcactagacc catcaaggac ataattggga aactcaggcc
841   tctcaatatc cttaacatcc tggcttcttg tgattggact ttcgcaggta tagtggaatc
901   tctaattctc ctagctgaac tcttcggagt tttctggaca cccccagatg tgtctgcgat
961   gatcgccccc ttactgggtg actacgagct gcaaggaccc gaagatcttg ctgtggaact
1021  tgtaccgata gtaatggggg ggataggatt ggtgttgggg ttcaccaagg aaaagattgg
1081  gaagatgctg tcatctgccg cttccacccct gaggacctgc aaagaccttg gcgcctatgg
1141  gctggaaatt ctgaaactgg tcatgaaatg gtttttccca aagaaagaag aggcaaacga
1201  gcttgcgatg gtgagggcta ttgaggacgc agtcctagat ctcgaggcta ttgagaacaa
1261  ccatatgaca gctctactca aagacaaaga tagcctcgcg acatacatga ggactcttga
1321  tttggaggaa gaaaaggcca gaaagctctc cactaagtcc gcttcacctg atatagtggg
1381  cacgatcaac gccctgctgg ctagaattgc cgctgctcgt tcccttgtac acaggccaa
1441  ggaagaactg tccagcaggc taaggccagt tgttgtgatg atatctggca aacctggcat
1501  cgggaagacc catctggcta gagaattggc aaagaagatc gctataaccc tttcaggaga
1561  ccagagggta ggcctcatcc cccgcaacgg agtcgaccac tgggatgctt acaagggtga
1621  gagagtcgtt ctctgggacg attatgggat gagtaacccc gtccatgatg ccctaagact
1681  ccaagaactt gctgacacct gccctttgac cctaaactgt gacagaattg agaacaaggg
1741  caaggtcttt gacagtgatg ccataatcat cacaaccaac ctggctaacc cagctccact
1801  tgattatgtc aactttgaag cttgctccag gcgcattgac ttccttgtgt atgccgatgc
1861  acctgacgtt gagaaagcga agcgcgactt cccgggacaa cctgacatgt ggaagagcgc
1921  ttatagtccc gacttctcac acatcaagct aatgctggct ccccagggtg gttttgacaa
1981  aaatggcaac accccacacg ggaaaggtgt catgaagacc ctcacaacag gctccctcat
2041  tgcccgtgct tcagggctcc tccatgaacg attggatgaa ttcgaactac aaggacccaa
2101  cctcacaact ttcaactttg accgtaataa aatacaggct tttaggcagc ttgccgctga
2161  aaacaaatat ggcctggtgg acacaatgag agtgggtgga caactcaagg gtgtcagaac
2221  tataccagaa ctcaagcagg ccctcaagaa catattaatc aaaaggtgcc agatagtgta
2281  tggtggcagc acctatacac ttgaatctga tggcaaaggg aatgtgaaag tggaaaaagt
2341  gcaaaatacc aacatccaaa tcaacaacga gctagctggt gctttacacc acctccgatg
2401  cgctaggatc aggtactatg ttaaatgtgt tcaggaggct ctatattcca tcatccaaat
2461  tgctggggcc gcgtttgtaa ccacgcgcat tgtgaagcgc atgaacatac aaaacttgtg
2521  gtcaaggcct ccagtaggag atgcggagga ggtcactagc caggatggtt gcccaaagcc
2581  caaagatgat gaggagttcg tcatctcgtc tagtgacatc acgcctgaag gcaagaaagg
2641  aaagaacaag actggccgcg gcaagaaaca cacagccttc tcgagcaagg gtctcagtga
2701  tgaggagtac gatgagtaca aaagaatcag ggaagaaagg aatggtaagt actccataga
2761  agaatacctt caggacagag acaagtatta tgaggaagtg gccatagcca gggcaactga
2821  ggaagacttc tgtgaggaag aagaagccaa gatccgacag aggatattta ggccaacgag
2881  gaagcaacgc aaggaggaga gggcttccct tggccttgtc actggctcag agatcagaaa
2941  gagaaaccca gacgacttca aacctaaagg aaagctgtgg gctgatgatg aaagggtcgt
3001  tgactataat gagaaactca gttttgaggc ccccccgagc atctggtcaa ggatagtcaa
3061  ctttgggtca ggatgggggt tctgggtgtc ccctagcctg tttattacat caacccatgt
3121  tataccccaa ggcactcagg aattctttgg tgtacccatc aagcagattc agattcacaa
```

FIG. 4 (continued)

```
3181 atcaggggag ttctgccgcc tgagattccc taaatcaatc agaactgctg taacaggcat
3241 gatcctagaa gagggggccc cagaaggaac cgtggtctca ctactcatca agagaccaac
3301 cggtgagctc atgcccctgg cagccagaat gggcacccat gcgactatga aaatccaagg
3361 tcgcacggtt ggaggtcaga tgggtatgtt gctaacaggg tccaatgcta aaagcatgga
3421 tttgggcacg acacctggtg actgtggctg cccctatatt tataagagag gcaatgacta
3481 cgtggtcatc ggcgtgcaca cagccgctgc tcgcggaggt aacactgtca tctgtgcaac
3541 ccagggcagt gaaggtgagg ccacgctcga aggcggtgat aacaaaggca cctactgtgg
3601 agctccaata ctaggccctg gtaacgctcc caagctcagc accaagacta aattctggag
3661 gtcctccaca gtgccactcc cacccgggac ctatgaacca gcttacttag gtggcaagga
3721 ccccagggtg aagggtggac cttcactaca acaagtcatg agagaccagc taaaaccatt
3781 cactgagcct aggggcaaac cacccaagcc aagtgtgctg gaagctgcca agaagaccat
3841 tatcaatgtg ttggagcaaa caatagatcc cccccaaaaa tggtcatttt cacaagcatg
3901 tgcgtcgctt gataaaacca cctccagcgg ccaccccac cacatacgga agaacgattg
3961 ctggaatggg gagtctttta caggaaaatt ggcagatcaa gcatcaaaag ctaacctaat
4021 gtatgaggaa ggaaagaaca tgaccccagt ctacacaggg gccctcaagg atgagctggt
4081 caagactgac aagatctatg ggcagatcaa gaaaaggctt ctttggggct ctgacttggc
4141 aacaatgatc cgttgtgcgc gggcgtttgg agggttaatg gatgagctca aggcccattg
4201 cgtaacactc cctgtcaggg ttgggatgaa catgaatgag gatggaccca taatttttga
4261 aaagcactcc aggttctcat accactatga tgcagattac tcacgctggg actcaaccca
4321 acagagggca gtgctagctg cagccttgga aatcatggta aaattctcac cagaaccaca
4381 tttggcccaa attgttgcag aggatctcct agcccccagt gtgatggatg taggtgattt
4441 caaaataaca attaatgagg gactgccctc gggagtaccc tgcacatcac agtggaattc
4501 catcgcccac tggctcctca cactctgcgc actatctgaa gtcacaaacc tggctcctga
4561 catcatacaa gctaactcct tgttctcttt ctatggtgat gatgaaatcg taagtactga
4621 cataaaatta gacccagaga aactcacagc aaaactcaaa gaatacggac tcaaaccaac
4681 ccgcccggac aaaactgaag gacccctgat catatccgag gacttgaatg gtttgacctt
4741 tctgcggcgg accgtgaccc gtgatccagc tgggtggttt ggcaagttgg accagagttc
4801 aattctcagg cagatatact ggactagggg ccccaaccat gaggacccgt ccgaaacaat
4861 gataccacac tcccagaggc ctatacagct gatgtctctt ttgggtgaag cagccttgca
4921 tggtccaaca ttttacacca aaatcagtaa actggtcatc acagagctga aggaaggtgg
4981 catggatttt tacgtgccca gacaggaacc catgttcagg tggatgagat tctcagattt
5041 gagcacgtgg gagggcgatc gcaatctggc tcccagtttt gtgaatgaag atggcgtcga
5101 atga
```

(SED ID NO:32)

FIG. 6

```
1: AY134748. Snow Mountain vir...[gi:27762117]  Links

LOCUS       AY134748                 7537 bp    RNA     linear   VRL 15-JAN-2003
DEFINITION  Snow Mountain virus, complete genome.
ACCESSION   AY134748
VERSION     AY134748.1  GI:27762117
KEYWORDS
SOURCE      Snow Mountain virus
  ORGANISM  Snow Mountain virus
            Viruses; ssRNA positive-strand viruses, no DNA stage;
            Caliciviridae; Norovirus.
REFERENCE   1  (bases 1 to 7537)
  AUTHORS   Lochridge,V.P. and Hardy,M.E.
  TITLE     Snow Mountain Virus Genome Sequence and Virus-like Particle
            Assembly
  JOURNAL   Unpublished
REFERENCE   2  (bases 1 to 7537)
  AUTHORS   Lochridge,V.P. and Hardy,M.E.
  TITLE     Direct Submission
  JOURNAL   Submitted (22-JUL-2002) Veterinary Molecular Biology, Montana State
            University, P.O. Box 173610, Bozeman, MT 59717, USA
FEATURES             Location/Qualifiers
     source          1..7537
                     /organism="Snow Mountain virus"
                     /virion
                     /mol_type="genomic RNA"
                     /specific_host="Homo sapiens"
                     /db_xref="taxon:52276"
                     /note="genogroup 2
                     serogroup: 3"
     gene            5..5104
                     /gene="ORF1"
     CDS             5..5104
                     /gene="ORF1"
                     /note="SMV nonstructural proteins"
                     /codon_start=1
                     /product="polyprotein"
                     /protein_id="AAN08111.1"
                     /db_xref="GI:27762118"
                     /translation="MKMASNDASAAAAVNSNNDNAKSSSDGVLSSMAVTFKRALGARP
                     KQPPPREIPQRPPRPPTPELVKKIPPPPPNGEDEPVVHYSAKDGITGLPELTTVRQPE
                     EAATAFSVPPLDQRENRDAKEPLTGTILEMWDGEIYHYGLYVERGLVLGVHKPPAAIS
                     LAKVELTPLSLYWRPVYTPQYLIAPDTLRKLHGELFPYTAFDNNCYAFCCWVLDLNDS
                     WLSRRMIQRTTGFFRPYQDWNRKPLPTMDDSKLKKVANILLCALSSLFTRPIKDIIGK
                     LRPLNILNILASCDWTFAGIVESLILLAELFGVFWTPPDVSAMIAPLLGDYELQGPED
                     LAVELVPIVMGGIGLVLGFTKEKIGKMLSSAASTLRTCKDLGAYGLEILKLVMKWFFP
                     KKEEANELAMVRAIEDAVLDLEAIENNHMTALLKDKDSLATYMRTLDLEEEKARKLST
                     KSASPDIVGTINALLARIAAARSLVHRAKEELSSRLRPVVVMISGKPGIGKTHLAREL
                     AKKIAITLSGDQRVGLIPRNGVDHWDAYKGERVVLWDDYGMSNPVHDALRLQELADTC
                     PLTLNCDRIENKGKVFDSDAIIITTNLANPAPLDYVNFEACSRRIDFLVYADAPDVEK
                     AKRDFPGQPDMWKSAYSPDFSHIKLMLAPQGGFDKNGNTPHGKGVMKTLTTGSLIARA
                     SGLLHERLDEFELQGPNLTTFNFDRNKIQAFRQLAAENKYGLVDTMRVGGQLKGVRTI
                     PELKQALKNILIKRCQIVYGGSTYTLESDGKGNVKVEKVQNTNIQINNELAGALHHLR
                     CARIRYYVKCVQEALYSIIQIAGAAFVTTRIVKRMNIQNLWSRPPVGDAEEVTSQDGC
```

FIG. 6 (continued)

PKPKDDEEFVISSSDITPEGKKGKNKTGRGKKHTAFSSKGLSDEEYDEYKRIREERNG
KYSIEEYLQDRDKYYEEVAIARATEEDFCEEEEAKIRQRIFRPTRKQRKEERASLGLV
TGSEIRKRNPDDFKPKGKLWADDERVVDYNEKLSFEAPPSIWSRIVNFGSGWGFWVSP
SLFITSTHVIPQGTQEFFGVPIKQIQIHKSGEFCRLRFPKSIRTAVTGMILEEGAPEG
TVVSLLIKRPTGELMPLAARMGTHATMKIQGRTVGGQMGMLLTGSNAKSMDLGTTPGD
CGCPYIYKRGNDYVVIGVHTAAARGGNTVICATQGSEGEATLEGGDNKGTYCGAPILG
PGNAPKLSTKTKFWRSSTVPLPPGTYEPAYLGGKDPRVKGGPSLQQVMRDQLKPFTEP
RGKPPKPSVLEAAKKTIINVLEQTIDPPQKWSFSQACASLDKTTSSGHPHHIRKNDCW
NGESFTGKLADQASKANLMYEEGKNMTPVYTGALKDELVKTDKIYGQIKKRLLWGSDL
ATMIRCARAFGGLMDELKAHCVTLPVRVGMNMNEDGPIIFEKHSRFSYHYDADYSRWD
STQQRAVLAAALEIMVKFSPEPHLAQIVAEDLLAPSVMDVGDFKITINEGLPSGVPCT
SQWNSIAHWLLTLCALSEVTNLAPDIIQANSLFSFYGDDEIVSTDIKLDPEKLTAKLK
EYGLKPTRPDKTEGPLIISEDLNGLTFLRRTVTRDPAGWFGKLDQSSILRQIYWTRGP
NHEDPSETMIPHSQRPIQLMSLLGEAALHGPTFYTKISKLVITELKEGGMDFYVPRQE
PMFRWMRFSDLSTWEGDRNLAPSFVNEDGVE" (SEQ ID NO:26)

gene 5085..6713
/gene="ORF2"
CDS 5085..6713
/gene="ORF2"
/note="major capsid protein; VP1"
/codon_start=1
/product="viral protein 1"
/protein_id="AAN08112.1"
/db_xref="GI:27762119"
/translation="MKMASNDAAPSTDGAAGLVPESNNEVMALEPVAGAALAAPVTGQ
TNIIDPWIRANFVQAPNGEFTVSPRNAPGEVLLNLELGPELNPYLAHLARMYNGYAGG
MEVQVMLAGNAFTAGKLVFAAVPPHFPVENLSPQQITMFPHVIIDVRTLEPVLLPLPD
VRNNFFHYNQKDDPKMRIVAMLYTPLRSNGSGDDVFTVSCRVLTRPSPDFDFTYLVPP
TVESKTKPFTLPILTLGELSNSRFPVSIDQMYTSPNEVISVQCQNGRCTLDGELQGTT
QLQVSGICAFKGEVTAHLQDNDHLYNITITNLNGSPFDPSEDIPAPLGVPDFQGRVFG
VITQRDKQNAAGQSQPANRGHDAVVPTYTAQYTPKLGQVQIGTWQTDDLKVNQPVKFT
PVGLNDTEHFNQWVVPRYAGALNLNTNLAPSVAPVFPGERLLFFRSYLPLKGGYGNPA
IDCLLPQEWVQHFYQEAAPSMSEVALVRYINPDTGRALFEAKLHRAGFMTVSSNTSAP
VVVPANGYFRFDSWVNQFYSLAPMGTGNGRRRIQ" (SEQ ID NO:27)

gene 6713..7492
/gene="ORF3"
CDS 6713..7492
/gene="ORF3"
/note="minor structural protein; VP2"
/codon_start=1
/product="viral protein 2"
/protein_id="AAN08113.1"
/db_xref="GI:27762120"
/translation="MAGAFVAGLAGDVLSNGLSSLINAGANAINQRAEFDFNQKLQQN
SFNHDKEMLQAQIQATKQLQADMMAIKQGVLTAGGFSPTDAARGAVNAPMTQALDWNG
TRYWAPGSMRTTSYSGRFTSTAPARQADLQHTQNRPSSGSSVSSYATQSSRPTLTTTT
GSSHSTTSSNSTRSTNLSQSTVSRAASRTSEWVRDQNRNLEPYMHGALQTAFVTPPSS
RASDGTVSTVPKGVLDSWTPAFNTRRQPLFAHLRKRGESQA" (SEQ ID NO:28)

FIG. 6 (continued)

```
ORIGIN
        1 gtgaatgaag atggcgtcta acgacgcttc cgctgccgct gctgtcaaca gcaacaacga
       61 caacgcaaaa tcttcaagtg acggagtact atctagtatg gctgtcactt ttaaacgagc
      121 ccttggggcc cggcctaaac agccgccccc gagggaaata ccacaaaggc ccccaaggcc
      181 acccaccccca gaactggtga aaaagatccc acctcccccg cccaacggag aagacgaacc
      241 ggtcgttcat tatagtgcta aagatggcat aactgggctg cccgaactta caacagtgag
      301 gcagccagaa gaggccgcta cagcattcag cgtcccaccc ctcgaccaga gagagaatag
      361 ggacgctaaa gagccattga ccggcaccat cttggagatg tgggatggcg agatttacca
      421 ttatggccta tatgtggagc gagggctggt gcttggcgtg cacaaaccac cagccgccat
      481 cagcctcgct aaagttgagt taacacctct atctttgtat tggagaccag tgtacacccc
      541 ccagtacctc atcgctcctg acaccctcag gaaactgcac ggggagttat ttccatacac
      601 ggcctttgat aacaactgct atgccttctg ctgctgggtg ttggacttaa acgattcttg
      661 gttgagcaga aggatgatac agagaacaac tggctttttc aggccttacc aagattggaa
      721 taggaagccc ctccccacca tggatgactc caagttgaag aaggtggcca acatactttt
      781 gtgtgccttg tcatcactat tcactagacc catcaaggac ataattggga aactcaggcc
      841 tctcaatatc cttaacatcc tggcttcttg tgattggact ttcgcaggta tagtggaatc
      901 tctaattctc ctagctgaac tcttcggagt tttctggaca cccccagatg tgtctgcgat
      961 gatcgccccc ttactgggtg actacgagct gcaaggaccc gaagatcttg ctgtggaact
     1021 tgtaccgata gtaatggggg ggataggatt ggtgttgggg ttcaccaagg aaaagattgg
     1081 gaagatgctg tcatctgccg cttccaccct gaggacctgc aaagaccttg gcgcctatgg
     1141 gctggaaatt ctgaaactgg tcatgaaatg gtttttccca aagaaagaag aggcaaacga
     1201 gcttgcgatg gtgagggcta ttgaggacgc agtcctagat ctcgaggcta ttgagaacaa
     1261 ccatatgaca gctctactca aagacaaaga tagcctcgcg acatacatga ggactcttga
     1321 tttggaggaa gaaaaggcca gaaagctctc cactaagtcc gcttcacctg atatagtggg
     1381 cacgatcaac gccctgctgg ctagaattgc cgctgctcgt tcccttgtac acagggccaa
     1441 ggaagaactg tccagcaggc taaggccagt tgttgtgatg atatctggca aacctggcat
     1501 cgggaagacc catctggcta gagaattggc aaagaagatc gctataaccc tttcaggaga
     1561 ccagagggta ggcctcatcc cccgcaacgg agtcgaccac tgggatgctt acaagggtga
     1621 gagagtcgtt ctctgggacg attatgggat gagtaacccc gtccatgatg ccctaagact
     1681 ccaagaactt gctgacacct gccctttgac cctaaactgt gacagaattg agaacaaggg
     1741 caaggtcttt gacagtgatg ccataatcat cacaaccaac ctggctaacc cagctccact
     1801 tgattatgtc aactttgaag cttgctccag gcgcattgac ttccttgtgt atgccgatgc
     1861 acctgacgtt gagaaagcga agcgcgactt cccgggacaa cctgacatgt ggaagagcgc
     1921 ttatagtccc gacttctcac acatcaagct aatgctggct ccccagggtg gttttgacaa
     1981 aaatggcaac accccacacg ggaaaggtgt catgaagacc ctcacaacag gctccctcat
     2041 tgcccgtgct tcagggctcc tccatgaacg attggatgaa ttcgaactac aaggacccaa
     2101 cctcacaact ttcaactttg accgtaataa aatacaggct tttaggcagc ttgccgctga
     2161 aaacaaatat ggcctggtgg acacaatgag agtgggtgga caactcaagg gtgtcagaac
     2221 tataccagaa ctcaagcagg ccctcaagaa catattaatc aaaaggtgcc agatagtgta
     2281 tggtggcagc acctatacac ttgaatctga tggcaaaggg aatgtgaaag tggaaaaagt
     2341 gcaaaatacc aacatccaaa tcaacaacga gctagctggt gctttacacc acctccgatg
     2401 cgctaggatc aggtactatg ttaaatgtgt tcaggaggct ctatattcca tcatccaaat
     2461 tgctggggcc gcgtttgtaa ccacgcgcat tgtgaagcgc atgaacatac aaaacttgtg
     2521 gtcaaggcct ccagtaggag atgcggagga ggtcactagc caggatggtt gcccaaagcc
     2581 caaagatgat gaggagttcg tcatctcgtc tagtgacatc acgcctgaag gcaagaaagg
     2641 aaagaacaag actggccgcg gcaagaaaca cacagccttc tcgagcaagg gtctcagtga
     2701 tgaggagtac gatgagtaca aaagaatcag ggaagaaagg aatggtaagt actccataga
     2761 agaatacctt caggacagag acaagtatta tgaggaagtg gccatagcca gggcaactga
     2821 ggaagacttc tgtgaggaag aagaagccaa gatccgacag aggatattta ggccaacgag
     2881 gaagcaacgc aaggaggaga gggcttccct tggccttgtc actggctcag agatcagaaa
     2941 gagaaaccca gacgacttca aacctaaagg aaagctgtgg gctgatgatg aaagggtcgt
     3001 tgactataat gagaaactca gttttgaggc ccccccgagc atctggtcaa ggatagtcaa
     3061 ctttgggtca ggatgggggt tctgggtgtc ccctagcctg tttattacat caacccatgt
     3121 tataccccaa ggcactcagg aattctttgg tgtacccatc aagcagattc agattcacaa
```

FIG. 6 (continued)

3181 atcaggggag ttctgccgcc tgagattccc taaatcaatc agaactgctg taacaggcat
3241 gatcctagaa gagggggccc cagaaggaac cgtggtctca ctactcatca agagaccaac
3301 cggtgagctc atgcccctgg cagccagaat gggcacccat gcgactatga aaatccaagg
3361 tcgcacggtt ggaggtcaga tgggtatgtt gctaacaggg tccaatgcta aagcatgga
3421 tttgggcacg acacctggtg actgtggctg cccctatatt tataagagag gcaatgacta
3481 cgtggtcatc ggcgtgcaca cagccgctgc tcgcggaggt aacactgtca tctgtgcaac
3541 ccagggcagt gaaggtgagg ccacgctcga aggcggtgat aacaaaggca cctactgtgg
3601 agctccaata ctaggccctg gtaacgctcc caagctcagc accaagacta aattctggag
3661 gtcctccaca gtgccactcc cacccgggac ctatgaacca gcttacttag gtggcaagga
3721 ccccagggtg aagggtggac cttcactaca acaagtcatg agagaccagc taaaaccatt
3781 cactgagcct aggggcaaac caccccaagcc aagtgtgctg gaagctgcca agaagaccat
3841 tatcaatgtg ttggagcaaa caatagatcc cccccaaaaa tggtcatttt cacaagcatg
3901 tgcgtcgctt gataaaacca cctccagcgg ccaccccac cacatacgga agaacgattg
3961 ctggaatggg gagtctttta caggaaaatt ggcagatcaa gcatcaaaag ctaacctaat
4021 gtatgaggaa ggaaagaaca tgaccccagt ctacacaggg gccctcaagg atgagctggt
4081 caagactgac aagatctatg ggcagatcaa gaaaaggctt ctttggggct ctgacttggc
4141 aacaatgatc cgttgtgcgc gggcgtttgg agggttaatg gatgagctca aggcccattg
4201 cgtaacactc cctgtcaggg ttgggatgaa catgaatgag gatggaccca taatttttga
4261 aaagcactcc aggttctcat accactatga tgcagattac tcacgctggg actcaaccca
4321 acagagggca gtgctagctg cagccttgga aatcatggta aaattctcac cagaaccaca
4381 tttggcccaa attgttgcag aggatctcct agcccccagt gtgatggatg taggtgattt
4441 caaaataaca attaatgagg gactgccctc gggagtaccc tgcacatcac agtggaattc
4501 catcgcccac tggctcctca cactctgcgc actatctgaa gtcacaaacc tggctcctga
4561 catcatacaa gctaactcct tgttctcttt ctatggtgat gatgaaatcg taagtactga
4621 cataaaatta gacccagaga aactcacagc aaaactcaaa gaatacggac tcaaaccaac
4681 ccgcccggac aaaactgaag gacccctgat catatccgag gacttgaatg gtttgacctt
4741 tctgcggcgg accgtgaccc gtgatccagc tgggtggttt ggcaagttgg accagagttc
4801 aattctcagg cagatatact ggactagggg ccccaaccat gaggacccgt ccgaaacaat
4861 gataccacac tcccagaggc ctatacagct gatgtctctt ttgggtgaag cagccttgca
4921 tggtccaaca ttttacacca aaatcagtaa actggtcatc acagagctga aggaaggtgg
4981 catggatttt tacgtgccca gacaggaacc catgttcagg tggatgagat tctcagattt
5041 gagcacgtgg gagggcgatc gcaatctggc tcccagtttt gtgaatgaag atggcgtcga
5101 *atga*cgccgc tccatctact gatggtgcag ccggcctcgt gccagaaagt aataatgagg
5161 tcatggctct tgagcccgtg gctggtgctg ccttggcagc ccccggtcacc ggtcaaacaa
5221 atattataga ccccttggatt agagcaaatt ttgtccaggc ccctaatggt gaatttacag
5281 tttctccccg taatgcccct ggtgaagtgc tattaaatct agaattgggt ccagaattaa
5341 atccttatct ggcacattta gcaagaatgt acaacgggta tgccggtggg atggaggtgc
5401 aggtcatgct agctgggaac gcgttcacag ctggcaaatt ggtcttcgct gctgtaccac
5461 ctcatttccc ggttgaaaac cttagtccac agcaaattac catgttccct catgtgatta
5521 tagatgttag gactttggaa cctgttttat tgccactccc cgatgttaga aataatttct
5581 tccattataa tcaaaaagat gatcctaaga tgagaattgt ggctatgctt tatactcccc
5641 tcaggtccaa tggttctggt gatgatgtgt tcacagtctc ttgcagggtg ttgactagac
5701 cctcccctga ttttgatttt acatacctgg taccaccaac agtggaatcc aaaacaaaac
5761 cattcaccct tccaattctt acacttgggg agctttccaa ttctagattt ccagtgtcca
5821 tagatcagat gtacactagc cccaatgaag tcatatctgt gcagtgccag aatggaaggt
5881 gcacactgga tggggagctc caaggaacaa cacagctcca agttagtggc atttgtgcat
5941 tcaaaggaga agtgaccgct cacttgcagg acaatgatca cctatacaac atcaccatca
6001 caaacttgaa tgggtcccct tttgatccct ctgaggacat ccccgccccc ctgggtgtgc
6061 ccgactttca gggaagagtc tttggtgtca tcactcaaag agacaaacag aatgccgctg
6121 ggcaaagcca gccggcaaac aggggacacg atgctgtggt ccccacttac acagcccagt
6181 ataccccaaa attgggtcag gttcaaattg gcacatggca gaccgacgat cttaaagtca
6241 accaaccagt caaattcacc ccagtcggtc tcaatgacac agaacatttc aatcagtggg
6301 tggtccctag gtacgctggt gctttaaatc taaacacaaa tcttgccccc tctgttgctc
6361 cagtgtttcc aggggagcgt ctgctcttct ttagatcata cctccccctt aagggtggtt
6421 atggaaaccc agctattgat tgcctgctac cacaagagtg ggtgcagcat ttttatcagg

FIG. 6 (continued)

6481 aagcagcccc ctcaatgagt gaggtagccc ttgtcagata catcaatccg gacactggcc
6541 gggcgctgtt tgaggccaaa ctccacagag ctggtttcat gacagtctcg agtaacacca
6601 gtgctccggt ggttgtgcct gccaacggat acttcagatt tgactcttgg gtgaaccaat
6661 tttattctct tgccccatg ggaactggaa atgggcgtag aaggattcag tgatggctgg
6721 agcttttgta gctggtctcg cgggggatgt gctcagcaat gggctcagct cactaattaa
6781 tgcaggtgct aatgcaataa atcagagagc agaatttgat tttaatcaga aattacagca
6841 aaattctttt aatcatgata aggagatgtt gcaggctcag attcaggcaa ctaagcagct
6901 gcaggcagac atgatggcta taaagcaggg ggttctgacc gctggcggct tttcccctac
6961 tgatgcagcc agaggcgctg tgaacgcgcc catgacacag gcgctggatt ggaatggcac
7021 aaggtattgg gcaccaggct ccatgaggac tacatcctac tctgggaggt tcacatcgac
7081 cgccccggca aggcaggccg atcttcaaca cactcaaaat cggccttcga gtggctcttc
7141 tgtgtcctct tatgccactc aatcttcaag accaactcta accacaacca cagggtcctc
7201 acatagtaca acctcatcca attcgacccg tagcacaaac ctttcccagt cgacggtctc
7261 tagggctgca tccaggacta gtgagtgggt tagagatcaa aatagaaatt tggaacccta
7321 catgcatggt gccttacaga cagcctttgt caccccacct tccagcaggg catctgacgg
7381 gacagtctca accgtcccca aaggtgtttt ggactcctgg acacctgcgt tcaacacccg
7441 caggcagccg ctttttgcac acctccgtaa gagggggag tcacaagctt agtgaaaagg
7501 tgaaaatttt actttaaatg aattgattct acctttt

(SEQ ID NO:29)

FIG. 7

```
5085                                                          atgaag atggcgtcga
5101 atgacgccgc tccatctact gatggtgcag ccggcctcgt gccagaaagt aataatgagg
5161 tcatggctct tgagcccgtg gctggtgctg ccttggcagc cccggtcacc ggtcaaacaa
5221 atattataga cccttggatt agagcaaatt ttgtccaggc ccctaatggt gaatttacag
5281 tttctccccg taatgcccct ggtgaagtgc tattaaatct agaattgggt ccagaattaa
5341 atccttatct ggcacattta gcaagaatgt acaacgggta tgccggtggg atggaggtgc
5401 aggtcatgct agctgggaac gcgttcacag ctggcaaatt ggtcttcgct gctgtaccac
5461 ctcatttccc ggttgaaaac cttagtccac agcaaattac catgttccct catgtgatta
5521 tagatgttag gactttggaa cctgttttat tgccactccc cgatgttaga aataatttct
5581 tccattataa tcaaaaagat gatcctaaga tgagaattgt ggctatgctt tatactcccc
5641 tcaggtccaa tggttctggt gatgatgtgt tcacagtctc ttgcagggtg ttgactagac
5701 cctcccctga ttttgatttt acatacctgg taccaccaac agtggaatcc aaaacaaaac
5761 cattcaccct tccaattctt acacttgggg agctttccaa ttctagattt ccagtgtcca
5821 tagatcagat gtacactagc cccaatgaag tcatatctgt gcagtgccag aatggaaggt
5881 gcacactgga tggggagctc caaggaacaa cacagctcca agttagtggc atttgtgcat
5941 tcaaaggaga agtgaccgct cacttgcagg acaatgatca cctatacaac atcaccatca
6001 caaacttgaa tgggtcccct tttgatccct ctgaggacat ccccgccccc ctgggtgtgc
6061 ccgactttca gggaagagtc tttggtgtca tcactcaaag agacaaacag aatgccgctg
6121 ggcaaagcca gccggcaaac aggggacacg atgctgtggt ccccacttac acagcccagt
6181 ataccccaaa attgggtcag gttcaaattg gcacatggca gaccgacgat cttaaagtca
6241 accaaccagt caaattcacc ccagtcggtc tcaatgacac agaacatttc aatcagtggg
6301 tggtccctag gtacgctggt gctttaaatc taaacacaaa tcttgccccc tctgttgctc
6361 cagtgtttcc aggggagcgt ctgctcttct ttagatcata cctccccctt aagggtggtt
6421 atggaaaccc agctattgat tgcctgctac cacaagagtg ggtgcagcat ttttatcagg
6481 aagcagcccc ctcaatgagt gaggtagccc ttgtcagata catcaatccg gacactggcc
6541 gggcgctgtt tgaggccaaa ctccacagag ctggtttcat gacagtctcg agtaacacca
6601 gtgctccggt ggttgtgcct gccaacggat acttcagatt tgactcttgg gtgaaccaat
6661 tttattctct tgcccccatg ggaactggaa atgggcgtag aaggattcag tga
```

(SEQ ID NO:30)

FIG. 8

```
6713                                                              atggctgg
6721 agcttttgta gctggtctcg cgggggatgt gctcagcaat gggctcagct cactaattaa
6781 tgcaggtgct aatgcaataa atcagagagc agaatttgat tttaatcaga aattacagca
6841 aaattctttt aatcatgata aggagatgtt gcaggctcag attcaggcaa ctaagcagct
6901 gcaggcagac atgatggcta taaagcaggg ggttctgacc gctggcggct tttcccctac
6961 tgatgcagcc agaggcgctg tgaacgcgcc catgacacag gcgctggatt ggaatggcac
7021 aaggtattgg gcaccaggct ccatgaggac tacatcctac tctgggaggt tcacatcgac
7081 cgcccccggca aggcaggccg atcttcaaca cactcaaaat cggccttcga gtggctcttc
7141 tgtgtcctct tatgccactc aatcttcaag accaactcta accacaacca cagggtcctc
7201 acatagtaca acctcatcca attcgacccg tagcacaaac ctttcccagt cgacggtctc
7261 tagggctgca tccaggacta gtgagtgggt tagagatcaa aatagaaatt tggaacccta
7321 catgcatggt gccttacaga cagcctttgt caccccacct tccagcaggg catctgacgg
7381 gacagtctca accgtcccca aaggtgtttt ggactcctgg acacctgcgt tcaacacccg
7441 caggcagccg ctttttgcac acctccgtaa gagggggag tcacaagctt ag
```
(SEQ ID NO:31)

SNOW MOUNTAIN VIRUS GENOME SEQUENCE, VIRUS-LIKE PARTICLES AND METHODS OF USE

CROSS REFERENCE TO RELATED APPLICATION(S)

This application claims the benefit of the filing date under 35 U.S.C. § 119(e) of U.S. Application Ser. No. 60/544,386, filed Feb. 12, 2004.

STATEMENT OF GOVERNMENT SUPPORT

This work was supported by Public Health Service grant AI-43450 and by a subcontract from LigoCyte Pharmaceuticals, Inc., Bozeman, Mont., which is supported by the U.S. Army Medical Research and Material Command under Contract No. DAM 17-0 1-C-0040. The government has certain rights in the invention.

INTRODUCTION

Snow Mountain virus (SMV) is a prototype human calicivirus strain within the Norovirus genus of the Caliciviridae family. These viruses are the major cause of epidemic outbreaks of acute gastroenteritis worldwide. (Frankhauser et al. J. Infect. Dis. 178:1571-1578 (1998); Koopmans et al. J. Infect. Dis. 2000 181 Suppl. 2:S262-69; Noel et al. J. Infect. Dis. 1999 179:1334-1344; Dedman et al. Epidemiol. Infect. 1998 121:139-149.) Human enteric caliciviruses (HuCV) are transmitted through fecal contamination of food and water. Attack rates are high and rapid secondary person-to-person spread is common, resulting in large outbreaks that often persist. (Green et al., *Human Caliciviruses vol.* 1, 841874 (Knipe and Howley, 3d eds-in-chief., Lippincott Williams & Wilkins 2001 (ISBN 0-7817-1832-5); Kapikian et al. Norwalk Group of Viruses, in *Fields Virology,* 3" edn. 1996, pp. 783-810.) The positivesense RNA genomes of the human caliciviruses are an average of 7,500 nucleotides (nt) in length, polyadenylated at the 3' end, and contain three open reading frames (ORFs). (Clarke et al. J Infect Dis. 2000 181 Suppl 2:S309-16.) ORF I is translated into a large polyprotein that is cleaved by a viral protease into the nonstructural proteins. (Clarke et al. J Infect Dis. 2000 181 Suppl 2:S309-16.) ORF2 encodes the major capsid protein VPI. (Jiang et al. J Virol. 1992 November; 66(11):6527-32.) ORF3 encodes a minor structural protein VP2. (Wirblich et al. J Virol. 1996 November; 70(11):7974-83; Glass et al. J Virol. 2000 July; 74(14):6581-91.)

SMV was first identified as the cause of an outbreak of acute gastroenteritis at a Colorado resort camp in 1976. (Morens et al. Lancet. 1979 May 5; 1(8123):964-6.) The water supply had become contaminated by a septic tank leak, which resulted in 55% of the guests reporting illness. SMV was the third antigenically distinct human calicivirus defined by immune electron microscopy in 1982. (Dolin et al. J Infect Dis. 1982 August; 146(2): 184-9.) Classification of SMV and other HuCV has been difficult due to the inability to cultivate the viruses in cell culture. However, analyses of sequence encoding the RNA polymerase and capsid proteins has allowed classification of the HuCVs into groups based on genetic similarity, called genogroups. (Lew et al. J Infect Dis. 1994 September; 170(3):535-42.) SMV is a genogroup II (GII) reference strain HuCV first characterized at the molecular level by sequence comparison of a portion of the RNA polymerase region and capsid sequence. (Wang et al. J Virol. 1994 September; 68(9):5982-90; Ando et al. Arch Virol. 1994; 135(1-2):217-26; Hardy et al. Arch Virol. 1997; 142 (7):1469-79; King et al. Virus Genes. 1997; 15(1):5-7.)

Complete genome sequences have been determined for 8 noroviruses. The GI strains include Southhampton virus (SHV), Norwalk virus (NV), Hesse virus (HeV), and Chiba virus. (Lambden et al. Science. 1993 Jan. 22; 259(5094):516-9; Jiang et al. Virology. 1993 July; 195(1):51-61; Hardy et al. Virus Genes. 1996; 12(3):287-90; Schreier et al. Arch Virol. 2000; 145(3):443-53; Someya et al. Virology. 2000 Dec. 20; 278(2):490-500). The GII viruses include Lordsdale virus (LV), Camberwell virus, Maryland virus (MD-145), and Hawaii virus (HV). (Dingle et al. J Gen Virol. 1995 September; 76 (Pt 9):2349-55; Seah et al. J Virol. 1999 December; 73(12):10531-5; Green et al. J Infect Dis. 2002 Jan. 15; 185 (2):133-46. Epub 2002 Jan. 3; Pletneva et al. Virus Genes. 2001; 23(1):5-16.)

The present invention provides the cloning and sequencing of the full-length genome of SMV, and expression of VP1 and VP2 capsid proteins by recombinant baculovirus to produce self-assembling virus-like particles (VLPs).

The nucleic acid and polypeptide sequences and the VLPs of SMV find use as diagnostic agents and immunogens.

SUMMARY

The invention generally relates to the nucleotide sequence of Snow Mountain virus (SMV) genomic RNA (vRNA) and the deduced amino acid sequences of the encoded SMV proteins. Thus, the invention provides methods of cloning and sequencing a SMV vRNA and deducing the amino acid sequence of the encoded SMV proteins.

In some embodiments, the invention provides SMV nucleic acids including fragments of full length SMV nucleic acids. The nucleic acids find use as probes in nucleic acid hybridization based assays. Therefore, SMV nucleic acids find use in methods of detecting, analyzing, quantitating, or locating SMV nucleic acids, and identifying SMV disease states.

In some embodiments, the invention provides SMV proteins including fragments of full length SMV proteins. In some embodiments, SMV proteins can be a SMV-like particle. In some embodiments, the SMV proteins can be immunogenic. In some embodiments, SMV proteins can be formulated with an adjuvant. Thus, the SMV proteins find use in methods of inducing an immune response to SMV making antibody to SMV proteins, and methods of making SMV-like particles.

In some embodiments, the invention provides a composition comprising a virus-like particle comprising Snow Mountain virus VP1 protein and Snow Mountain virus VP2 protein.

In some embodiments, a Snow Mountain virus VP2 protein can comprise a sequence that can be greater than 98% identical to SEQ ID NO:28. In some embodiments, a VP2 protein can comprise a sequence that is identical to SEQ ID NO:28. In some embodiments, a VP2 protein can be encoded by a nucleic acid comprising a sequence that is greater than 97% identical to SEQ ID NO:31. In some embodiments, a VP2 protein can be encoded by a nucleic acid that comprises a sequence that encodes for an amino acid sequence that can be greater than 98% identical to SEQ ID NO:28.

In some embodiments, a Snow Mountain virus VP1 protein comprises a sequence that can be greater than 98% identical to SEQ ID NO:27. In some embodiments, a VP1 protein can comprise a sequence that can be identical to SEQ ID NO:27. In some embodiments, a VP1 protein can be encoded by a nucleic acid that comprises a sequence that can be greater than 94% identical to SEQ ID NO:30. In some embodiments, a VP1 protein can be encoded by a nucleic acid comprising a sequence identical to SEQ ID NO:30. In some embodiments, a VP1 protein can be encoded by a nucleic acid that comprises a sequence that encodes an amino acid sequence that can be greater than 98% identical to SEQ ID NO:27.

In some embodiments, a composition disclosed herein can comprise a Snow Mountain virus virus-like particle in an amount suitable for inducing an immune response to Snow Mountain virus, Snow Mountain virus virus-like particle, and/or cells expressing a Snow Mountain virus in a subject. In some embodiments, the composition can further comprise an adjuvant. In various exemplary embodiments, the immune response that is induced can include an antibody response, a T cell response. In some embodiments, a composition further comprises a carrier.

In some embodiments, the invention provides methods of making a virus-like particle comprising co-expressing Snow Mountain virus VP1 protein and Snow Mountain virus VP2 protein in a recombinant nucleic acid expression system under conditions suitable for assembly of the expressed VP1 and VP2 proteins into a virus-like particle. In some embodiments, an expression system can comprise a eukaryotic cell. In some embodiments, a eukaryotic cell can be an Sf9 cell. In some embodiments, a recombinant expression system can be a baculovirus expression system.

In some embodiments, the invention provides methods of inducing an immune response in a subject comprising administering a subject a composition comprising an immunogenic dose of Snow Mountain virus-like particles comprising Snow Mountain virus VP1 protein and Snow Mountain virus VP2 proteins. In some embodiments, an immune response can be an antibody response.

In some embodiments, the invention provides a Snow Mountain virus proteins having an R residue at a position that corresponds to position 91 of SMV VP1 protein (H91R-VP1 protein). In some embodiments, the H91R-VP1 protein is not substantially incorporated into virus-like particles under conditions that are otherwise suitable for wild type VP1 protein incorporation into virus-like particles. In some embodiments, expression of H91R-VP1 protein in a cell inhibits wild-type VP1 protein incorporation into virus-like particles.

BRIEF DESCRIPTION OF THE DRAWINGS

The skilled artisan will understand that the drawings, described below, are for illustration purposes only. The drawings are not intended to limit the scope of the present teachings in any way.

FIG. 4 shows the nucleotide sequence encoding SMV polyprotein (ORF1) (SEQ ID NO:32). (Hardy et al. Virus Genes 2003 26(1):71-82 (expressly incorporated by reference); Genbank AY134748 (expressly incorporated by reference).

FIG. 6 shows the complete SMV genome sequence (SEQ ID NO:29) and deduced amino acid sequences of the polyprotein (SEQ ID NO:26), VP1 (SEQ ID NO:27) and VP2 (SEQ ID NO:28). (Hardy et al. Virus Genes 2003 26(1):71-82 (expressly incorporated by reference); Genbank AY134748 (expressly incorporated by reference).

FIG. 7 shows the nucleotide sequence (ORF2) encoding SMV VP1 (SEQ ID NO:30). (Hardy et al. Virus Genes 2003 26(1):71-82 (expressly incorporated by reference); Genbank AY134748 (expressly incorporated by reference).

FIG. 8 shows the nucleotide sequence (ORF3) encoding SMV VP2 (SEQ ID NO:31). (Hardy et al. Virus Genes 2003 26(1):71-82 (expressly incorporated by reference); Genbank AY134748 (expressly incorporated by reference).

DETAILED DESCRIPTION OF PREFERRED EMBODIMENTS

Figure 1:
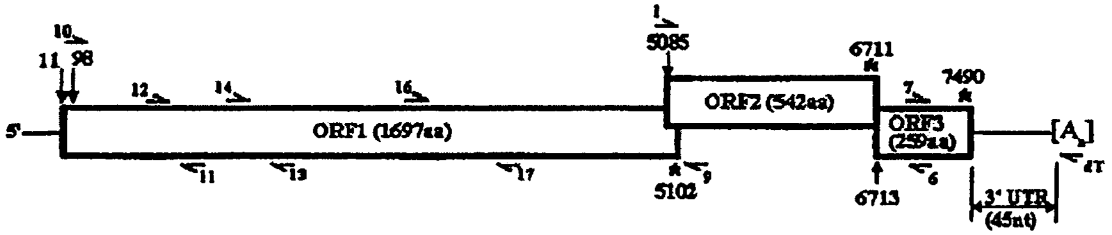
FIG. 1 shows the genome organization of SMV. The SMV genome is 7537 nucleotides and has three major open reading frames (ORFs). The 5' untranslated sequence 5'-GUGAAUGAAG (SEQ ID NO:15) (assuming translation starts at nucleotide 11) and the 3' untranslated region (UTR) is 45 nts preceding a polyadenylated tail. In-frame start codons in strong context are indicated by an arrow and nucleotide position. Stop positions are sequences and indicated by an asterisk. Horizontal arrows indicate position of primers used to transcribe and amplify the vRNA. Primer positions are in Table. 1.

The present invention is directed to the discovery of the nucleotide sequence of the genomic RNA (vRNA) of Snow Mountain virus (SMV) and the deduced amino acid sequences encoded by SMV vRNA. The nucleotide and amino acid sequences find use as immunogens and diagnostic reagents.

Thus, in addition to compositions, the present invention provides methods of inducing an immune response to SMV and diagnosing SMV disease in a subject.

In some embodiments, the present invention provides SMV-like particles (VLPs). VLPs comprise SMV capsid proteins, VP1 and VP2, and can be assembled in vitro from VP1 and VP2 proteins expressed from isolated, recombinant vectors. Thus, the present invention provides methods of making SMV VLPs (rSMV). The VLPs find use as immunogens and diagnostic agents and therefore can be used in methods of inducing an immune response and diagnosing SMV disease.

In another aspect, the present invention provides an SMV VP1 having a histidine (H) to arginine (R) amino acid substitution at position 91 of SMV VP1 (H91R). The H91R-VP1 does not substantially assemble into VLPs with VP2 under conditions otherwise suitable for VLP assembly. Thus, the H91R substitution is important in VLP assembly and finds use in methods of inhibiting VLP assembly. In some embodiments, synthetic analogs and mimetic structures of H91R-VP1 can be used to inhibit VLP assembly.

In another aspect, the invention provides isolated SMV antibodies to SMV amino acid sequences. The antibodies can be polyclonal or monoclonal and can be made to SMV proteins. In some embodiments, the antibodies can be to at least one SMV amino acid sequence. In some embodiments, the antibodies can be cross-reactive with at least one other GII virus sequence. In some embodiments, the antibodies can be cross-reactive with at least one other Norovirus. In some embodiments, the antibodies can be to a polymolecular structure comprising at least two SMV proteins (e.g., a hetero- or homomultimer), such as, a SMV virion or VLP. Thus, the antibodies find use in methods diagnosing SMV disease caused by other GII viruses and other Noroviruses.

Accordingly, the present invention provides nucleotide and amino acid sequences of SMV vRNA and/or transcripts thereof. "Snow Mountain virus (SMV)" and grammatical equivalents are used herein to refer to a prototype strain of human caliciviruses within GII of the Norovirus genus of the Caliciviridae family. The skilled artisan will appreciate that "SMV" includes infectious virions and non-infectious virions, which include defective and defective-interfering particles. "Norovirus" as used herein refers to a genus of related, positive-sense single-stranded RNA, nonenveloped viruses that cause acute gastroenteritis in humans. Noroviruses also can be referred to as small round structured viruses (SRSVs) having a defined surface structure or ragged edge when viewed by electron microscopy. Included within the Noroviruses are at least four genogroups (GI-IV) defined by comparisons of nucleic acid and amino acid sequences, which comprise at least 20 genetic clusters (see, e.g., *Virus Taxonomy: The Classification and Nomenclature of Viruses. The Seventh Report of the International Committee on Taxonomy of Viruses* (van Regenmortel et al. eds., Virus Taxonomy, VIIth report of the ICTV. Academic Press 2000) and Green et al., *Human Caliciviruses vol.* 1, 841-874 (Knipe and Howley, 3d eds-in-chief., Lippincott Williams & Wilkins 2001 (ISBN 0-7817-1832-5), expressly incorporated by reference) "rSMV" as used herein refers to recombinant SMV virus-like particles (e.g., VLP and rVLP). Recombinant expression of SMV capsid proteins encoded by open reading frame 2 (VP1) and open reading frame 3 (VP2) from recombinant vector(s) under suitable conditions results in assembly of the expressed capsid protein into VLPs. In some embodiments, a VLP can be structurally similar to SMV but lack the vRNA and therefore are not infectious.

The present invention provides a variety of proteins including SMV proteins (including capsid proteins) and fragments thereof and SMV antibodies. "Peptide", "polypeptide", "oligopeptide" and "protein" are used interchangeably and refer to a polymer of at least two covalently attached amino acid residues. "Amino acid" as used herein refers to a molecule containing amino and carboxylic acid groups and therefore includes but is not limited to α-, β-, β-amino acids and so on, imino acids (e.g., proline, hydroxyproline, histidine) and the like. "Amino acid residue" and "peptide residue" as used herein refer to what remains of an amino acid after an amino acid is covalently attached via a peptide bond. "Amino acid", "amino acid residue", and "peptide residue" as used herein include molecules having naturally occurring and synthetic structures (e.g., naturally occurring amino acids, amino acid analogs, peptide bonds, synthetic peptidomimetic structures (e.g., "peptoids" (see Simon et al., PNAS USA 89(20):9367 (1992)), γ-linkages, homophenylalanine, citrulline, norleucine). One or more side chains may be in either the (R) or the (S) configuration. In a preferred embodiment, all side chains can be in the (S) or L-configuration. In a preferred embodiment, the side chains can be in a configuration suitable for inducing an immune response to an SMV protein. In some embodiments, non-amino acid substituents can be attached to a peptide, for example, to prevent or retard in vivo degradation. A peptide that includes a non-naturally occurring side chain and/or other structure may be synthesized or in some cases, made recombinantly. (Hest et al. FEBS Lett. 428(1-2): 68-70 (1998), Tang et al., Abstr. Pap. Am. Chem. S218:U138 Part 2 Aug. 22, 1999).

By "SMV protein," "SMV peptide," "viral protein," "viral peptide" and grammatical equivalents herein are meant a protein having a sequence homologous or identical to an amino acid sequence deduced from a SMV ORF and does not cause or exacerbate SMV disease when administered to a subject. In some embodiments, an SMV protein can be an isolated protein. "Isolated protein" as used herein refers to a protein separated or purified away from at least one molecule or component with which the protein is normally associated. Therefore, in some embodiments, an isolated protein can be a protein that is produced by SMV that is purified or isolated from at least one molecule or component with which the protein is normally associated. In some embodiments, an SMV protein can be a recombinant protein. "Recombinant protein" as used herein refers to a protein produced using the techniques of molecular biology and therefore can be produced by expression of an isolated or recombinant or synthetic nucleic acid comprising a suitable nucleic acid sequence and encodes a suitable amino acid sequence, as described below. In some embodiments, an SMV protein can be a synthetic protein. "Synthetic protein" as used herein refers to a protein produced using the techniques of organic chemistry, including but not limited to, solid-phase synthesis, as known in the art. In some embodiments, an SMV protein can be a non-structural protein, which refers to a protein that is not found in SMV virons as they occur in nature and/or VLPs. In some embodiments, SMV proteins can be structural proteins (e.g., capsid proteins), such as, VP1 and VP2, and therefore can be found in SMV virions as they occur in nature or VLPs comprising SMV proteins (SMV VLPs). Thus, "SMV proteins" includes SMV VP1 and VP2 and fragments of the full-length SMV proteins. In various exemplary embodiments, a SMV protein can be about 5 to about 50 amino acids in length. In some embodiments, an SMV protein can be about 5 to about 30 amino acids in length. In some embodiments, an SMV protein can about 5 to about 15 amino acids in length. In various exemplary embodiments, an SMV protein can comprise about 1%, 5%, 10%, 15%, 20%, 25%, 30%, 35%, 40%, 45%, 50%, 55%, 60%, 65%, 70%, 75%, 80%, 85%, 90%, 95%, 99%, or 100% of the number of amino acids comprising a full length SMV protein.

By "SMV capsid," "SMV capsid protein," "SMV capsid peptide," "SMV capsid polypeptide" and grammatical equivalents herein are meant a protein comprising a sequence homologous or identical to the deduced amino acid sequence of ORF2 or ORF3 of a SMV. As used herein, a protein can be a "SMV capsid protein" if the overall homology of the protein sequence to an amino acid sequences of an SMV capsid protein is preferably greater than about 75%, more preferably greater than about 80%, even more preferably greater than about 85% and most preferably greater than 90%. In some embodiments the homology will be as high as about 93 to 95 or 98%. In an even more preferred embodiment, the homology is greater than 98%. Homology in this context means sequence similarity or identity, with identity being preferred.

The skilled artisan will appreciate that homology can be determined using standard techniques known in the art as described below.

In a preferred embodiment, the invention provides SMV proteins for use in a variety of applications, as outlined below. In some embodiments, an SMV protein can inhibit binding of an antibody, as described below, to SMV or a VLP. In some embodiments, an SMV protein can inhibit the binding of SMV or VLP to a host cell. In some embodiments, an SMV protein can induce an immune response that reacts with SMV, VLPs, and/or cells expressing SMV proteins, including VLPs. Thus an SMV protein can have one or more of the following characteristics: a) the ability to block binding of an antibody to SMV, a VLP, and/or cells expressing SMV proteins, including VLPs; b) the ability to block binding of SMV or VLP to a cell (e.g., a host cell or erythrocyte); c) the ability to induce an immune response, such as, an antibody response cross-reactive with SMV (particularly preferred), VLP, and/or SMV cells expressing SMV proteins, including VLPs; d) exhibiting at least one biological activity of a naturally-occurring SMV protein; or e) having at least the indicated homology. In a preferred embodiment, a SMV protein exhibits two or more of these characteristics. In a preferred embodiment, a SMV protein can be incorporated into a VLP. In addition, preferred embodiments include SMV proteins that share at least one antigenic epitope with a naturally occurring protein, although in some embodiments this many not be required.

Thus, in a preferred embodiment a "SMV protein" includes a protein that induces a SMV antibody that binds to an amino acid sequence deduced from a SMV nucleic acid. As known in the art, antibody recognizes either linear or conformational epitopes. By "epitope," "antigenic determinant," and grammatical equivalents herein are meant a region of an antigen or immunogen that is specifically bound by an antibody. Accordingly, an epitope can be linear or conformational.

By "linear epitope" herein is meant a epitope comprising a sequence of at least about 5 and not more than about 20 amino acids connected in a linear fashion, which amino acids, by themselves or as part of a larger sequence, bind to an antibody generated in response to such sequence. By "conformational epitope" is meant an epitope whose three dimensional or tertiary structure can be recognized by an antibody. Generally but not uniformly, amino acids that comprise a conformational epitope do not comprise a linear sequence of a protein's primary structure. Thus, a conformational epitope may be shared by proteins having non-homologous linear amino acid sequences. Therefore, a conformational epitope can be shared because the tertiary structure and the epitope contained therein recognized by an antibody can be shared between proteins that can have non-homologous primary structure. Thus, a SMV protein of the present invention includes proteins that mimic the conformational structure of a naturally occurring SMV protein such that it binds antibody produced in response to the naturally occurring SMV protein. A peptide or protein that mimics the conformational structure of a naturally occurring SMV protein is a mimotope. By "mimotope" and grammatical equivalents herein are meant a compound that mimics, resembles, copies, or imitates the structure of an epitope and induces, provokes, or reacts with the immune response to the epitope. For example, in some embodiments, a mimotope can be a protein mimotope that resembles, copies, or imitates the structure of the epitope. In some embodiments, a mimotope of a protein epitope can be a carbohydrate, a nucleic acid, an organic compound, or protein, or a derivative of any one of these. Mimotopes can be identified by various assays, including but not limited to screening a phage expression library, a cell expression library, a chemical library as known in the art.

In a preferred embodiment, an epitope can be unique; that is, antibodies generated to a unique epitope show insignificant or undetectable cross-reactivity to other proteins or epitopes. In an alternative embodiment, the epitope generates antibodies cross-reactive to proteins of related GII viruses or Noroviruses. For example, in some embodiments a SMV antibody binds to all members of a genogroup or genetic cluster. In other instances, antibodies can be made to multi-molecular assemblies of SMV proteins, such as, VLPs. In various exemplary embodiments, VLP specific antibodies can bind to conformation epitopes, epitopes formed by the interactions of VP1 and VP2 as they assemble into VLPs, or interactions of two or more VP1s, or interactions of two or more VP2s.

In a preferred embodiment, the SMV proteins can be SMV capsid proteins. In some embodiments, SMV capsid proteins can be VP1 and VP2 proteins assembled into VLPs. VLPs can be formed by recombinant expression of VP1 and VP2 proteins under conditions suitable for assembly. In some embodiments, conditions suitable for assembly can be provided by expression of VP1 and VP2 from a recombinant expression vector in a cell. Various suitable vectors include but are not limited to plasmids, baculovirus vectors, retrovirus vectors, adenovirus vectors, adeno-associated virus vectors, herpesvirus vectors, vaccinia virus vectors, SV50, M13, retrovirus vectors, yeast artificial chromosomes. Pfeifer et al., *Fields Virology Vol. I* (Knipe and Howley eds-in-chief, 4th Ed., Lippincott Williams and Wilkins 2001 (ISBN 0-7817-1832-5)). Preferably, VP1 and VP2 can be expressed in Sf9 cells by a recombinant baculovirus vector under conditions suitable for VLP assembly. In some embodiments, one capsid protein can be expressed and assembled into VLPs. Preferably, the one capsid protein can be VP1 that assembles into a VLP. In some embodiments, VP1 or VP2 proteins have an amino acid sequence that inhibits VLP assembly under conditions otherwise suitable for VLP assembly. In some embodiments, a SMV capsid protein can have an R residue at a position that corresponds to position 91 of SMV VP1 that inhibits VLP assembly.

Accordingly, included within the definition of SMV proteins of the present invention are amino acid sequence variants. These variants fall into one or more of three classes: substitutional, insertional or deletional variants. These variants ordinarily can be prepared by site specific mutagenesis of nucleotides in the DNA encoding a SMV protein, using cassette or PCR mutagenesis or other techniques well known in the art, to produce DNA encoding the variant, and thereafter expressing the DNA by recombinant methods, including those outlined above. However, variant SMV proteins having up to about 100-150 residues may be prepared by in vitro synthesis using established techniques. Amino acid sequence variants can be characterized by the predetermined nature of the variation, a feature that sets them apart from naturally occurring variation of the capsid protein amino acid sequence. The variants typically exhibit the same qualitative biological activity as the naturally occurring analogue, although variants can also be selected which have modified characteristics as will be more fully outlined below.

While the site or region for introducing an amino acid sequence variation can be predetermined, the mutation per se need not be predetermined. For example, in order to optimize the performance of a mutation at a given site, random mutagenesis may be conducted at the target codon or region and the expressed SMV protein variants screened for the optimal combination of desired activity. Techniques for making substitution mutations at predetermined sites in DNA having a known sequence are well known, for example, M13 primer mutagenesis and PCR mutagenesis. Screening of the mutants can be done using assays of capsid protein activities or properties.

Amino acid substitutions can be single residues; insertions usually will be on the order of from about 1 to about 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes can be done on a few amino acids to minimize the alteration of the molecule. However, larger changes may be tolerated in certain circumstances. When small alterations in the characteristics of the SMV protein are desired, substitutions generally can be made in accordance with the following chart:

CHART I

| Original Residue | Exemplary Substitutions |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity can be made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties can be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically can exhibit the same qualitative biological activity and can elicit the same immune response as the naturally-occurring analogue, although variants also can be selected to modify the characteristics of the SMV protein as needed. Alternatively, the variant may be designed such that the biological activity of the SMV protein is altered.

Covalent modifications of SMV proteins are included within the scope of this invention, particularly for screening assays or for uses as immunogens. One type of covalent modification includes reacting targeted amino acid residues of SMV protein with an organic derivatizing agent that is capable of reacting with selected side chains or the N- or C-terminal residues of a SMV protein. Derivatization with bifunctional agents is useful, for instance, for crosslinking SMV protein to a water-insoluble support matrix or surface for use in the methods described below, or for in vivo stability. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio] propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

In addition, modifications such as derivitization with polyethylene glycols (and other glycols) to increase the in vivo stability half-life can be also included.

SMV proteins of the present invention may also be modified in a way to form chimeric molecules comprising a SMV protein fused to another, heterologous polypeptide or amino acid sequence. In a preferred embodiment the SMV protein may be linked to adjuvants or other molecules to increase the immune response to the protein. In an additional embodiment, such a chimeric molecule comprises a fusion of a SMV protein with a tag polypeptide which provides an epitope to which an anti-tag antibody can selectively bind. The epitope tag generally can be placed at the amino- or carboxyl-terminus of the capsid polypeptide (or it may be added to the "new" C-terminus after the hydrophobic amino acid region, generally about 21 residues, is removed) or at an internal position. The presence of such epitope-tagged forms of a SMV protein can be detected using an antibody against the tag polypeptide. Also, provision of the epitope tag enables the SMV protein to be readily purified by affinity purification using an anti-tag antibody or another type of affinity matrix that binds to the epitope tag; this is also useful for binding the SMV protein to a support for heterogeneous screening methods. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)].

By "nucleic acid," "oligonucleotide," "polynucleotide", and grammatical equivalents herein are meant at least two nucleotides covalently linked together. A nucleic acid of the present invention will generally contain phosphodiester bonds, although in some cases, as outlined below, nucleic acid analogs can be included that may have alternate backbones, comprising, for example, phosphoramide (Beaucage et al., Tetrahedron 49(10): 1925 (1993.) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996). and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. As used herein, the term "nucleoside" includes nucleotides as well as nucleoside and nucleotide analogs, and modified nucleosides such as amino modified nucleosides. In addition, "nucleoside" includes non-naturally occurring analog structures. Thus for example the individual units of a peptide nucleic acid, each containing a base, are referred to herein as a nucleoside. Determining the suitable number and type of nucleotide acid analogs, non-naturally occurring nucleotides, including those with alternative backbones, and their position in a sequence is within the abilities of the skilled artisan.

By "SMV nucleic acid and grammatical equivalents herein are meant an isolated, recombinant or synthetic nucleic acid comprising a sequence homologous or identical or a reverse complement to the positive-sense genomic or full-length SMV RNA (vRNA) packaged into infectious virions. Thus, in various exemplary embodiments, an SMV nucleic acid can comprise a sequence homologous to SMV vRNA, the negative-sense reverse complement of SMV vRNA, or a subgenomic length SMV RNA, particularly SMVs that encode SMV proteins or fragments thereof. In various exemplary embodiments, an "SMV nucleic acid" can have an overall homology to the nucleotide sequences of SMV that is greater than about 75%, greater than about 80%, greater than about 85% and greater than 90%. In some embodiments the homology can be as high as about 93 to 95 to 98% to 100%. Homology in this context means sequence similarity or identity, with identity being preferred. Homology can be determined using standard techniques known in the art as described below and is dependent upon the nucleotide sequence of SMV. Thus in a preferred embodiment, an ORF1 SMV nucleic acid sequence is greater than 93% identical to SEQ ID NO:32, an ORF2 SMV nucleic acid sequence is greater than 98% identical to SEQ ID NO:30, and an ORF3 SMV nucleic acid sequence is greater than 98% identical to SEQ ID NO: 31. Thus, a SMV nucleic acid can encode an SMV protein, including but not limited to a SMV capsid protein. In various exemplary embodiments, a SMV nucleic acid can be about 8-100 nucleotides in length, about 8-40 nucleotides in length, or about 8 to 20 nucleotides in length. In some embodiments, a SMV nucleic acid can comprise from about 1%, 5%, 10%, 15%, 20%, 25%, 30%, 35%, 40%, 45%, 50%, 55%, 60%, 65%, 60%, 75%, 80%, 85%, 90%, 95%, to about 100% of the number of nucleic acids of full length SMV nucleic acid or a full-length SMV ORF.

As is known in the art, a number of different programs can be used to identify whether a protein or nucleic acid as discussed herein has sequence identity or similarity to a known sequence. Sequence identity and/or similarity value can be determined using standard techniques known in the art, including, but not limited to, the local sequence identity algorithm of Smith and Waterman, Adv. Appl. Math. 2:482 (1981), by the sequence identity alignment algorithm of Needleman & Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., Nucl. Acid Res. 12:387-395 (1984), preferably using the default settings, or by inspection. Preferably, percent identity can be calculated by FastDB based upon the following parameters: mismatch penalty of 1; gap penalty of 1; gap size penalty of 0.33; and joining penalty of 30, "Current Methods in Sequence Comparison and Analysis" in Macromolecule Sequencing and Synthesis, Selected Methods and Applications, pp 127-149, Alan R. Liss, Inc. (1988).

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng and Doolittle, J. Mol. Evol. 35:351-360 (1987); the method is similar to that described by Higgins and Sharp CABIOS 5:151-153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403-410, (1990) and Karlin et al., Proc. Natl. Acad. Sci. USA 90:5873-

5787 (1993). A particularly useful BLAST program is the WU-BLAST-2 program which was obtained from Altschul et al., Methods in Enzymology, 266: 460-480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389-3402. Gapped BLAST uses BLOSUM-62 substitution scores; threshold T parameter set to 9; the two-hit method to trigger ungapped extensions; charges gap lengths of k a cost of 10+k; Xu set to 16, and Xg set to 40 for database search stage and to 67 for the output stage of the algorithms. Gapped alignments are triggered by a score corresponding to ~22 bits.

A percent amino acid sequence identity value can be determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

The alignment may include the introduction of gaps in the sequences to be aligned. In addition, for sequences which contain either more or fewer amino acids or nucleotides than the amino acid or nucleotide sequences depicted in the drawings, it is understood that in one embodiment, the percentage of sequence identity can be determined based on the number of identical amino acids in relation to the total number of amino acids. Thus, for example, sequence identity of sequences shorter than that of the sequence depicted in the drawings can be determined using the number of residues in the shorter sequence. In percent identity calculations relative weight is not assigned to various manifestations of sequence variation, such as, insertions, deletions, substitutions, etc.

A percent amino acid or nucleic acid sequence identity can be determined by methods in which only identities are scored positively (+1) and all forms of sequence variation including gaps are assigned a value of "0", which obviates the need for a weighted scale or parameters for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

By "antibody" and grammatical equivalents herein are meant polyclonal and monoclonal antibody (mAb). Methods of preparation and isolation or purification of monoclonal and polyclonal antibodies are known in the art and e.g., are described in Harlow and Lane, Antibodies: A Laboratory Manual (New York: Cold Spring Harbor Laboratory Press, 1988). By "SMV antibody" and grammatical equivalents thereof include an antibody that binds to a SMV protein including fragments. The binding of a SMV antibody to an SMV protein preferably blocks or inhibits binding of another SMV antibody to a SMV. In some embodiments, a SMV antibody preferably inhibits binding of a SMV to a cell, e.g., a host cell (a cell permissive for SMV replication) or an erythrocyte. In some embodiments, a SMV antibody competes with another antibody for binding to a SMV or a SMV protein. In some embodiments SMV antibody inhibits or lessen SMV VLP binding to a host cell or VLP assembly.

In some embodiments, a SMV antibody binds to a SMV protein having a variant amino acid sequence, as described above. In a preferred embodiment, the antibody binds to a SMV protein having an R residue at an amino acid position that corresponds to position 91 of VP1 (SEQ ID NO:27). Thus, in a preferred embodiment, the a SMV protein can be H91R-VP1 protein.

SMV antibodies usually can be generated by immunization with a SMV protein having an amino acid sequence depicted in FIG. 6 or fragment thereof. In another embodiment, SMV proteins can be generated by immunization of a subject with SMV VLPs. In some embodiments, a subject can be an animal comprising an immune system that is capable of inducing an immune response to SMV or SMV proteins, including VLPs. Therefore, in some embodiments a subject can be a human.

When a SMV protein is used to generate SMV antibodies, the SMV protein shares at least one epitope or determinant with a full length SMV protein shown in FIG. 6. As known in the art, antibodies recognize either linear or conformational epitopes. By "epitope", "antigenic determinant", and grammatical equivalents herein are meant a region of an antigen or immunogen that can induce an immune response or can be specifically recognized (i.e., binds to) a molecular component of an immune response that functions in immune recognition (e.g., antibody, T-cell receptor, B-cell receptor). "Linear epitope" herein refers to an epitope comprising a sequence of at least about 5, 6, 7, 8, 9, 10, 11, 12, 13, 14, 15, 16, 17, 18, 19, or about 20 amino acids connected in a linear fashion, which amino acids, by themselves or as part of a larger sequence, can induce an immune response and/or can be recognized by the immune system, including immune effector mechanisms, as known in the art. "Conformational epitope" herein refers to an epitope comprising amino acids whose three dimensional or tertiary structure, alone or as part of a larger sequence, can induce an immune response or can be recognized by (e.g., binds to) a molecular component of an immune response that functions in immune recognition (e.g., T-cell receptor, B-cell receptor). The skilled artisan will appreciate that generally but not uniformly, amino acids that comprise a conformational epitope do not comprise a continuous, linear sequence of amino acid residues within a protein's primary structure. In some embodiments, a conformational epitope can comprise amino acid residues from two or more peptides. Therefore, in some embodiments a conformation epitope can be formed as a result of the molecular interactions that result in the formation of homo- or heteromultimers. Accordingly, epitopes or determinants may be linear or conformational as described herein. In most instances, antibodies made to a smaller SMV protein bind to the full length protein.

In some embodiments, an epitope can be unique, e.g., an epitope can induce an immune response characterized by statistically insignificant or no detectable cross-reactivity with other epitopes and/or peptides.

In some embodiments, an epitope can induce an immune response characterized by statistically significant cross-reactivity with another epitope and/or peptide. Therefore, in some embodiments, an epitope can be shared by peptides having statistically insignificant homology in their epitope amino acids. For example, in some embodiments, a conformational epitope can be shared by peptides having non-homologous amino acids because the tertiary structure of the peptides and a conformational epitope contained therein can be substantially similar. By "mimotope" and grammatical equivalents herein are meant a structure that mimics or resembles the structure of an epitope and induces or can be recognized by a product of an immune response to the epitope. In various exemplary embodiments, a mimotope can comprise a peptide, carbohydrate, a nucleic acid, an organic compound and/or a derivative or analog thereof. Mimotopes can be identified by various assays, including but not limited to screening a phage expression library, a cell expression library, a chemical library as known in the art.

Thus in some embodiments, an SMV epitope can produce an immune response (e.g., antibodies) that can be cross-reactive to proteins of other viruses. For example, in some embodiments a SMV antibody can binds to all members of a genogroup or genetic cluster. In other instances, antibodies can be made to multi-molecular assemblies of SMV proteins, such as, hetero- and homomultimers, and VLPs. Antibodies that are VLP specific preferably bind to conformation epitopes or epitopes formed by the intermolecular actions of VP1 and VP2 as they assemble into VLPs. However, VLP specific antibodies also can be linear epitopes.

The terms "antibody" and "SMV antibody," include isolated, recombinant, and synthetic antibody fragments and derivatives, as are known in the art, such as Fab, Fab', F(ab')2 or other antigen-binding subsequences of antibodies, such as, single chain antibodies (Fv for example), chimeric antibodies, etc., either produced by the modification of whole antibodies or those synthesized de novo using recombinant DNA technologies. The term "antibody" further comprises polyclonal antibodies and mAbs which can be agonist or antagonist antibodies, as well as antibodies that have been derivatized for example with PEG as known in the art, or variants as described herein.

In some embodiments, SMV antibodies of the invention specifically bind to SMV capsid proteins or to VLPs. By "specifically bind" herein is meant that the SMV antibodies have a binding constant in the range of at least $10^{-4}$ to at least about $10^{-6}$ $M^{-1}$, with a preferred range being at least about $10^{-7}$ to at least about $10^{-9}$ $M^{-1}$. Thus, in a preferred embodiments SMV antibodies can block the binding of a second antibody to SMV or block the binding of SMV to a cell (e.g., a cell permissive for SMV replication or erythrocyte). By "blocking," "inhibiting" and grammatical equivalents herein includes binding of SMV antibody to SMV reduces the amount of SMV that binds to a host cell or second antibody. In some embodiments, blocking occurs because the SMV antibody and the second antibody and host cell recognize the same epitope or region on a SMV protein. In some embodiments, blocking occurs because the SMV antibody and the second antibody or the SMV antibody and host cell recognize distinct but spatially related epitopes or regions on SMV. Thus, in a preferred embodiment, the inhibition can be competitive. In an alternative embodiment, the inhibition can be noncompetitive although this is generally not preferred. Generally, at least about 25% inhibition is preferred, with at least about 50% being particularly preferred and at least about a 95-100% inhibition being especially preferred.

In a preferred embodiment, an SMV protein of the present invention may be identified by its immunological activity, e.g., its ability to induce or bind to an SMV antibody specific for a linear or conformational epitope. The term "immunological activity" means the ability of an SMV protein to induce or cross react with an SMV antibody. Thus, for example, a protein can be an SMV protein, if it displays the immunological activity of a protein that is greater than 98% identical to an amino acid sequence depicted in FIG. 6. In an even more preferred embodiment, a protein is an SMV protein if it displays the immunological activity of a protein that is identical to an amino acid sequence depicted in FIG. 6.

In a preferred embodiment, SMV antibodies are provided. SMV antibodies may be polyclonal or monoclonal with the latter being preferred. In a preferred embodiment, SMV antibodies are specific for SMV VLPs (rSMV). In some embodiments, SMV antibodies SMV capsid proteins (VP1 or VP2 proteins or VLPs) can be capable of reducing or eliminating a biological function of SMV capsid proteins, as is described below. That is, the addition of SMV antibodies (either polyclonal or preferably monoclonal) to SMV (or cells containing SMV) may decrease or eliminate SMV infectivity, binding to a host cell, SMV assembly, or SMV yield. Generally, at least about a 25% decrease is preferred, with at least about 50% being particularly preferred and at least about a 95-100% decrease being especially preferred.

SMV monoclonal antibodies can be directed against a single antigenic site or a single determinant on an antigen. Thus SMV monoclonal antibodies, in contrast to polyclonal antibodies, which can be directed against multiple different epitopes, can be very specific. SMV monoclonal usually can be obtained from the supernatant of hybridoma culture (see Kohler and Milstein, Nature 256:495-7 (1975); Harlow and Lane, Antibodies: A Laboratory Manual (New York: Cold Spring Harbor Laboratory Press, 1988).

In a preferred embodiment, SMV antibodies can be humanized. Using current monoclonal antibody technology one can produce a humanized antibody to virtually any target antigen that can be identified [Stein, Trends Biotechnol. 15:88-90 (1997)]. Humanized forms of non-human (e.g., murine) antibodies can be chimeric molecules of immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient can be replaced by residues from a CDR of a non-human species (donor antibody) such as mouse, rat or rabbit having the desired specificity, affinity and capacity. In some instances, Fv framework residues of the human immunoglobulin can be replaced by corresponding non-human residues. Humanized antibodies may also comprise residues which can be found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions can be those of a human immunoglobulin consensus sequence. The humanized antibody optimally also will comprise at least a portion of an immunoglobulin constant region (Fc), typically that of a human immunoglobulin [Jones et al., Nature 321:522-525 (1986); Riechmann et al., Nature 332:323-329 (1988); and Presta, Curr. Op. Struct. Biol. 2:593-596 (1992)].

Methods for humanizing non-human antibodies can be well known in the art. Generally, a humanized antibody has one or more amino acid residues introduced into it from a source which is non-human. These non-human amino acid residues can be often referred to as import residues, which can be typically taken from an import variable domain. Humanization can be essentially performed following the method of Winter and co-workers [Jones et al., supra; Riechmann et al., supra; and Verhoeyen et al., Science, 239:1534-1536 (1988)], by substituting rodent CDRs or CDR sequences for the corresponding sequences of a human antibody. Additional examples of humanized murine monoclonal antibodies are also known in the art, e.g., antibodies binding human protein C [O'Connor et al., Protein Eng. 11:321-8 (1998)], interleukin 2 receptor [Queen et al., Proc. Natl. Acad. Sci., U.S.A. 86:10029-33 (1989]), and human epidermal growth factor receptor 2 [Carter et al., Proc. Natl. Acad. Sci. U.S.A. 89:4285-9 (1992)]. Accordingly, such humanized antibodies can be chimeric antibodies (U.S. Pat. No. 4,816,567), wherein substantially less than an intact human variable domain has been substituted by the corresponding sequence from a non-human species. In practice, humanized antibodies can be typically human antibodies in which some CDR residues and possibly some FR residues can be substituted by residues from analogous sites in rodent antibodies.

Human antibodies can also be produced using various techniques known in the art, including phage display libraries [Hoogenboom and Winter, J. Mol. Biol. 227:381 (1991); Marks et al., J. Mol. Biol. 222:581 (1991)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol. 147(1):86-95 (1991)]. Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10:779-783 (1992); Lonberg et al. Nature 368:856-859 (1994); Morrison, Nature 368:812-13 (1994); Fishwild et al., Nature Biotechnology 14:845-51 (1996); Neuberger, Nature Biotechnology 14:826 (1996); Lonberg and Huszar, Intern. Rev. Immunol. 13:65-93 (1995).

Once made, the SMV compositions of the invention (e.g. SMV antibodies, SMV proteins, and SMV nucleic acids) find use in a number of applications. In general, SMV antibodies and SMV proteins find use in inhibiting the interaction of SMV VLPs with cells. Thus, the compositions find use in diagnostic assays and kits to detect the presence of SMV and other Noroviruses in a subject (e.g., patient) or sample. Furthermore, the compositions of the invention can be used to discover additional antibodies and proteins which compete for binding with SMV compositions; thus, screening assays, generally but not always competitive screening assays, particularly high throughput screening assays, are also provided. For example, an SMV component of the invention may be attached to a solid support and binding components can be evaluated.

In a preferred embodiment, SMV proteins of the present invention find use as immunogens. By "immunogen" herein is meant a compound suitable for inducing an immune response in a subject. In some embodiments, an immunogen can be an SMV immunogen which as used herein can comprise one or more SMV proteins, including but not limited to an SMV VLPs. In some embodiments, a SMV immunogen can be a SMV peptide, including immunogenic fragments thereof or VLPs. In various exemplary embodiments, an SMV VLP can comprise VP1 alone or VP1 and VP2.

"Immune system" and grammatical equivalents herein refer a system of cellular and molecular components that can function to distinguish self from non-self and can function as a defense against transformed cells (e.g., benign and malignant tumors, cancer cells and the like), foreign organisms, and substances. The components of the immune system can include cells, such as, leukocytes, lymphocytes (e.g., T-cell (e.g. Th1, Th2, TR1. $T_K$, NK cells), B-cells), macrophages, antigen presenting cells (APC), granulocytes (e.g., neutrophils, eosinophils, basophils, mast cells), monocytes, dendritic cells, M cells, epithelium (e.g., surface epithelium), and the like. Components of the immune system can include secreted molecules, such as, immunoglobulin (antibody, e.g., IgA, secretory IgA, IgM, IgG, IgE and the like), cytokines (e.g., Type I cytokines, interferons (Type II cytokines), interleukins, chemokines, and the like), tumor necrosis factors (e.g. TNF 1-19), the complement system, lysozyme, chitinases, phospholipase (e.g., phospholipase A2), bactericidal permeability-increasing protein (BPI), defensins, cathelicidins, serprocedins, lactoferrin and the like (see, e.g., Fundamental Immunology 1-1701 (Paul, ed., 5th ed., Lippincott Williams & Wilkins 2003 (ISBN 0-7817-3514-9))). Other components of the immune system can include, but are not limited to, major histocompatibility antigens, T-cell receptors, B-cell receptors, CD antigens, pattern recognition receptors (PRRs), secreted pattern recognition receptors (PRMs), toll-like receptors (TLRs, e.g., TLR1, 2, 3, 4, 5, 6, 7, 8, 9, 10), and the like. (Fundamental Immunology 1-1701 (Paul, ed., 5th ed., Lippincott Williams & Wilkins 2003 (ISBN 0-7817-3514-9)); Goodman and Gilman's The Pharmacological Basis of Therapeutics 1463-1486 (Hardman et al., ed., 10th ed., McGraw-Hill 2001 (ISBN 0-07-112432-2)))

The skilled artisan will appreciate that the immune system generally is capable of producing an innate immune response and an adaptive immune response. (Fundamental Immunology 497-523, 561-565, 816-819 (Paul, ed., 5th ed., Lippincott Williams & Wilkins 2003 (ISBN 0-7817-3514-9)); Goodman and Gilman's The Pharmacological Basis of Therapeutics 1463-1486 (Hardman et al., ed., 10th ed., McGraw-Hill 2001 (ISBN 0-07-112432-2)); Roitt et al. Immunology 1.1-1.10, 2.8, 9.1-9.13, 13.3, 15.1-15.9, 18.6-18.8, 16.2-16.5 (2d ed. Gower Medical Publishing 1989)) An innate immune response generally can be characterized as not being substantially antigen specific and/or not generating immune memory. (Fundamental Immunology 497-518 (Paul, ed., 5th ed., Lippincott Williams & Wilkins 2003 (ISBN 0-7817-3514-9)); Goodman and Gilman's The Pharmacological Basis of Therapeutics 1463-1486 (Hardman et al., ed., 10th ed., McGraw-Hill 2001 (ISBN 0-07-112432-2)); Roitt et al. Immunology 1.1-1.10 (2d ed. Gower Medical Publishing 1989)) In contrast, an adaptive immune response can be characterized as being substantially antigen specific, maturing over time (e.g., increasing affinity and/or avidity for antigen), and in general can produce immunologic memory. Even though these and other functional distinctions between innate and adaptive immunity can be discerned, the skilled artisan will appreciate that the innate and adaptive immune systems can be integrated and therefore can act in concert. (Fundamental Immunology 512-513 (Paul, ed., 5th ed., Lippincott Williams & Wilkins 2003 (ISBN 0-7817-3514-9)); Goodman and Gilman's The Pharmacological Basis of Therapeutics 1463-1486 (Hardman et al., ed., 10th ed., McGraw-Hill 2001 (ISBN 0-07-112432-2)); Roitt et al. Immunology 1.10 (2d ed. Gower Medical Publishing 1989)) Therefore, the induction of an innate immune response can lead to an adaptive immune response and vice versa.

"Immune response to SMV" as used herein refers to a response of the immune system to one or more SMV antigens (e.g., VLP). In various exemplary embodiments, an immune response to an SMV can be an innate and/or adaptive response. In some embodiments, an adaptive immune response can be a "primary immune response" which as used herein refers to an immune response occurring on the first exposure of a "naïve" subject to an antigen. For example, in the case of a primary antibody response, after a lag or latent period of from approximately 3 to 14 days depending on, for example, the antigen, dose, and subject, antibodies to an SMV antigen can be produced. Generally, IgM production lasts for several days followed by IgG production and the IgM response can decrease. Antibody production can terminate after several weeks but memory cells can be produced. In some embodiments, an adaptive immune response can be a "secondary immune response", "anamnestic response," or "booster response" which as used herein refer to the immune response occurring on a second and subsequent exposure of a subject to an antigen. Generally, in a secondary immune response, memory cells respond to the antigen and therefore the secondary immune response can differ from a primary immune response qualitatively and/or quantitatively. For example, in comparison to a primary antibody response, the lag period of a secondary antibody response can be shorter, the peak antibody titer can be higher, higher affinity antibody can be produced, and/or antibody can persist for a greater period of time.

In some embodiments, an immune response can be a "B-cell response" or "antibody response", which as used herein refer to a change quantitatively or qualitatively in the immunoglobulins that are produced as a result of the administration of an immunogen. In a preferred embodiments, the affinity and quantity of immunoglobulins increases as a result of the administration of an SMV antigen to a subject. As known in the art, antibodies or immunoglobulins can be of various classes, isotypes, and subtypes, depending on the species of the subject producing the antibodies. Various types of antibodies are known in the art and can include but are not limited to IgG, IgM, IgA, sIgA, and the like.

In some embodiments, an immune response to an SMV antigen can react with SMV or cells expressing SMV proteins. Thus, the skilled artisan will appreciate that in some embodiments, an immune response to a SMV antigen can react with the causative agent of SMV disease and/or a protein produced by SMV The administration of an SMV protein (e.g., SMV VLP) as an immunogen can be done in a variety of ways, e.g., parenteraly or mucosally, e.g., oral, nasal, rectal. Generally, the SMV proteins can be formulated according to known methods to prepare useful compositions, whereby immunogenic amounts of SMV protein can be combined in admixture with a carrier or vehicle. Suitable vehicles and their formulation are well known in the art. Such compositions contain immunogenic amounts of SMV protein together with a suitable amount of vehicle. The composition may include salts, buffers, carrier proteins such as serum albumin, targeting molecules to localize SMV proteins, such as VLP, at the appropriate site or tissue within a subject, and other molecules. The composition may include adjuvants as well. The formulation cam be chosen at the discretion of the practitioner and can be dependent on the route of immunization, age and immune status of the patient.

"SMV antigen" and grammatical equivalents as used herein refer to an antigen suitable for inducing an immune response to SMV or being recognized by a product of an immune response (e.g., antibody). Therefore, in some embodiments, a SMV antigen can be a SMV immunogen. In some embodiments, a SMV antigen can be a SMV peptide, such as a VLP and immunogenic fragments thereof or VLPs. In various exemplary embodiments, an SMV VLP can comprise VP1 alone (VP1-VLP) or VP1 and VP2.

In some embodiments, SMV antigens, including immunogens, can be formulated with an adjuvant. "Adjuvant" as used herein refers to a non-toxic agent that can stimulate the immune system, thereby, enhancing, either quantitatively and/or qualitatively, the response to a SMV antigen, such as, VLPs. In some embodiments, an adjuvant can be suitable for administration to various subjects. In some embodiments, an adjuvant can be suitable for inducing an immune response in a non-human subject. In some embodiments, an adjuvant can be suitable for inducing an immune response in a human subject. By "suitable for use in a human subject" herein is meant an adjuvant that can be well tolerated by a human subject (e.g., infant, child, adolescent, adult, or the elderly). Therefore, excluded from adjuvants suitable for human use are toxins, (e.g., cholera toxin (CT)). However, the skilled artisan will appreciate that non-toxic components of toxins (e.g., CT-B) can be suitable for human use. In a preferred embodiment, an adjuvant can comprise a plurality of adjuvants. In various exemplary embodiments, an adjuvant can be Freunds adjuvant, such as, Freunds complete and Freunds incomplete adjuvant. In some embodiments, an adjuvant can be a mucosal adjuvant. By "mucosal adjuvant" herein is meant an adjuvant suitable for use at the mucosal membrane of a subject. In some embodiments, a mucosal adjuvant can be an isolated extract comprising a protein or lipid of a gram-negative bacterial cell well or outer layer. Therefore, in some embodiments, a mucosal adjuvant can be an invasin protein. Invasin proteins and methods of use are described in U.S. Pat. Nos. 6,245,892, 6,277,379, 6,680,374, and PCT Publication No. WO02/094190, all four of which are expressly incorporated by reference in their entirety. An invasion protein from a gram-negative bacteria preferably finds use as a mucosal adjuvant to induce a mucosal immune response to SMV antigens, such as, sIgA.

Where sustained-release administration of an SMV antigen, such as VLP, microencapsulation can be contemplated. Microencapsulation of recombinant proteins for sustained release has been successfully performed with human growth hormone (rhGH), interferon- (rhIFN-), interleukin-2, and MN rgp120. Johnson et al., Nat. Med., 2:795-799 (1996); Yasuda, Biomed. Ther., 27:1221-1223 (1993); Hora et al., Bio/Technology, 8:755-758 (1990); Cleland, "Design and Production of Single Immunization Vaccines Using Polylactide Polyglycolide Microsphere Systems," in Vaccine Design: The Subunit and Adjuvant Approach, Powell and Newman, eds, (Plenum Press: New York, 1995), pp. 439-462; WO 97/03692, WO 96/40072, WO 96/07399; and U.S. Pat. No. 5,654,010. The sustained-release formulations of polypeptides were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), Biodegradable Polymers as Drug Delivery Systems (Marcel Dekker: New York, 1990), pp. 141.

SMV proteins, including VLPs, can be administered in various formulations and in various amounts depending on factors including but not limited to the age, mass, immune status, route of immunization, and health of a subject. In some embodiments, an SMV protein can be administered to a human or non-human subject in a range from about 40 to about 200 μg peptide/dose. In various exemplary embodiments, the dose administered to a subject can be from about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, to about 250 μg peptide/dose, with higher and lower doses that can be contemplated. In some embodiments, a dose administered to a subject can be from about 1, 2, 3, 4, 5, 6, 7, 8, 9, to about 10, 15, 20, 30, 40, 50, 60, 70, 80, 90, to about 100 μg/kg body mass, with higher and lower doses than can be contemplate. The number of doses that can be administered as a function of time can be from about 1, 2, or about 3 doses over 1, 2, 3, or about 4 weeks but can be increased or decreased depending at least in part on the immune status of a subject.

"Acceptable salt" refers to a salt of a compound of the invention which is made with counterions and is understood in the art to be generally acceptable for immunogenic uses and which possesses the desired immunogenic activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, morpholine, piperidine, dimethylamine, diethylamine and the like. Also included are salts of amino acids such as arginates and the like, and salts of organic acids like glucuronic or galacturonic acids and the like (see, e.g., Berge et al., 1977, J. Pharm. Sci. 66:1-19).

"Acceptable vehicle", "effective carrier", and grammatical equivalents refer to a diluent, adjuvant, excipient, surfactant, preservative, stabilizer, chelating agent or the like with which a SMV protein, including VLPs, can be administered to a subject to induce an immune response, as will be appreciated by those skilled in the art of such formulations (U.S. Pat. No. 6,403,597) A wide variety of suitable immunogenic compositions are described, for example, in Remington's Pharmaceutical Sciences, 20th ed. 2001.

Formulations suitable for oral administration can comprise (a) liquid solutions, such as an effective amount of the active compound suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Suitable nasal formulations can be administered as a spray, drop, suspension, gel and the like. Formulations suitable for nasal administration may include any one or more of preservatives (e.g., benzyl alcohol, parabens, thimerosal, chlorobutanol, benzalkonium), surfactants, co-solvents, adhesives, antioxidants (e.g., about 0.01% to about 5% by weight, sodium metabisulfite, postassium metabisulfite, ascorbyl palmitate), buffers, viscosity and absorption enhancing agents, humectant, and agents to adjust pH and osmolarity. Nasal formulations can be aqueous or non-aqueous solutions, such as, liposomes, emulsions, and microemulsions. Thickening agents can be used to provide a desired viscosity such as methyl cellulose, xanthan gum, carboxymethyl cellulose, hydroxypropyl cellulose, carbomer, polyvinyl alcohol, alginates, acacia, and combinations thereof. The concentration of a thickening agent can be determined by one skilled in the art but generally can be from about 0.01% to about 20% by weight of the formulation. Absoprtion enhances can optionally be used to increase absorption of an SMV protein, including VLPs. Absorption enhances include but are not limited to sodium lauryl sulfate, sodium salicylate, oleic acid, lecithin, dehydrated alcohol, Tween (e.g., Tween 20, 40, 60, 80 and the like), Span (e.g., Span 20, 40, 80 and the like), polyosyl 40 stearate, polyoxy ethylene 50 stearate, edetate disodium, propylene glycol, glycerol monooleate, bile salts, octoxynol, and combinations thereof. Absorption enhances generally can be used at a concentration from about 0.01% to about 25% by weight of the total formulation.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, subcutaneous administration and intravenous administration are the preferred methods of administration. A specific example of a suitable solution formulation may comprise from about 0.5-100 mg/ml SMV antigen and about 1000 mg/ml propylene glycol in water. Another specific example of a suitable solution formulation may comprise from about 0.5-100 mg/ml SMV antigen and from about 800-1000 mg/ml polyethylene glycol 400 (PEG 400) in water.

A specific example of a suitable suspension formulation may include from about 0.5-30 mg/ml SMV antigen and one or more excipients selected from the group consisting of: about 200 mg/ml ethanol, about 1000 mg/ml vegetable oil (e.g., corn oil), about 600-1000 mg/ml fruit juice (e.g., grapefruit juice), about 400-800 mg/ml milk, about 0.1 mg/ml carboxymethylcellulose (or microcrystalline cellulose), about 0.5 mg/ml benzyl alcohol (or a combination of benzyl alcohol and benzalkonium chloride) and about 40-50 mM buffer, pH 7 (e.g., phosphate buffer, acetate buffer or citrate buffer or, alternatively 5% dextrose may be used in place of the buffer) in water.

A specific example of a suitable liposome suspension formulation may comprise from about 0.5-30 mg/ml compound, about 100-200 mg/ml lecithin (or other phospholipid or mixture of phospholipids) and optionally about 5 mg/ml cholesterol in water. For subcutaneous administration, a liposome suspension formulation including 5 mg/ml compound in water with 100 mg/ml lecithin and 5 mg/ml compound in water with 100 mg/ml lecithin and 5 mg/ml cholesterol provides good results.

The formulations of compounds can be presented in unit-dose or multi-dose sealed containers, such as ampules and vials. Injection solutions and suspensions can be prepared from sterile powders, granules, and tablets of the kind previously described. In some embodiments, the disclosed compositions (e.g., SMV antigens, SMV peptides, and SMV VLPs) and formulations can be packaged in kits for administration to a subject, e.g., a container, preferably sealed, for storage prior to use and instructions for carrying out administration suitable for inducing an immune response to SMV. For example, in some embodiments, a formulation can be suitable for administration to a mucosal surface and therefore can contain one or more unit doses of a SMV immunogen, SMV VLP, SMV antibody. In some embodiments, a formulation can be suitable for parenteral administration and therefore can contain a one or more unit doses. In some embodiments, a kit can include a device suitable for administrating one or more of the disclosed compositions, including unit doses. Thus, in some embodiments, a kit can contain multiple formulations for administration via various devices, including but not limited to, droppers, swabs, aerosolizers, nebulizers, sufflators, inhalers, syringes, needles, dermal patches, and the like.

The preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials, sufflators, or ampoules. Also, the unit dosage form can be a capsule, tablet, cachet, or lozenge itself, or it can be the appropriate number of any of these in packaged form. The composition can, if desired, also contain other compatible agents, discussed in more detail, below.

The present invention further provides methods of blocking SMV antibody binding to a SMV. In some embodiments, an unlabelled SMV antibody binds a SMV and blocks the binding of a labeled antibody. In an alternative embodiment, a labeled SMV antibody is inhibited from binding to a SMV by an unlabeled antibody. The percent inhibition can be calculated by the decrease of labeled-antibody binding in the presence of unlabeled antibody. The present invention further provides methods of blocking SMV antibody binding to a SMV by use of an SMV protein. In a preferred embodiment, a labeled SMV antibody binds an SMV protein which blocks the binding of the SMV antibody to a SMV. The percent inhibition can be calculated by the decrease of SMV antibody binding in the presence as compared to the absence of the SMV protein. The present invention further provides method of blocking SMV binding to a host cell.

Once made, SMV nucleic acids find use in probe based hybridization assays. Sequence specific nucleic acid hybridization is fundamental to molecular biological processes. Probe-based assays that exploit sequence-specific hybridization can be used in many applications such as detecting, analyzing, quantifying and/or locating SMV nucleic acids. For example, probe-base hybridization can be employed to quantify SMV gene expression levels, to detect single nucleotide polymorphisms (SNP) and/or other genetic mutations, as well as to type, map and/or fingerprint gene variation in nucleotide sequences. Thus, SMV nucleic acid probe-base hybridization can be applied to SMV identification as well as to numerous other applications. If the SMV nucleic acid is isolated from a sample, the sample containing the SMV nucleic acid can be provided from nature or it can be synthesized or supplied from a manufacturing process. For example, SMV nucleic acid can be analyzed by an amplification process, contained in a cell or organism, or otherwise be extracted from a cell or virion. Examples of amplification processes that can be the source for the target sequence include, but are not limited to, Polymerase Chain Reaction (PCR), Ligase Chain Reaction (LCR), Strand Displacement Amplification (SDA; see, e.g., Walker et al., 1989, PNAS 89:392-396; Walker et al., 1992, Nucl. Acids Res. 20(7): 1691-1696; Nadeau et al., 1999, Anal. Biochem. 276(2):177-187; and U.S. Pat. Nos. 5,270,184, 5,422,252, 5,455,166 and 5,470,723), Transcription-Mediated Amplification (TMA), Q-beta replicase amplification (Q-beta), Rolling Circle Amplification (RCA), Lizardi, 1998, Nat. Genetics 19(3): 225-232 and U.S. Pat. No. 5,854,033), or Asynchronous PCR (see, e.g., WO 01/94638), all of which are incorporated by reference.

In another embodiment, probe based hybridization assays utilize an SMV nucleic acid attached to a solid support or carrier. In a preferred embodiment an array of SMV nucleic acids can be attached to a solid support of carrier. "Solid support" or "solid carrier" refers to any solid phase material upon which an SMV nucleic acid is synthesized, attached, ligated or otherwise immobilized. Solid support encompasses terms such as "resin", "solid phase", "surface" and "support". A solid support may be composed of organic polymers such as polystyrene, polyethylene, polypropylene, polyfluoroethylene, polyethyleneoxy, and polyacrylamide, as well as copolymers and grafts thereof. A solid support may also be inorganic, such as glass, silica, controlled-pore-glass (CPG), or reverse-phase silica. The configuration of a solid support may be in the form of beads, spheres, particles, granules, a gel, or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

"Support bound" means immobilized on or to a solid support. It is understood that immobilization can occur by any means, including for example; by covalent attachment, by electrostatic immobilization, by attachment through a ligand/ligand interaction, by contact or by depositing on the surface.

"Array" or "microarray" refers a predetermined spatial arrangement of oligomers present on a solid support or in an arrangement of vessels. Certain array formats can be referred to as a "chip" or "biochip" (M. Schena, Ed. Microarray Biochip Technology, BioTechnique Books, Eaton Publishing, Natick, Mass. (2000). An array can comprise a low-density number of locations, e.g. 2 to about 12, medium-density, e.g. about a hundred or more locations, or a high-density number, e.g. a thousand or more. Typically, the array format is a geometrically regular shape that allows for fabrication, handling, placement, stacking, reagent introduction, detection, and/or storage. The array may be configured in a row and column format, with regular spacing between each location. Alternatively, the locations may be bundled, mixed or homogeneously blended for equalized treatment or sampling. An array may comprise a plurality of addressable locations configured so that each location is spatially addressable for high-throughput handling, robotic delivery, masking, or sampling of reagents, or by detection means including scanning by laser illumination and confocal or deflective light gathering.

A compound, such as a SMV antibody, SMV protein, SMV nucleic acid, SMV VLP can be directly or indirectly conjugated to a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. Preferred labels include, but are not limited to, fluorescent labels, label enzymes and radioisotopes.

In general, labels fall into four classes: a) isotopic labels, which may be radioactive or heavy isotopes; b) magnetic, electrical, thermal labels; c) colored or luminescent dyes or moieties; and d) binding partners. Labels can also include enzymes (horseradish peroxidase, etc.) and magnetic particles. In a preferred embodiment, the detection label is a primary label. A primary label is one that can be directly detected, such as a fluorophore.

Preferred labels include chromophores or phosphors but are preferably fluorescent dyes or moieties. Fluorophores can be either "small molecule" fluores, or proteinaceous fluores.

By "fluorescent label" is meant any molecule that may be detected via its inherent fluorescent properties. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade BlueJ, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., Science 263 (5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12): 5408-5417 (1993)), β-galactosidase (Nolan, et al., Proc Natl Acad Sci USA 85(8):2603-2607 (April 1988)) and *Renilla* WO 92/15673; WO 95/07463; WO 98/14605; WO 98/26277; WO 99/49019; U.S. Pat. No. 5,292,658; U.S. Pat. No. 5,418, 155; U.S. Pat. No. 5,683,888; U.S. Pat. No. 5,741,668; U.S. Pat. No. 5,777,079; U.S. Pat. No. 5,804,387; U.S. Pat. No. 5,874,304; U.S. Pat. No. 5,876,995; and U.S. Pat. No. 5,925, 558). All of the above-cited references are expressly incorporated herein by reference.

Particularly preferred labels for use in the present invention include: Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC can be found at drmr.com/abcon Quantitation of fluorescent probe conjugation may be assessed to determine degree of labeling and protocols including dye spectral properties can be found at metazoa.com/UPL3419.

In another preferred embodiment, the fluorescent label is a GFP and, more preferably, a *renilla, ptilosarcus*, or *aequorea* species of GFP.

In a preferred embodiment, a secondary detectable label is used. A secondary label is one that is indirectly detected; for example, a secondary label can bind or react with a primary label for detection, can act on an additional product to generate a primary label (e.g. enzymes), etc. Secondary labels include, but are not limited to, one of a binding partner pair; chemically modifiable moieties; nuclease inhibitors, enzymes such as horseradish peroxidase, alkaline phosphatases, lucifierases, etc.

In a preferred embodiment, the secondary label is a binding partner pair. For example, the label may be a hapten or antigen, which will bind its binding partner. For example, suitable binding partner pairs include, but are not limited to: antigens (such as proteins (including peptides) and small molecules) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. Preferred binding partner pairs include, but are not limited to, biotin (or imino-biotin) and streptavidin, digoxinin and Abs, and ProlinxJ reagents (see www.prolinxinc.com/ie4/home.hmtl).

In a preferred embodiment, the binding partner pair comprises an antigen and an antibody that will specifically bind to the antigen. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$-$10^{-6}$ $M^{-1}$, with less than about $10^{-5}$ to $10^{-9}$ $M^{-1}$ being preferred and less than about $10^{-7}$-$10^{-9}$ $M^{-1}$ being particularly preferred.

In a preferred embodiment, the secondary label can be a chemically modifiable moiety. In this embodiment, labels comprising reactive functional groups are incorporated into the molecule to be labeled. The functional group can then be subsequently labeled (e.g. either before or after the assay) with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo- or hetero-bifunctional linkers as are well known (see 1994 Pierce Chemical Company catalog, technical section on cross-linkers, pages 155-200, incorporated herein by reference). The type of label is chosen at the discretion of the practitioner and includes, for example, enzymatic, radioactive, and fluorescent labels. (see Haugland. Handbook of Fluorescent Probes and Research Chemicals. $6^{th}$ ed. Molecular Probes, Eugene, Oreg.).

The present invention further provides kits for use within any of the above compositions and methods. Such kits typically comprise two or more components necessary for performing a diagnostic assay. Components may be compounds, reagents, containers and/or equipment. For example, one container within a kit may contain an isolated SMV antibody that specifically binds to a SMV and finds use in the identification of a SMV isolate from a clinical samples. Such antibodies may be provided attached to a label, as described above. One or more additional containers may enclose elements, such as reagents or buffers, to be used in the assay. Such kits may also, or alternatively, contain a detection reagent as described above that contains a reporter group suitable for direct or indirect detection of antibody binding. Alternatively, a kit may be designed to detect SMV antibody in a biological sample, such feces or serum. Such kits generally comprise at least one SMV protein, including VLPs, as described above, that binds to SMV antibody. Such a SMV protein finds use, for example, in the detection of SMV antibody in a clinical sample. Alternatively, a kit is designed to detect SMV nucleic acid in a biological sample, such as feces or serum. Such kits generally comprise at least one SMV nucleotide or probe, as described above, that binds to an SMV nucleic acid in a clinical sample. In some embodiments, a kit can comprise any one or more of the compositions described herein in a container and with instructions for use.

While the present teachings are described in connection with various embodiments, it is not intended that the present teachings be limited to such embodiments. Rather, the present teachings encompass various alternatives, modification, and equivalents, as will be appreciated by those skilled in the art.

Aspects of the present disclosure may be further understood in view of the following examples, which should not be construed as limiting the scope of the present disclosure in any way. All references cited herein are expressly incorporated by reference in their entirety for any purpose. If an expressly incorporated reference differs from or contradicts the present application, including but not limited to defined terms, term usage, described techniques, or the like, this application controls.

EXAMPLES

Example 1

Viral RNA Extraction

A stool sample from a SMV-infected volunteer diluted in phosphate-buffered saline (PBS) was extracted essentially as described with modifications. (Wang et al. J Virol. 1994 September; 68(9):5982-90.) One hundred microliters of a 20% suspension in PBS was extracted with Vertrel XF (Dupont) and virus particles per precipitated with 8% PEG (MW 8000) and 0.4 M NaCl. (Mendez et al. J Virol Methods. 2000 October; 90(1):59-67.) Precipitated virus particles were digested with 400 μg/ml proteinase K, and virus RNA (vRNA) then was precipitated with cetyltrimethylammonium bromide (CTAB) in the presence of 2 M NaCl. Further purification and concentration of the vRNA was achieved by phenol/chloroform extraction, followed by chloroform extraction, and finally precipitation with 0.2 M sodium acetate and 2.5 volumes of ethanol. The vRNA pellet was suspended in ribonuclease free water for injection (WFI) and stored at −20° C.

Example 2

Cloning and Sequencing

SMV cDNA was amplified by RT-PCR from the purified vRNA template with AMV-RT (Promega, Madison, Wis.) and specifically designed oligonucleotide primers (Integrated DNA Technologies, Coralville, Iowa). cDNAs covering the complete genome of SMV were obtained in a total of six PCR fragments with the primers listed in Table 1. The locations of the primers on the genome are indicated in FIG. 1. Primers used to amplify SMV ORF1 were designed from conserved regions of three aligned calicivirus sequences: NV (Genbank Acc. No. M87661), LV (X86557), and CV (AF145896). SMV OFR2 primers were designed from SMV capsid sequence (U75682), and ORF3 primers were designed from the closely related (94% nt identity) MeV ORF3 sequence (X81879). The 3' end of SMV was amplified with an oligo dT primer and primer SMV7 (SEQ ID NO:11). Viral template (0.5 μl) and 2.5 μM of each downstream primer were combined and incubated for 5 minutes at 70° C. then cooled on ice. An RT reaction consisting of 1×PCR Buffer (10 mM KCl, 10 mM $(NH_4)2SO_4$, 20 mM Tris-HCl (pH 8.75), 2 mM $MgSO_4$, 0.1% Triton X-100, 0.1 mg/ml BSA), 1.25 mM dNTPs, 40 U Rnasin (Promega), and IOU AMV-RT (Promega) were mixed in a 20 μl reaction and reverse transcribed for 1 h at 45° C. The reaction was heated for 10 min at 70° C. to inactivate the RT. The 20 μl RT reaction was brought to 100 μl with WFI, 8.0 μl 10×PCR buffer (100 mM KCl, 100 mM (NH4)2SO4, 200 mM Tris-HCl (pH 8.5), 20 mM $MgSO_4$, 1% Triton X-100, 1 mg/ml BSA), 0.5 μM (+) sense primer and 2.5 U of Pfu Turbo DNA polymerase (Stratagene, La Jolla, Calif.). PCR conditions consisted of an initial 3 min denaturation at 94° C. followed by 30 cycles of 94° C. for 45", 55° C. for 50", 72° C. for 1 min/kb, and a final 15 min extension for 72° C. PCR products were visualized by agarose gel electrophoresis and ethidium bromide staining. The cDNA fragments were 3' adenylated with Taq polymerase (Promega, Madison, Wis.) and either directly cloned into the pCR2.1 TOPO vector (Invitrogen, Carlsbad, Calif.) or gel purified prior to cloning.

TABLE 1

Primers for RT-PCR of SMV cDNA

| Name | nt | Sense | Sequence | Identifier |
|---|---|---|---|---|
| SMV 10 | 3 | Plus | 5'-gaatgaagatggcgtctaacg-3'[a] | SEQ ID NO:1 |
| SMV 12 | 1000 | Plus | 5'-gggcctgaggaccttgc-3'[a] | SEQ ID NO:2 |
| SMV 11 | 1325 | Minus | 5'-cttcctggctttctcctcctc-3'[a] | SEQ ID NO:3 |
| SMV 14 | 1720 | Minus | 5'-gacaggatcgagaacaaagg-3'[a] | SEQ ID NO:4 |
| SMV 13 | 1980 | Minus | 5'-gaagccaccctgtggagccag-3'[a] | SEQ ID NO:5 |
| SMV 16 | 3000 | Plus | 5'-ggagtgttgactacaatgag-3'[a] | SEQ ID NO:6 |
| SMV 17 | 4100 | Minus | 5'-ccagagaagcctcttctt-3'[a] | SEQ ID NO:7 |
| SMV 1 | 5088 | Plus | 5'-(ggatcc)ggctcccagttttgtgaatgaag-3'[b] | SEQ ID NO:8 |
| SMV 9 | 5154 | Minus | 5'-ctcgagggctcaagagccatgacctc-3'[b] | SEQ ID NO:9 |
| SMV 6 | 7265 | Minus | 5'-ctaacccactcactagtcctggatg-3'[c] | SEQ ID NO:10 |
| SMV 7 | 7290 | Plus | 5'-catccaagactagtgagtgggttag-3'[c] | SEQ ID NO:11 |

[a]These primers were designed from NV, LV, CV sequence alignments and do not share complete sequence identity to SMV.
[b]Designed from previously described SMV capsid sequence (Genbank: U75682).
[c]Designed from previously described MeV VP2 sequence (Genbank: X81879).

SMV cDNA clones were sequences with M13 reverse and T7 primers flanking the insert in the pCR2. TOPO vector. After initial sequence was obtained, internal oligonucleotide primers were designed to obtain the complete fragment sequence. Sequencing reaction were carried out with the BigDye™ Terminator Cycle Sequencing Ready Reaction v3.0 according to the manufacturer's instructions (ABI Prism/Applied Biosystems) and analyzed on an ABI 310 Genetic Analyzer. Multiple overlapping sequences were aligned with the Seqman II alignment program (DNAStar Inc.) and assembled into the consensus sequence.

The sequence of the 5' end of SMV was determined with the 5' RACE system for rapid amplification of cDNA ends (Invitrogen, Carlsbad, Calif.) according to the manufacturer's instructions. The first reaction to transcribe the vRNA template to cDNA was performed with the negative sense primer SMV33 located 1,785 nt from the first in-frame start codon (5'-CATAATCAAGTGGAGCTGGG-3') (SEQ ID NO:12). The cDNA was then tailed with cytosine residues with terminal transferase, then amplified by PCR with the provided abridged anchor primer (AAP) and a nested primer SMV21 located at nt 1,013 (5'-CTATCGGTACAAGTFCCAC-3') (SEQ ID NO:13). A third PCR was performed using the AAP and a third nested primer SMV32 located 99 nts from the first start codon (5'-CCAAGGGCTCGTTTAAAAGTGACAG-3') (SEQ ID NO:14). This produced was cloned into the pCR2.1 TOPO vector and the sequence was obtained using the ABI 310 Genetic Analyzer as described above.

Example 3

Sequence Analyses

Sequence identities were determined by separately aligning OFR1, ORF2, and ORF3 sequences of NV, SHV (L07418), HeV (AF093797), Hv (U07611), CV, LV, MeV ORFs 2 and 3 (X81879), and SMV. The sequences were aligned with the AlignX program in the Vector NTI v5.0 program and compiled as pairwise identities. AlignX employs the Clustal W alignment algorithm. (Thompson et al. Nucleic Acids Res. 1994 Nov. 11; 22(22):4673-80.)

The Recombination Identification Program (RIP) was used to evaluate SMV as a potential recombinant virus. (Siepel et al. AIDS Res Hum Retroviruses. 1995 November; 11(11): 1413-6) RIP employs a window that moves across a determined number of nucleotides in an alignment. At each position of the window, the query sequence is compared to a specified number of background sequences. This nucleotide block is then quantified as the percentage of identical base pairs, and the window advances to the next position. The output display reveals the identities of each block between the background and query sequences. The best matches are highlighted if they are significant according to a statistical test. A sequence relationship that shows an extreme shift from insignificant to significant indicates a likely mosaic or recombinant sequence. The sequence analyzed by RIP in the present study was an approximately 1,300 nt region spanning ORF1 and ORF2 (nts 4,000-5,300) of SMV (query sequence). The RIP program was set to compare a 150 nt window, scanned across the query sequence with each of the background sequences (the same nucleotide regions of MeV and HV).

Example 4

Expression of SMV VLPs

The subgenomic RNA of the SMV genome consists of ORF2 and ORF3 encoding structural proteins VP1 and VP2, respectively. (Jiang et al. J Virol. 1992 November; 66(11): 6527-32; Glass et al. J Virol. 2000 July; 74(14):6581-91). In several strains of calicivirus, these ORFs have been cloned into the baculovirus expression system and expressed as self-assembling VLPs. VLPs have been expressed for NV, HV, Mexico virus (MX), Toronto virus, Sapporo-like viruses, Grimsby virus, RHDV, and porcine enteric calicivirus (PEC). (Jiang et al. J Virol. 1992 November; 66(11):6527-32; Green et al. J Clin Microbiol. 1997 July; 35(7): 1909-14; Jiang et al. J Clin Microbiol. 1995 June; 33(6): 1452-5; Leite et al. Arch Virol. 1996; 141(5):865-75; Jiang et al. J Virol Methods. 1999 March; 78(1-2):81-91; Hale et al. Clin Diagn Lab Immunol. 1999 January; 6(1):142-5; Laurent et al. J Virol. 1994 October; 68(10):6794-8; Guo et al. J Virol. 1999 November; 73(11):9625-31.)

Recombinant SMV-like particles (rSMV) were expressed with the Bac-to-Bac Baculovirus expression system (Invitrogen) according to manufacturer's instructions. cDNA clones containing both ORF2 and ORF3 (ORF2/3) were obtained by RT-PCR from vRNA templates, and were subcloned into the BamHI site of the pFastbac1 vector. SMV ORF2/3 wt contained consensus "wild-type" sequence verified by three ORF2 sequences from distinct clones. One clone, ORF2/3H91R, contained a histidine to arginine mutation at aa 91. The pFastbac-SMV ORF2/3 wt and mutant H91R vectors were purified and transposed into the baculovirus bacmid propagated in DH10bac *Escherichia coli*. Recombinant bacmids from each clone were purified and transfected into Sf9 insect cells. Expression of rSMV in Sf9 cells was performed as previously described. (Jiang et al. J Virol. 1992 November; 66(11):6527-32.) Sf9 cells ($1\times10^8$ to $6\times10^8$) were infected with either SMV ORF2/3 wt or the H91R mutant recombinant baculovirus at multiplicities of infection (MOI) ranging from 2-10. VLPs were harvested from the medium 5-7 days post infection as previously described. (Jiang et al. J Virol. 1992 November; 66(11):6527-32; Hardy et al. J Virol. 1995 March; 69(3): 1693-8.) The cells were pelleted for 5 min at 500×g, and recombinant VLPs in the supernatant were concentrated by ultracentrifugation for 2 h at 26,000 rpm in a Beckman SW28 rotor at 4° C. Pellets were suspended in WFI, and then centrifuged through a CsCl gradient (0.39 g/ml) for 18 hours at 35K in a Beckman SW55 rotor. The band containing virus-like particles was collected from the gradient, diluted in sterile water and centrifuged again for two hours at 26,000 rpm in the SW28 rotor. Resulting pellets were suspended in WFI and stored at 4° C. SMV capsid protein were evaluated by SDS-PAGE and Coomassie blue staining. Recombinant SMV particles were visualized by staining with 1% uranyl acetate and observed by electron microscopy (EM).

Example 5

Genome Organization of SMV

The consensus sequence of SMV determined from sequence alignments of cDNA fragments obtained by RT-PCR revealed a viral genome of 7,537 nts in length excluding the 3' polyadenylated tail (FIG. 1). The 5' untranslated sequence determined to be GUGAAUGAAG (SEQ ID NO:15) directly upstream from the first in-frame strong context AUG is conserved among GII noroviruses sequences. The genome encodes three ORFs. ORF1 (nts 5-5104) encodes a polyprotein with a predicted size of ~189,000 MW. The first in-frame start codon of ORF1 at nt 5 is not in a strong context for translation initiation. (Kozak. Nucleic Acids Res. 1981 Oct. 24; 9(20):5233-52.) This start codon is followed by two in-frame initiation codons at positions 11 and 98 that are in the proper context for translation initiation. ORF1 overlaps ORF2 by 17 nt. The first 18 nt of the SMV genome is repeated internally starting at nt 5,081, presumably the site of subgenomic RNA synthesis as described for other noroviruses. (Hardy et al. Virus Genes. 1996; 12(3):287-90.) ORF2 encodes the major capsid protein VP1. ORF2 begins at nt 5,085, and because of the repeating sequence, has two in-frame AUG codons, as in ORF1. Sequence obtained by RT-PCR of SMV RNA in this study shred 100% sequence identity with previously reported ORF2 sequence. (Hardy et al. Arch Virol. 1997; 142(7): 1469-79.) The size of SMV VP1 was calculated to be ~59,000 MW. ORF3 encoding VP2 begins at nt 6,713 and the stop and start codons of ORF2 and ORF3 respectively, overlap by one nucleotide. ORF3 is terminated by two sequential in-frame stop codons. The predicted protein size of VP2 was calculated to be approximately 28,000 MW. The poly-A region that was amplified was oligo-dT primers ranged from 18-22 nt in length.

The genome organization of SMV is consistent with other characterized human caliciviruses in the Norovirus genus. (Lambden et al. Science. 1993 Jan. 22; 259(5094):516-9; Jiang et al. Virology. 1993 July; 195(1):51-61; Hardy et al. Virus Genes. 1996; 12(3):287-90; Schreier et al. Arch Virol. 2000; 145(3):443-53; Dingle et al. J Gen Virol. 1995 September; 76 (Pt 9):2349-55; Seah et al. J Virol. 1999 December; 73(12):10531-5; Green et al. J Infect Dis. 2002 Jan. 15; 185 (2):133-46. Epub 2002 Jan. 3; Pletneva et al. Virus Genes. 2001; 23(1):5-16.)

Example 6

Predicted Cleavage Sites in the ORF1 Polyprotein

Figure 2:
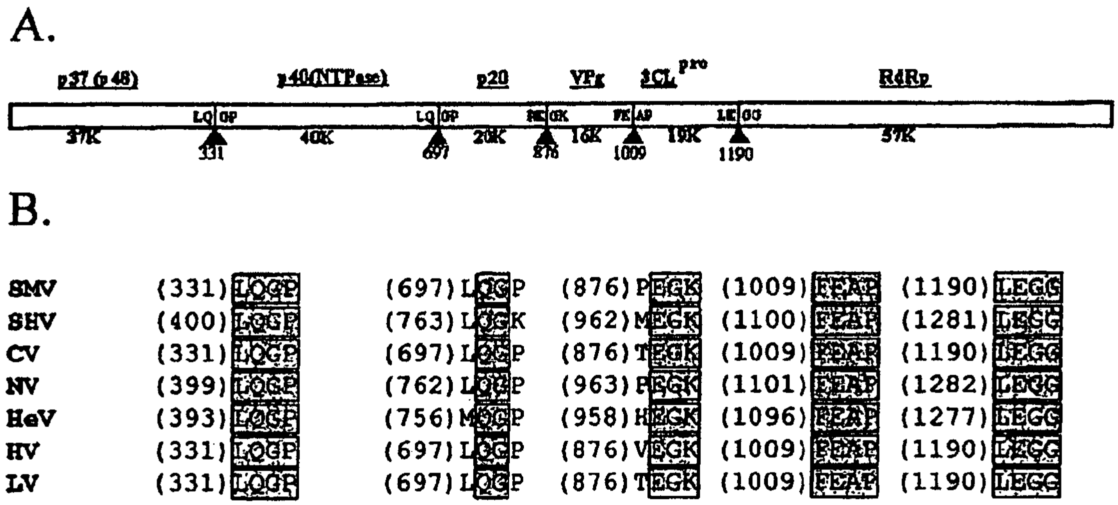
FIG. 2 shows the predicted cleavages sites in ORF1. Panel A shows the large polyprotein encoded by ORF1 and its cleavage into the viral nonstructural proteins. The protein, predicted size, cleavage sequence and amino acid locations are indicated. Panel B shows the cleavage sites of SMV compared to SHV, CV, NV, HeV, HV, and LV. LQGP (SEQ ID NO:16); LQGK (SEQ ID NO:17); MQGP (SEQ ID NO:18); PEGK (SEQ ID NO:19); MEGK (SEQ ID NO:20); TEGK (SEQ ID NO:21); HEGK (SEQ ID NO:22); VEGK (SEQ ID NO:23); FEAP (SEQ ID NO:24); LEGG (SEQ ID NO:25).

The ORF1 polyprotein is cleaved by a viral protease into nonstructural proteins. (Liu et al. J Virol. 1996 April; 70(4): 2605-10; Boniotti et al. J Virol. 1994 October; 68(10):6487-95.) Several cleavage sites have been defined experimentally for SHV, CV, NV. (Seah et al. J Virol. 1999 December; 73(12): 10531-5; Liu et al. J Virol. 1996 April; 70(4):2605-10; Liu et al. J Gen Virol. 1999 February; 80 (Pt 2):291-6; Hardy et al. Virus Res. 2002 October; 89(1):29-39.) Predicted cleavage sites in the SMV polyprotein were analyzed by sequence comparisons to the experimentally determined cleavage sites of SHV, CV, and NV ORF1 (FIG. 2). ORF1 amino acid sequences of human caliciviruses HeV, LV, and HV were used to align the predicted cleavage sites and identify the conserved sequences (FIG. 2*b*). SMV aligned with all five cleavage sites determined in SHV, CV, and NV, which could be processed into six protein cleavage products similar to SHV. The N-terminal protein p37 predicted in all GII strains corresponds to p48 of GI caliciviruses. The function of this N-terminal protein is not known. The second predicted product p40 has demonstrated NTPase activity in rabbit hemorrhagic disease virus (RHDV) and NV. (Pfister et al. J Virol. 2001 February; 75(4): 1611-9; Marin et al. J Virol. 2000 November; 74(22): 10846-51.) The third cleavage product, p20, is smaller than the GI homologs, which are predicted to be 22 kD. The function of p20/p22 proteins is not known. The fourth product is a predicted 16 kD protein genome-linked protein VPg described experimentally in RHDV, Pan-1, and FCV. (Wirblich et al. J Virol. 1996 November; 70(11):7974-83; Dunham et al. Arch Virol. 1998; 143(12):2421-30; Sosnovtsev et al. Virology. 2000 Nov. 10; 277(1): 193-203.) The fifth potential cleavage product p19 is the 3C-like cysteine proteinase. (Liu et al. J Virol. 1996 April; 70(4):2605-10; Boniotti et al. J Virol. 1994 October; 68(10):6487-95; Wirblich et al. J Virol. 1995 November; 69(11):7159-68; Sosnovtsev et al. J Virol. 1998 April; 72(4):3051-9.) The sixth predicted cleavage product is the RNA-dependent-RNA polymerase with a predicted size of 57 kD. (Vazquez et al. J Virol. 1998 April; 72(4):2999-3004.)

Thus, cleavage at all five of these conserved locations would produce six protein cleavage products. Four of these products have been identified experimentally as the NTPase, VPg, proteinase, and polymerase in noroviruses and other caliciviruses. (Wirblich et al. J Virol. 1996 November; 70(11):7974-838, Liu et al. J Virol. 1996 April; 70(4):2605-10; Boniotti et al. J Virol. 1994 October; 68(10):6487-95; Marin et al. J Virol. 2000 November; 74(22):10846-51; Dunham et al. Arch Virol. 1998; 143(12):2421-30; Sosnovtsev et al. Virology. 2000 Nov. 10; 277(1): 193-203; Wirblich et al. J Virol. 1995 November; 69(11):7159-68; Sosnovtsev et al. J Virol. 1998 April; 72(4):3051-9, Vazquez et al. J Virol. 1998 April; 72(4):2999-3004.) The two products p40/p48 and p20/22 do not share sufficient sequence similarity with other viral proteins to suggest a function. In SMV, as with other GII strains, these two putative cleavage products have different calculated MWs and show the highest degree of sequence divergence (Example 7), which suggests the primary sequence of these proteins is not selected for as stringently as the other nonstructural proteins with known or predicted functions.

TABLE 2

Percent Nucleotide and Amino Acid Identities of Human Caliciviruses Representing Two Genogroups Percent nt and aa in ORF1

| | | | | | | | | |
|---|---|---|---|---|---|---|---|---|
| NV[a] | nt | 75 | 73 | 55 | 55 | 55 | 61 | 55 |
| | as | 86 | 82 | 50 | 50 | 50 | 61 | 50 |
| SHV[a] | nt | | 73 | 56 | 56 | 56 | 62 | 56 |
| | aa | | 82 | 51 | 51 | 51 | 63 | 51 |
| HeV[a] | nt | | | 56 | 56 | 56 | 61 | 56 |
| | aa | | | 50 | 50 | 50 | 61 | 50 |
| CV[b] | nt | | | | 93 | 87 | 79 | 82 |
| | aa | | | | 98 | 96 | 93 | 95 |
| LV[b] | nt | | | | | 87 | 81 | 83 |
| | aa | | | | | 96 | 93 | 94 |
| HV[b] | nt | | | | | | 80 | 83 |
| | aa | | | | | | 93 | 94 |
| MeV[b,c] | nt | | | | | | | 79 |
| | aa | | | | | | | 92 |

[a]Genogroup I, NV (Norwalk virus), SHV (Southhampton virus), HeV (Hesse virus).
[b]Genogroup II, CV (Camberwell virus), LV (Lordsdale virus), HV (Hawaii virus), MeV (Melksham virus), SMV (Snow Mountain virus).
[c]MeV alignments: RdRp only.

Example 7

Identities Between Human Caliciviruses

Nucleotide and amino acid sequences were aligned for the three ORFs of SMV, SHV, LV, CV, HV, NV, HeV, and ORFs 2 and 3 of MeV. MeV is a norovirus strain closely related to SMV. but was not included in full ORF1 alignments because the complete ORF1 sequence is not available. Percent identities were determined for each alignment and are shown in Tables 2-4. ORF1 alignments showed the most distinction between GI and GII viruses, whereas the GII viruses were highly conserved in ORF1. SMV shared the highest identities in ORF1 with HV and CV (Table 2). Percent identities decrease significantly in ORF2 (Table 3). The highest identities in ORF2 were between CV and LV, and SMV and MeV. Other than MeV, SMV shared the closest identity to HV in nucleotide and amino acid sequence, at 70% and 76%, respectively. Due to the lack of a standardized assay to compare antigenic properties, it has been suggested that noroviruses possessing greater than 20% amino acid divergence in the capsid gene could be represented as antigenically distinct capsid types. (Green et al. Virus Genes. 2000; 20(3):227-36. Erratum in: Virus Genes 2001; 23(2):241.) Applying this rationale would result in all of the sequenced caliciviruses shown here being antigenically distinct, with the exceptions of CV and LV, and SMV and Mev (Table 3). Overall sequence identities continued to decrease with GII ORF3 alignments (Table 4), as expected from previously comparisons of this region. (Seah et al. Arch Virol. 1999; 144(5): 1007-14.) CV and LV shared very high identities in ORFs 2 and 3, and the identities decreased slightly in ORF3. SMV continued to share the highest identities with MeV, and to a lesser degree with HV.

TABLE 3

Percent Nucleotide and Amino Acid Identities of Human Caliciviruses Representing Two Genogroups Percent nt and aa in ORF2

| | | | | | | | | |
|---|---|---|---|---|---|---|---|---|
| NV[a] | nt | 68 | 68 | 53 | 53 | 54 | 55 | 55 |
| | aa | 69 | 71 | 43 | 44 | 47 | 47 | 47 |
| SHV[a] | ny | | 68 | 53 | 53 | 54 | 54 | 54 |
| | aa | | 71 | 42 | 43 | 45 | 44 | 44 |
| HeV[a] | nt | | | 53 | 53 | 53 | 54 | 55 |
| | aa | | | 43 | 44 | 46 | 45 | 45 |
| CV[b] | nt | | | | 93 | 66 | 64 | 64 |
| | aa | | | | 98 | 64 | 63 | 63 |
| LV[b] | nt | | | | | 65 | 63 | 64 |
| | aa | | | | | 64 | 62 | 63 |
| HV[b] | nt | | | | | | 70 | .70 |
| | aa | | | | | | 76 | 76 |
| MeV[b] | nt | | | | | | | 94 |
| | aa | | | | | | | 98 |

[a]Genogroup I, NV (Norwalk virus), SHV (Southhampton virus), HeV (Hesse virus).
[b]Genogroup II, CV (Camberwell virus), LV (Lordsdale virus), HV (Hawaii virus), MeV (Melksham virus), SMV (Snow Mountain virus).

Example 8

SMV Recombination

Previous sequence analysis of the RNA polymerase and capsid regions of SMV suggested this strain might be a recombinant virus. (Hardy et al. Arch Virol. 1997; 142(7): 1469-79.) This suggestion was made based on the fact that the polymerase region of SMV showed high sequence identities with other GII viruses, but the capsid sequence diverged considerably. In addition, SMV clustered within different GII strains in phylogenetic analyses depending on which region was analyzed. Additional sequence alignments were performed in the current study to further investigate the possibility of SMV as a norovirus recombinant. SMV aligned with MeV starting at nucleotide 4,104 of the SMV genome and terminating at the ORF1 stop codon showed 79% nucleotide identity, compared to an identity of 84% with SMV/CV alignments of the same region. Amino acid sequence alignments of SMV/CV and SMV/MeV resulted in 96% and 92% identities, respectively, for the RdRp region, and 63% and 98%, respectively, for the capsid sequence.

TABLE 4

Percent Nucleotide and Amino Acid Identities of Human Caliciviruses Representing Two Genogroups Percent nt and aa in ORF3

| | | | | | | | | |
|---|---|---|---|---|---|---|---|---|
| NV[a] | nt | 65 | 67 | 39 | 39 | 44 | 41 | 42 |
| | aa | 72 | 72 | 31 | 33 | 36 | 35 | 34 |
| SHV[a] | nt | | 68 | 42 | 40 | 47 | 42 | 42 |
| | aa | | 76 | 32 | 32 | 37 | 36 | 35 |
| HeV[a] | nt | | | 42 | 42 | 41 | 41 | 41 |
| | aa | | | 31 | 32 | 34 | 33 | 32 |
| CV[b] | nt | | | | 91 | 60 | 60 | 60 |
| | aa | | | | '90 | 56 | 54 | 55 |
| LV[b] | nt | | | | | 60 | 61 | 60 |
| | aa | | | | | 55 | 55 | 57 |
| HV[b] | nt | | | | | | 68 | 68 |
| | aa | | | | | | 65 | 67 |
| MeV[b] | nt | | | | | | | 97 |
| | aa | | | | | | | 98 |

[a]Genogroup I, NV-Norwalk virus, SHV-Southhampton virus, HeV-Hesse virus.
[b]Genogroup II, CV-Camberwell virus, LV-Lordsdale virus, HV-Hawaii virus, MeV-Melksham virus, SMV-Snow Mountain virus.

Figure 3:
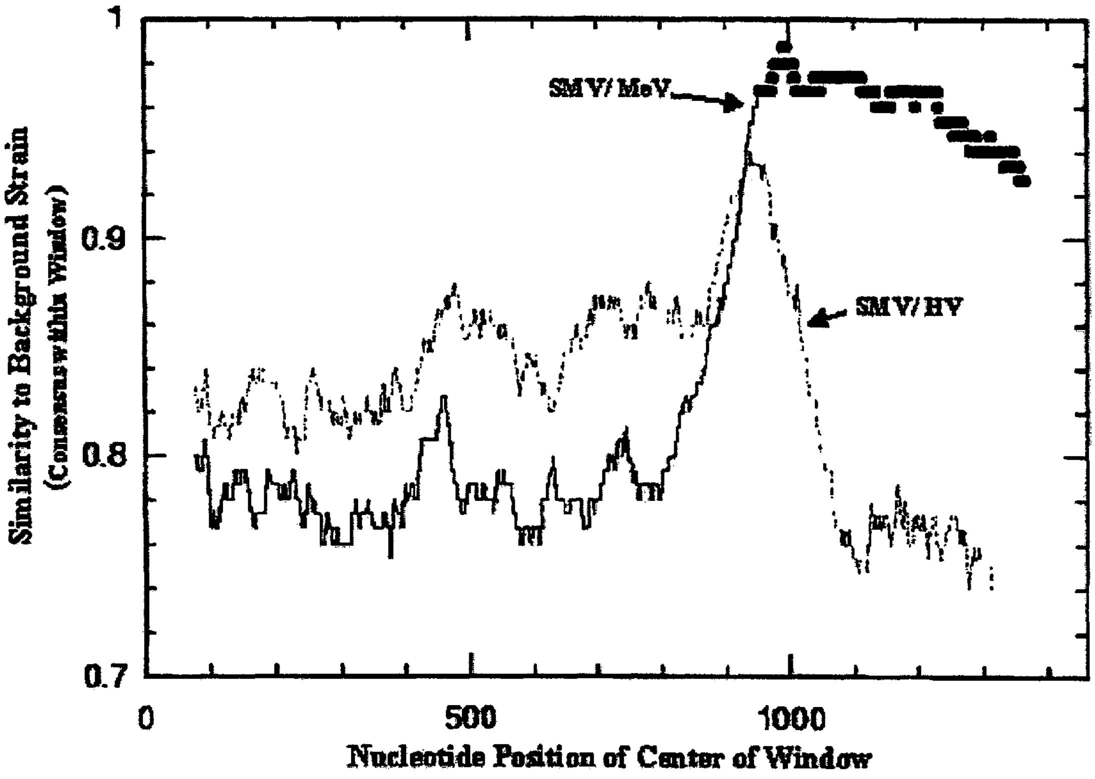
FIG. 3 shows RIP analysis of SMV compared with MeV (black); and SMV compared with HV (gray). Sequence analyzed is the ~1,300 nucleotide region spanning ORFs 1 and 2 (nts 4,000-5,300). The RIP program compared a 150 nt window, scanned across the query sequence with each of the two background sequences (MeV and HV). Similarities are quantified as the percentage of identical base pairs. Thick lines indicate a statistically significant relationship with the background sequence. Likely recombinants are identified by a drastic divergence in strain similarity.
Figure 5:
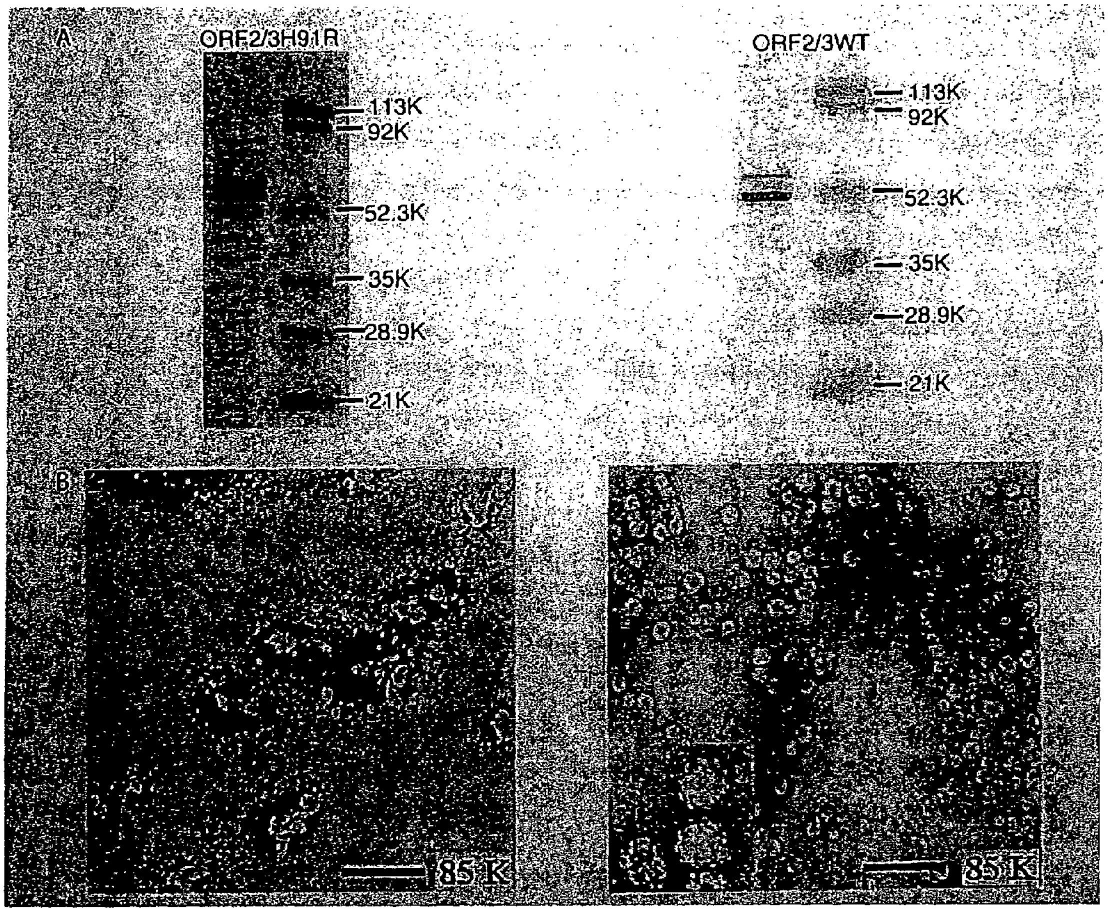
FIG. 5 shows recombinant SMV (rSMV) VLP assembly from wild type and H19R ORF2/3 baculovirus. Panel A shows SDS-PAGE, Coomassie blue stained gels of VP1 proteins from ORF2/3H91R and ORF2/3 wt. VP1 of the H91R mutant was partially purified by ultracentrifugation of insect cell culture medium. The sample displaying VP1 of ORF2/3 wt is from cesium chloride banded and concentrated VLPs. Panel B shows electron micrographs of H91R, left, and wild type VP1 proteins, right. Bars represent 118 and 43 nm for the inlay. The inlay is 233K magnification.

The recombinant identification program (RIP) then was used to further investigate SMV as a potentially recombinant norovirus. RIP was been used successfully to identify mosaic genetic sequences in HIV-1 subtypes and to subsequently identify HIV recombinants and other potential HuCV recombinants. (Siepel et al. AIDS Res Hum Retroviruses. 1995 November; 11(11): 1413-6; Vinje et al. Arch Virol. 2000; 145(2):223-41.) RIP analysis of SMV compared to MeV and HV across a ~1,3000 nucleotide region (nt 4,000-5,300) showed distinctly significant chimeric relationships between ORF1 and ORF2 (FIG. 3). Comparisons to HV showed a change in sequence similarity, but not statistically significant relationship was observed. The putative recombination region (the area where the graph increases sharply) mapped roughly to nt 5020 of the SMV genome, ~50 nt from the ORF2 start codon. Taken together, these data, and the change in sequence identities between ORF1 and ORF2, provide further evidence that SMV is a recombinant norovirus.

Thus, the high sequence identities in the polymerase region between SMV and the other GII viruses had predicted most of these viruses would be similar in the capsid sequence. Therefore, it was a surprise once the SMV capsid sequence was known, that with the exception of MeV, SMV differed so significantly with the other GII strains (<76% identity). (Hardy et al. Arch Virol. 1997; 142(7): 1469-79.) Typically, noroviruses that are nearly identical in the capsid (>97%), also are nearly identical in the polymerase region (>90%). This resulted in the suggestion that SMV might be a recombinant viruses. A second study characterized a human calicivirus also though to be a naturally occurring recombinant. (Jiang et al. Arch Virol. 1999; 144(12):2377-87.) This was (Arg320) shared 95% aa identity with MX virus in the capsid region but a divergence of 87% aa identity was observed with comparing the polymerase region. In addition, the polymerase region shared 95% identity to LV and 68% in the capsid region. A third extensive study that characterized a large population of human caliciviruses by comparing sequence of all three open reading frames of GI and GII viruses also identified a possible recombinant viruses (Wortley/90/UK) by phylogenetic and RIP analysis. (Vinje et al. Arch Virol. 2000; 145(2):223-41.) Similar analyses of SMV in this study provides further evidence that SMV is a recombinant virus.

Recombination has been well studied and several mechanisms have been proposed. (Kirkegaard et al. Cell. 1986 Nov. 7; 47(3):433-43; Duggal et al. Proc Natl Acad Sci USA. 1997 Dec. 9; 94(25):13786-91; Duggal et al. Virology. 1999 May 25; 258(1):30-41; Nagy et al. EMBO J. 1998 Apr. 15; 17(8): 2392-403; Nagy et al. EMBO J. 1999 Oct. 15; 18(20):5653-65; Nagy et al. Virology. 1997 Aug. 18; 235(1):1-9.) One mechanisms, similarity-assisted recombination, relies on a donor template aligning with a conserved sequence on an acceptor template to act as a primer, followed by a stem loop recognition motif to recruit the polymerase and extend the prime on the acceptor template. (Nagy et al. Virology. 1998 Sep. 30; 249(2):379-92; Nagy et al. EMBO J. 1998 Apr. 15; 17(8):2392-403; Nagy et al Virology. 1998 Sep. 30; 249(2): 393-405.) This mechanism shares an interestingly similarity to the putative recombination region mapped for SMV in that a highly conserved sequence is directly upstream of a predicted stem loop structure. This putative recombination region at nt 5,020 of SMV shares 100% identity with MeV over 47 nt, followed by 13 nt with two mismatches. Sequence comparisons to the other GII strains for which sequence is available, including other proposed HuCV recombinants showed ~93% nucleotide identity in this region. The proposed subgenomic RNA initiation sequence is directly following this sequence. RNA secondary structure analysis (mfold v3.1) of the SMV recombination region identified several stem-loop structures with similar morphology and stability as motif hairpins described in recombination studies (data not shown). (Mathews et al. J Mol Biol. 1999 May 21; 288(5):911-40; Zuker et al. Algorithms and thermodynamics for RNA secondary structure prediction: a practical guide, in *RNA Biochemistry and Biotechnology,* 1999, pp. 11-43.)

Example 9

Expression of rSMV VLPs

SMV VP1 expressed in the baculovirus system was produced to relatively high levels in both the ORF2/3 wt and H91R constructs. (Jiang et al. J Virol. 1992 November; 66(11):6527-32; Glass et al. J Virol. 2000 July; 74(14):6581-91.) VP2 is expressed at extremely low levels, and usually is not detectable by the methods employed here. Self-assembly of VLPs, however, was only obtained from the ORF2/3 wt construct (FIG. 4B). Although protein expression by the H91R construct was observed (FIG. 4A), H91R protein did not assemble into VLPs, despite a variety of infection and purification conditions, including variance in multiplicities of infection, cell numbers, serum concentrations, and purification conditions. In contrast, the ORF2/3 wt recombinant did yield intact VLPs with an average size of 30 nm (FIG. 4B). These data suggest the histidine residue at position 91 of VP1 is important for particle assembly under standard conditions that allow assembly of other recombinant norovirus-like particles.

Two principle domains are present in the folded capsid protein of noroviruses, the shell (S) and a protruding (P) domain. (Prasad et al. Science. 1999 Oct. 8; 286(5438):287-90.) The P domain is composed of two subdomains, P1 and P2. The S domain, associated with the inner portion of the capsomere, is formed by the N-terminal 225 residues in NV, and this region is highly conserved among all noroviruses. (Hardy et al. Arch Virol. 1997; 142(7):1469-79; Neill. Virus Res. 1992 July; 24(2):211-22.) The recombinant baculovirus ORF2/3H91R contained a single nucleotide substitution being replaced by an arginine residue. This mutation was likely generated during RT-PCR. The presence of this substitution in VP1 resulted in the inability of protein expressed by this construct to form VLPs. The lack of particle formation by N-terminal mutants has been described for NV. (Bertolotti-Ciarlet et al. J Virol. 2002 April; 76(8):4044-55.) NV capsid mutations that removed 34 or 98 amino acid residues from the N terminus were unable to form particles, presumably because the deleted structural motifs were unavailable for interacting with dimeric subunits. An NV cDNA encoding VP1 with three amino acid substitutions failed to assemble into VLPs when expressed by the Venezuelan equine encephalitis virus (VEE) expression system. (Baric et al. J Virol. 2002 March; 76(6):3023-30.) Two of these mutations were near the N terminus in the S domain, and the third was at position 285 in the P1 subdomain. The inability to form particles as result of one residue substitution has not been documented before. This region of the capsid protein has been established as an important domain for particle formation, and the histidine residue at position 91 must be pivotal for the interactions that are necessary for assembly. This histidine residue is 100% conserved in the eight human calicivirus strains analyzed in this study. Based on these date, careful attention should be paid to sequence identities, particularly in the S domain, when attempting to express virus-like particles from noroviruses.

Example 10

Inducing an Immune Response to rSMV VLPs

SMV VLPs are produced in the baculovirus expression system described above. VLPs in the supernatant are concentrated by ultracentrifugation for 2 h at 26,000 rpm in a Beckman SW28 rotor at 4° C. Pellets are suspended in WFI, and centrifuged through a CsCl gradient (0.39 g/ml) for 18 hours at 35K in a Beckman SW55 rotor. The band containing virus-like particles is collected from the gradient, diluted in sterile water and centrifuged again for two hours at 26,000 rpm in the SW28 rotor. Resulting pellets are suspended in WFI and stored at 4° C.

I.V. Immunization: The protein content of the purified rSMV VLPs is determined by Coomassie Brilliant Blue Colorimetric Method (Bio-Rad, Hercules, Calif.). The concentration of the VLPs is adjusted to 5, 10, and 20 μg/0.1 mL in sterile WFI/isotonic saline solution. Naïve 7-9 week old, female New Zealand White rabbits are locally anesthetized, bled, and administered I.V. via an ear vessel 0.1 mL VLP/saline solution. The rabbits are bled and boosted at weeks 2, 4, and 6. A final bleed is taken at week 8. Oil of winter (methyl salicylate N.F. synthetic) is used an external analgesic and a natural irritant and aids in dilating the vessels.

S.C. Immunization: SMV VLPs are mixed with Freunds Complete Adjuvant and administered s.c. to naïve 7-9 week old, female New Zealand White rabbits. Each rabbit receives 20 μg/0.1 mL. Rabbits are bled and boosted using SMV VLPs in Freunds Incomplete Adjuvant at weeks 2, 4, and 6. The final bleed is taken at week 8.

To remove rabbit antibodies cross reactive with VLPs that contain VP1 and not VP2 (VP1-VLPs) aliquots of the sera are diluted 1:10 to 1:50 in PBS and are incubated with VP1-VLPs for 30 min. at room temperature. Antibodies bound to VP1-VLPs are removed by pelleting the VP1-VLPs in an untracentrifuge. Antibodies cross reactive with VP1-VLPs also can be absorbed from rabbit sera by affinity chromatography using a column having attached VP1-VLPs as described in Sambrook et al. *Molecular Cloning: A Laboratory Manual Third Edition* 14.28-14.30 (Cold Spring Harbor Laboratory Press 2001 (ISBN 0-87969-576-5); Harlow and Lane, Antibodies: A Laboratory Manual (New York: Cold Spring Harbor Laboratory Press, 1988)). VP1-VLPs are produced and purified according to the method of Harrington et al. J. Virol. 76(223):12335-12343 (2002), expressly incorporated by reference.

What is claimed is:

1. A composition comprising a virus-like particle comprising Snow Mountain virus VP1 protein and Snow Mountain virus VP2 protein.

2. The composition according to claim 1, wherein said VP2 protein is greater than 98% identical to SEQ ID NO: 28.

3. The composition according to claim 1, wherein said VP2 protein is SEQ ID NO: 28.

4. The composition according to claim 1, wherein said VP2 protein is encoded by a nucleic acid that is greater than 97% identical to SEQ ID NO: 31.

5. The composition according to claim 1, wherein said VP2 protein is encoded by a nucleic acid that encodes for an amino acid sequence that is greater than 98% identical to SEQ ID NO: 28.

6. The composition according to claim 1, wherein said VP1 protein is greater than 98% identical to SEQ ID NO: 27.

7. The composition according to claim 1, wherein said VP1 protein is SEQ ID NO:27.

8. The composition according to claim 1, wherein said VP1 protein is encoded by a nucleic acid that is greater than 94% identical to SEQ ID NO: 30.

9. The composition according to claim 1, wherein said VP1 protein is encoded by a nucleic acid identical to SEQ ID NO: 30.

10. The composition according to claim 1, wherein said VP1 is encoded by a nucleic acid that encodes an amino acid sequence that is greater than 98% identical to SEQ ID NO: 27.

11. The composition according to claim 1, wherein said VP1 protein is identical to SEQ ID NO: 27 and said VP2 protein is identical to SEQ ID NO: 28.

12. The composition according to claim 1, wherein said composition further comprises and adjuvant and an amount of said virus-like particle suitable for inducing an immune response to a subject.

13. The composition according to claim 12, wherein said immune response is an antibody response.

14. The composition according to claim 12, wherein said composition further comprises a carrier.

15. A method of making a virus-like particle comprising co-expressing Snow Mountain virus VP1 protein and Snow Mountain virus VP2 protein in a recombinant nucleic acid expression system under conditions suitable for assembly of the expressed VP1 and VP2 proteins into a virus-like particle.

16. The method according to claim 15, wherein said expression system comprises a eukaryotic cell.

17. The method according to claim 16, wherein said eukaryotic cell is an insect cell.

18. The method according to claim 15, wherein said system is a baculovirus expression system.

19. The method according to claim 15, wherein said VP2 protein is greater than 98% identical to SEQ ID NO: 28.

20. The method according to claim 15, wherein said VP2 protein is SEQ ID NO: 28.

21. The method according to claim 15, wherein said VP2 protein is expressed from a nucleic acid that is greater than 97% identical to SEQ ID NO: 31.

22. The method according to claim 15, wherein said VP2 protein is expressed from a nucleic acid that encodes for an amino acid sequence that is greater than 98% identical to SEQ ID NO: 28.

23. The method according to claim 15, wherein said VP1 protein is greater than 98% identical to SEQ ID NO: 27.

24. The method according to claim 15, wherein said VP1 protein is SEQ ID NO: 27.

25. The method according to claim 15, wherein said VP1 protein is encoded by a nucleic acid that is greater than 94% identical to SEQ ID NO: 30.

26. The method according to claim 15, wherein said VP1 protein is encoded by a nucleic acid identical to SEQ ID NO: 30.

27. The method according to claim 15, wherein said VP1 protein is encoded by a nucleic acid that encodes an amino acid sequence that is greater than 98% identical to SEQ ID NO: 27.

28. A method of making an antibody comprising administering composition of claim 1 to an animal.

29. The method according to claim 17, wherein said insect cell is an Sf9 cell.

* * * * *

UNITED STATES PATENT AND TRADEMARK OFFICE

CERTIFICATE OF CORRECTION

PATENT NO. : 7,481,997 B1
APPLICATION NO. : 11/058030
DATED : January 27, 2009
INVENTOR(S) : Michele E. Hardy It is certified that error appears in the above-identified patent and that said Letters Patent is hereby corrected as shown below:

IN THE STATEMENT OF GOVERNMENT SUPPORT

In column 1, lines 14 – 19, replace "This work was supported by Public Health Service grant AI-43450 and by a subcontract from LigoCyte Pharmaceuticals, Inc., Bozeman, Mont., which is supported by the U.S. Army Medical Research and Material Command under Contract No. DAM 17-0 1-C-0040. The government has certain rights in the invention." with -- This invention was made with government support under contract AI-43450 awarded by National Institutes of Heath and contract DAMD 17-01-C-0040 awarded by the Army. The government has certain rights in the invention. --.

Signed and Sealed this
Twenty-fifth Day of September, 2012

David J. Kappos
*Director of the United States Patent and Trademark Office*

SEQUENCE LISTING

<160> NUMBER OF SEQ ID NOS: 32

<210> SEQ ID NO 1
<211> LENGTH: 21
<212> TYPE: DNA
<213> ORGANISM: Artificial
<220> FEATURE:
<223> OTHER INFORMATION: Synthetic

<400> SEQUENCE: 1
gaatgaagat ggcgtctaac g 21

<210> SEQ ID NO 2
<211> LENGTH: 17
<212> TYPE: DNA
<213> ORGANISM: Artificial
<220> FEATURE:
<223> OTHER INFORMATION: Synthetic

<400> SEQUENCE: 2
gggcctgagg accttgc 17

<210> SEQ ID NO 3
<211> LENGTH: 21
<212> TYPE: DNA
<213> ORGANISM: Artificial
<220> FEATURE:
<223> OTHER INFORMATION: Synthetic

<400> SEQUENCE: 3
cttcctggct ttctcctcct c 21

<210> SEQ ID NO 4
<211> LENGTH: 20
<212> TYPE: DNA
<213> ORGANISM: Artificial
<220> FEATURE:
<223> OTHER INFORMATION: Synthetic

<400> SEQUENCE: 4
gacaggatcg agaacaaagg 20

<210> SEQ ID NO 5
<211> LENGTH: 21
<212> TYPE: DNA
<213> ORGANISM: Artificial
<220> FEATURE:
<223> OTHER INFORMATION: Synthetic

<400> SEQUENCE: 5
gaagccaccc tgtggagcca g 21

<210> SEQ ID NO 6
<211> LENGTH: 20
<212> TYPE: DNA
<213> ORGANISM: Artificial
<220> FEATURE:
<223> OTHER INFORMATION: Synthetic

<400> SEQUENCE: 6
ggagtgttga ctacaatgag 20

-continued

<210> SEQ ID NO 7
<211> LENGTH: 18
<212> TYPE: DNA
<213> ORGANISM: Artificial
<220> FEATURE:
<223> OTHER INFORMATION: Synthetic

<400> SEQUENCE: 7
ccagagaagc ctcttctt 18

<210> SEQ ID NO 8
<211> LENGTH: 29
<212> TYPE: DNA
<213> ORGANISM: Artificial
<220> FEATURE:
<223> OTHER INFORMATION: Synthetic

<400> SEQUENCE: 8
ggatccggct cccagttttg tgaatgaag 29

<210> SEQ ID NO 9
<211> LENGTH: 26
<212> TYPE: DNA
<213> ORGANISM: Artificial
<220> FEATURE:
<223> OTHER INFORMATION: Synthetic

<400> SEQUENCE: 9
ctcgagggct caagagccat gacctc 26

<210> SEQ ID NO 10
<211> LENGTH: 25
<212> TYPE: DNA
<213> ORGANISM: Artificial
<220> FEATURE:
<223> OTHER INFORMATION: Synthetic

<400> SEQUENCE: 10
ctaacccact cactagtcct ggatg 25

<210> SEQ ID NO 11
<211> LENGTH: 25
<212> TYPE: DNA
<213> ORGANISM: Artificial
<220> FEATURE:
<223> OTHER INFORMATION: Synthetic

<400> SEQUENCE: 11
catccaagac tagtgagtgg gttag 25

<210> SEQ ID NO 12
<211> LENGTH: 20
<212> TYPE: DNA
<213> ORGANISM: Artificial
<220> FEATURE:
<223> OTHER INFORMATION: Synthetic

<400> SEQUENCE: 12
cataatcaag tggagctggg 20

<210> SEQ ID NO 13
<211> LENGTH: 19
<212> TYPE: DNA
<213> ORGANISM: Artificial
<220> FEATURE:
<223> OTHER INFORMATION: Synthetic -continued

<400> SEQUENCE: 13
ctatcggtac aagttccac 19

<210> SEQ ID NO 14
<211> LENGTH: 25
<212> TYPE: DNA
<213> ORGANISM: Artificial
<220> FEATURE:
<223> OTHER INFORMATION: Synthetic

<400> SEQUENCE: 14
ccaagggctc gtttaaaagt gacag 25

<210> SEQ ID NO 15
<211> LENGTH: 10
<212> TYPE: DNA
<213> ORGANISM: Artificial
<220> FEATURE:
<223> OTHER INFORMATION: Synthetic

<400> SEQUENCE: 15
gugaaugaag 10

<210> SEQ ID NO 16
<211> LENGTH: 4
<212> TYPE: PRT
<213> ORGANISM: Artificial
<220> FEATURE:
<223> OTHER INFORMATION: Synthetic

<400> SEQUENCE: 16

Leu Gln Gly Pro
1

<210> SEQ ID NO 17
<211> LENGTH: 4
<212> TYPE: PRT
<213> ORGANISM: Artificial
<220> FEATURE:
<223> OTHER INFORMATION: Synthetic

<400> SEQUENCE: 17

Leu Gln Gly Lys
1

<210> SEQ ID NO 18
<211> LENGTH: 4
<212> TYPE: PRT
<213> ORGANISM: Artificial
<220> FEATURE:
<223> OTHER INFORMATION: Synthetic

<400> SEQUENCE: 18

Met Gln Gly Pro
1

<210> SEQ ID NO 19
<211> LENGTH: 4
<212> TYPE: PRT
<213> ORGANISM: Artificial
<220> FEATURE:
<223> OTHER INFORMATION: Synthetic

<400> SEQUENCE: 19

Pro Glu Gly Lys
1

-continued

<210> SEQ ID NO 20
<211> LENGTH: 4
<212> TYPE: PRT
<213> ORGANISM: Artificial
<220> FEATURE:
<223> OTHER INFORMATION: Synthetic

<400> SEQUENCE: 20

Met Glu Gly Lys
1

<210> SEQ ID NO 21
<211> LENGTH: 4
<212> TYPE: PRT
<213> ORGANISM: Artificial
<220> FEATURE:
<223> OTHER INFORMATION: Synthetic

<400> SEQUENCE: 21

Thr Glu Gly Lys
1

<210> SEQ ID NO 22
<211> LENGTH: 4
<212> TYPE: PRT
<213> ORGANISM: Artificial
<220> FEATURE:
<223> OTHER INFORMATION: Synthetic

<400> SEQUENCE: 22

His Glu Gly Lys
1

<210> SEQ ID NO 23
<211> LENGTH: 4
<212> TYPE: PRT
<213> ORGANISM: Artificial
<220> FEATURE:
<223> OTHER INFORMATION: Synthetic

<400> SEQUENCE: 23

Val Glu Gly Lys
1

<210> SEQ ID NO 24
<211> LENGTH: 4
<212> TYPE: PRT
<213> ORGANISM: Artificial
<220> FEATURE:
<223> OTHER INFORMATION: Synthetic

<400> SEQUENCE: 24

Phe Glu Ala Pro
1

<210> SEQ ID NO 25
<211> LENGTH: 4
<212> TYPE: PRT
<213> ORGANISM: Artificial
<220> FEATURE:
<223> OTHER INFORMATION: Synthetic

<400> SEQUENCE: 25

Leu Glu Gly Gly
1

-continued

<210> SEQ ID NO 26
<211> LENGTH: 1699
<212> TYPE: PRT
<213> ORGANISM: Snow Mountain Virus

<400> SEQUENCE: 26

```
Met Lys Met Ala Ser Asn Asp Ala Ser Ala Ala Ala Ala Val Asn Ser
1               5                   10                  15

Asn Asn Asp Asn Ala Lys Ser Ser Ser Asp Gly Val Leu Ser Ser Met
            20                  25                  30

Ala Val Thr Phe Lys Arg Ala Leu Gly Ala Arg Pro Lys Gln Pro Pro
        35                  40                  45

Pro Arg Glu Ile Pro Gln Arg Pro Pro Arg Pro Pro Thr Pro Glu Leu
    50                  55                  60

Val Lys Lys Ile Pro Pro Pro Pro Pro Asn Gly Glu Asp Glu Pro Val
65                  70                  75                  80

Val His Tyr Ser Ala Lys Asp Gly Ile Thr Gly Leu Pro Glu Leu Thr
                85                  90                  95

Thr Val Arg Gln Pro Glu Glu Ala Ala Thr Ala Phe Ser Val Pro Pro
            100                 105                 110

Leu Asp Gln Arg Glu Asn Arg Asp Ala Lys Glu Pro Leu Thr Gly Thr
        115                 120                 125

Ile Leu Glu Met Trp Asp Gly Glu Ile Tyr His Tyr Gly Leu Tyr Val
    130                 135                 140

Glu Arg Gly Leu Val Leu Gly Val His Lys Pro Pro Ala Ala Ile Ser
145                 150                 155                 160

Leu Ala Lys Val Glu Leu Thr Pro Leu Ser Leu Tyr Trp Arg Pro Val
                165                 170                 175

Tyr Thr Pro Gln Tyr Leu Ile Ala Pro Asp Thr Leu Arg Lys Leu His
            180                 185                 190

Gly Glu Leu Phe Pro Tyr Thr Ala Phe Asp Asn Asn Cys Tyr Ala Phe
        195                 200                 205

Cys Cys Trp Val Leu Asp Leu Asn Asp Ser Trp Leu Ser Arg Arg Met
    210                 215                 220

Ile Gln Arg Thr Thr Gly Phe Phe Arg Pro Tyr Gln Asp Trp Asn Arg
225                 230                 235                 240

Lys Pro Leu Pro Thr Met Asp Asp Ser Lys Leu Lys Lys Val Ala Asn
                245                 250                 255

Ile Leu Leu Cys Ala Leu Ser Ser Leu Phe Thr Arg Pro Ile Lys Asp
            260                 265                 270

Ile Ile Gly Lys Leu Arg Pro Leu Asn Ile Leu Asn Ile Leu Ala Ser
        275                 280                 285

Cys Asp Trp Thr Phe Ala Gly Ile Val Glu Ser Leu Ile Leu Leu Ala
    290                 295                 300

Glu Leu Phe Gly Val Phe Trp Thr Pro Pro Asp Val Ser Ala Met Ile
305                 310                 315                 320

Ala Pro Leu Leu Gly Asp Tyr Glu Leu Gln Gly Pro Glu Asp Leu Ala
                325                 330                 335

Val Glu Leu Val Pro Ile Val Met Gly Gly Ile Gly Leu Val Leu Gly
            340                 345                 350

Phe Thr Lys Glu Lys Ile Gly Lys Met Leu Ser Ser Ala Ala Ser Thr
        355                 360                 365

Leu Arg Thr Cys Lys Asp Leu Gly Ala Tyr Gly Leu Glu Ile Leu Lys
    370                 375                 380
```

-continued

```
Leu Val Met Lys Trp Phe Phe Pro Lys Lys Glu Glu Ala Asn Glu Leu
385                 390                 395                 400

Ala Met Val Arg Ala Ile Glu Asp Ala Val Leu Asp Leu Glu Ala Ile
                405                 410                 415

Glu Asn Asn His Met Thr Ala Leu Leu Lys Asp Lys Asp Ser Leu Ala
            420                 425                 430

Thr Tyr Met Arg Thr Leu Asp Leu Glu Glu Glu Lys Ala Arg Lys Leu
        435                 440                 445

Ser Thr Lys Ser Ala Ser Pro Asp Ile Val Gly Thr Ile Asn Ala Leu
    450                 455                 460

Leu Ala Arg Ile Ala Ala Ala Arg Ser Leu Val His Arg Ala Lys Glu
465                 470                 475                 480

Glu Leu Ser Ser Arg Leu Arg Pro Val Val Val Met Ile Ser Gly Lys
                485                 490                 495

Pro Gly Ile Gly Lys Thr His Leu Ala Arg Glu Leu Ala Lys Lys Ile
            500                 505                 510

Ala Ile Thr Leu Ser Gly Asp Gln Arg Val Gly Leu Ile Pro Arg Asn
        515                 520                 525

Gly Val Asp His Trp Asp Ala Tyr Lys Gly Glu Arg Val Val Leu Trp
    530                 535                 540

Asp Asp Tyr Gly Met Ser Asn Pro Val His Asp Ala Leu Arg Leu Gln
545                 550                 555                 560

Glu Leu Ala Asp Thr Cys Pro Leu Thr Leu Asn Cys Asp Arg Ile Glu
                565                 570                 575

Asn Lys Gly Lys Val Phe Asp Ser Asp Ala Ile Ile Ile Thr Thr Asn
            580                 585                 590

Leu Ala Asn Pro Ala Pro Leu Asp Tyr Val Asn Phe Glu Ala Cys Ser
        595                 600                 605

Arg Arg Ile Asp Phe Leu Val Tyr Ala Asp Ala Pro Asp Val Glu Lys
    610                 615                 620

Ala Lys Arg Asp Phe Pro Gly Gln Pro Asp Met Trp Lys Ser Ala Tyr
625                 630                 635                 640

Ser Pro Asp Phe Ser His Ile Lys Leu Met Leu Ala Pro Gln Gly Gly
                645                 650                 655

Phe Asp Lys Asn Gly Asn Thr Pro His Gly Lys Gly Val Met Lys Thr
            660                 665                 670

Leu Thr Thr Gly Ser Leu Ile Ala Arg Ala Ser Gly Leu Leu His Glu
        675                 680                 685

Arg Leu Asp Glu Phe Glu Leu Gln Gly Pro Asn Leu Thr Thr Phe Asn
    690                 695                 700

Phe Asp Arg Asn Lys Ile Gln Ala Phe Arg Gln Leu Ala Ala Glu Asn
705                 710                 715                 720

Lys Tyr Gly Leu Val Asp Thr Met Arg Val Gly Gly Gln Leu Lys Gly
                725                 730                 735

Val Arg Thr Ile Pro Glu Leu Lys Gln Ala Leu Lys Asn Ile Leu Ile
            740                 745                 750

Lys Arg Cys Gln Ile Val Tyr Gly Gly Ser Thr Tyr Thr Leu Glu Ser
        755                 760                 765

Asp Gly Lys Gly Asn Val Lys Val Glu Lys Val Gln Asn Thr Asn Ile
    770                 775                 780

Gln Ile Asn Asn Glu Leu Ala Gly Ala Leu His His Leu Arg Cys Ala
785                 790                 795                 800
```

-continued

```
Arg Ile Arg Tyr Tyr Val Lys Cys Val Gln Glu Ala Leu Tyr Ser Ile
                805                 810                 815

Ile Gln Ile Ala Gly Ala Ala Phe Val Thr Thr Arg Ile Val Lys Arg
            820                 825                 830

Met Asn Ile Gln Asn Leu Trp Ser Arg Pro Pro Val Gly Asp Ala Glu
        835                 840                 845

Glu Val Thr Ser Gln Asp Gly Cys Pro Lys Pro Lys Asp Asp Glu Glu
    850                 855                 860

Phe Val Ile Ser Ser Ser Asp Ile Thr Pro Glu Gly Lys Lys Gly Lys
865                 870                 875                 880

Asn Lys Thr Gly Arg Gly Lys Lys His Thr Ala Phe Ser Ser Lys Gly
                885                 890                 895

Leu Ser Asp Glu Glu Tyr Asp Glu Tyr Lys Arg Ile Arg Glu Glu Arg
            900                 905                 910

Asn Gly Lys Tyr Ser Ile Glu Glu Tyr Leu Gln Asp Arg Asp Lys Tyr
        915                 920                 925

Tyr Glu Glu Val Ala Ile Ala Arg Ala Thr Glu Glu Asp Phe Cys Glu
    930                 935                 940

Glu Glu Glu Ala Lys Ile Arg Gln Arg Ile Phe Arg Pro Thr Arg Lys
945                 950                 955                 960

Gln Arg Lys Glu Glu Arg Ala Ser Leu Gly Leu Val Thr Gly Ser Glu
                965                 970                 975

Ile Arg Lys Arg Asn Pro Asp Asp Phe Lys Pro Lys Gly Lys Leu Trp
            980                 985                 990

Ala Asp Asp Glu Arg Val Val Asp  Tyr Asn Glu Lys Leu  Ser Phe Glu
        995                 1000                1005

Ala Pro  Pro Ser Ile Trp Ser  Arg Ile Val Asn Phe  Gly Ser Gly
    1010                 1015                 1020

Trp Gly  Phe Trp Val Ser Pro  Ser Leu Phe Ile Thr  Ser Thr His
    1025                 1030                 1035

Val Ile  Pro Gln Gly Thr Gln  Glu Phe Phe Gly Val  Pro Ile Lys
    1040                 1045                 1050

Gln Ile  Gln Ile His Lys Ser  Gly Glu Phe Cys Arg  Leu Arg Phe
    1055                 1060                 1065

Pro Lys  Ser Ile Arg Thr Ala  Val Thr Gly Met Ile  Leu Glu Glu
    1070                 1075                 1080

Gly Ala  Pro Glu Gly Thr Val  Val Ser Leu Leu Ile  Lys Arg Pro
    1085                 1090                 1095

Thr Gly  Glu Leu Met Pro Leu  Ala Ala Arg Met Gly  Thr His Ala
    1100                 1105                 1110

Thr Met  Lys Ile Gln Gly Arg  Thr Val Gly Gly Gln  Met Gly Met
    1115                 1120                 1125

Leu Leu  Thr Gly Ser Asn Ala  Lys Ser Met Asp Leu  Gly Thr Thr
    1130                 1135                 1140

Pro Gly  Asp Cys Gly Cys Pro  Tyr Ile Tyr Lys Arg  Gly Asn Asp
    1145                 1150                 1155

Tyr Val  Val Ile Gly Val His  Thr Ala Ala Ala Arg  Gly Gly Asn
    1160                 1165                 1170

Thr Val  Ile Cys Ala Thr Gln  Gly Ser Glu Gly Glu  Ala Thr Leu
    1175                 1180                 1185

Glu Gly  Gly Asp Asn Lys Gly  Thr Tyr Cys Gly Ala  Pro Ile Leu
    1190                 1195                 1200
```

-continued

```
Gly Pro  Gly Asn Ala Pro Lys  Leu Ser Thr Lys Thr  Lys Phe Trp
    1205                 1210                 1215

Arg Ser  Ser Thr Val Pro Leu  Pro Pro Gly Thr Tyr  Glu Pro Ala
    1220                 1225                 1230

Tyr Leu  Gly Gly Lys Asp Pro  Arg Val Lys Gly Gly  Pro Ser Leu
    1235                 1240                 1245

Gln Gln  Val Met Arg Asp Gln  Leu Lys Pro Phe Thr  Glu Pro Arg
    1250                 1255                 1260

Gly Lys  Pro Pro Lys Pro Ser  Val Leu Glu Ala Ala  Lys Lys Thr
    1265                 1270                 1275

Ile Ile  Asn Val Leu Glu Gln  Thr Ile Asp Pro Pro  Gln Lys Trp
    1280                 1285                 1290

Ser Phe  Ser Gln Ala Cys Ala  Ser Leu Asp Lys Thr  Thr Ser Ser
    1295                 1300                 1305

Gly His  Pro His His Ile Arg  Lys Asn Asp Cys Trp  Asn Gly Glu
    1310                 1315                 1320

Ser Phe  Thr Gly Lys Leu Ala  Asp Gln Ala Ser Lys  Ala Asn Leu
    1325                 1330                 1335

Met Tyr  Glu Glu Gly Lys Asn  Met Thr Pro Val Tyr  Thr Gly Ala
    1340                 1345                 1350

Leu Lys  Asp Glu Leu Val Lys  Thr Asp Lys Ile Tyr  Gly Gln Ile
    1355                 1360                 1365

Lys Lys  Arg Leu Leu Trp Gly  Ser Asp Leu Ala Thr  Met Ile Arg
    1370                 1375                 1380

Cys Ala  Arg Ala Phe Gly Gly  Leu Met Asp Glu Leu  Lys Ala His
    1385                 1390                 1395

Cys Val  Thr Leu Pro Val Arg  Val Gly Met Asn Met  Asn Glu Asp
    1400                 1405                 1410

Gly Pro  Ile Ile Phe Glu Lys  His Ser Arg Phe Ser  Tyr His Tyr
    1415                 1420                 1425

Asp Ala  Asp Tyr Ser Arg Trp  Asp Ser Thr Gln Gln  Arg Ala Val
    1430                 1435                 1440

Leu Ala  Ala Ala Leu Glu Ile  Met Val Lys Phe Ser  Pro Glu Pro
    1445                 1450                 1455

His Leu  Ala Gln Ile Val Ala  Glu Asp Leu Leu Ala  Pro Ser Val
    1460                 1465                 1470

Met Asp  Val Gly Asp Phe Lys  Ile Thr Ile Asn Glu  Gly Leu Pro
    1475                 1480                 1485

Ser Gly  Val Pro Cys Thr Ser  Gln Trp Asn Ser Ile  Ala His Trp
    1490                 1495                 1500

Leu Leu  Thr Leu Cys Ala Leu  Ser Glu Val Thr Asn  Leu Ala Pro
    1505                 1510                 1515

Asp Ile  Ile Gln Ala Asn Ser  Leu Phe Ser Phe Tyr  Gly Asp Asp
    1520                 1525                 1530

Glu Ile  Val Ser Thr Asp Ile  Lys Leu Asp Pro Glu  Lys Leu Thr
    1535                 1540                 1545

Ala Lys  Leu Lys Glu Tyr Gly  Leu Lys Pro Thr Arg  Pro Asp Lys
    1550                 1555                 1560

Thr Glu  Gly Pro Leu Ile Ile  Ser Glu Asp Leu Asn  Gly Leu Thr
    1565                 1570                 1575

Phe Leu  Arg Arg Thr Val Thr  Arg Asp Pro Ala Gly  Trp Phe Gly
    1580                 1585                 1590
```

-continued

```
Lys Leu  Asp Gln Ser Ser Ile  Leu Arg Gln Ile Tyr  Trp Thr Arg
    1595                 1600                 1605

Gly Pro  Asn His Glu Asp Pro  Ser Glu Thr Met Ile  Pro His Ser
    1610                 1615                 1620

Gln Arg  Pro Ile Gln Leu Met  Ser Leu Leu Gly Glu  Ala Ala Leu
    1625                 1630                 1635

His Gly  Pro Thr Phe Tyr Thr  Lys Ile Ser Lys Leu  Val Ile Thr
    1640                 1645                 1650

Glu Leu  Lys Glu Gly Gly Met  Asp Phe Tyr Val Pro  Arg Gln Glu
    1655                 1660                 1665

Pro Met  Phe Arg Trp Met Arg  Phe Ser Asp Leu Ser  Thr Trp Glu
    1670                 1675                 1680

Gly Asp  Arg Asn Leu Ala Pro  Ser Phe Val Asn Glu  Asp Gly Val
    1685                 1690                 1695

Glu


<210> SEQ ID NO 27
<211> LENGTH: 542
<212> TYPE: PRT
<213> ORGANISM: Snow Mountain Virus

<400> SEQUENCE: 27

Met Lys Met Ala Ser Asn Asp Ala Ala Pro Ser Thr Asp Gly Ala Ala
1               5                   10                  15

Gly Leu Val Pro Glu Ser Asn Asn Glu Val Met Ala Leu Glu Pro Val
            20                  25                  30

Ala Gly Ala Ala Leu Ala Ala Pro Val Thr Gly Gln Thr Asn Ile Ile
        35                  40                  45

Asp Pro Trp Ile Arg Ala Asn Phe Val Gln Ala Pro Asn Gly Glu Phe
    50                  55                  60

Thr Val Ser Pro Arg Asn Ala Pro Gly Glu Val Leu Leu Asn Leu Glu
65                  70                  75                  80

Leu Gly Pro Glu Leu Asn Pro Tyr Leu Ala His Leu Ala Arg Met Tyr
                85                  90                  95

Asn Gly Tyr Ala Gly Gly Met Glu Val Gln Val Met Leu Ala Gly Asn
            100                 105                 110

Ala Phe Thr Ala Gly Lys Leu Val Phe Ala Ala Val Pro Pro His Phe
        115                 120                 125

Pro Val Glu Asn Leu Ser Pro Gln Gln Ile Thr Met Phe Pro His Val
    130                 135                 140

Ile Ile Asp Val Arg Thr Leu Glu Pro Val Leu Leu Pro Leu Pro Asp
145                 150                 155                 160

Val Arg Asn Asn Phe Phe His Tyr Asn Gln Lys Asp Asp Pro Lys Met
                165                 170                 175

Arg Ile Val Ala Met Leu Tyr Thr Pro Leu Arg Ser Asn Gly Ser Gly
            180                 185                 190

Asp Asp Val Phe Thr Val Ser Cys Arg Val Leu Thr Arg Pro Ser Pro
        195                 200                 205

Asp Phe Asp Phe Thr Tyr Leu Val Pro Pro Thr Val Glu Ser Lys Thr
    210                 215                 220

Lys Pro Phe Thr Leu Pro Ile Leu Thr Leu Gly Glu Leu Ser Asn Ser
225                 230                 235                 240

Arg Phe Pro Val Ser Ile Asp Gln Met Tyr Thr Ser Pro Asn Glu Val
                245                 250                 255
```

-continued

```
Ile Ser Val Gln Cys Gln Asn Gly Arg Cys Thr Leu Asp Gly Glu Leu
            260                 265                 270

Gln Gly Thr Thr Gln Leu Gln Val Ser Gly Ile Cys Ala Phe Lys Gly
        275                 280                 285

Glu Val Thr Ala His Leu Gln Asp Asn Asp His Leu Tyr Asn Ile Thr
    290                 295                 300

Ile Thr Asn Leu Asn Gly Ser Pro Phe Asp Pro Ser Glu Asp Ile Pro
305                 310                 315                 320

Ala Pro Leu Gly Val Pro Asp Phe Gln Gly Arg Val Phe Gly Val Ile
                325                 330                 335

Thr Gln Arg Asp Lys Gln Asn Ala Ala Gly Gln Ser Gln Pro Ala Asn
            340                 345                 350

Arg Gly His Asp Ala Val Val Pro Thr Tyr Thr Ala Gln Tyr Thr Pro
        355                 360                 365

Lys Leu Gly Gln Val Gln Ile Gly Thr Trp Gln Thr Asp Asp Leu Lys
    370                 375                 380

Val Asn Gln Pro Val Lys Phe Thr Pro Val Gly Leu Asn Asp Thr Glu
385                 390                 395                 400

His Phe Asn Gln Trp Val Val Pro Arg Tyr Ala Gly Ala Leu Asn Leu
                405                 410                 415

Asn Thr Asn Leu Ala Pro Ser Val Ala Pro Val Phe Pro Gly Glu Arg
            420                 425                 430

Leu Leu Phe Phe Arg Ser Tyr Leu Pro Leu Lys Gly Gly Tyr Gly Asn
        435                 440                 445

Pro Ala Ile Asp Cys Leu Leu Pro Gln Glu Trp Val Gln His Phe Tyr
    450                 455                 460

Gln Glu Ala Ala Pro Ser Met Ser Glu Val Ala Leu Val Arg Tyr Ile
465                 470                 475                 480

Asn Pro Asp Thr Gly Arg Ala Leu Phe Glu Ala Lys Leu His Arg Ala
                485                 490                 495

Gly Phe Met Thr Val Ser Ser Asn Thr Ser Ala Pro Val Val Val Pro
            500                 505                 510

Ala Asn Gly Tyr Phe Arg Phe Asp Ser Trp Val Asn Gln Phe Tyr Ser
        515                 520                 525

Leu Ala Pro Met Gly Thr Gly Asn Gly Arg Arg Arg Ile Gln
    530                 535                 540


<210> SEQ ID NO 28
<211> LENGTH: 259
<212> TYPE: PRT
<213> ORGANISM: Snow Mountain Virus

<400> SEQUENCE: 28

Met Ala Gly Ala Phe Val Ala Gly Leu Ala Gly Asp Val Leu Ser Asn
1               5                   10                  15

Gly Leu Ser Ser Leu Ile Asn Ala Gly Ala Asn Ala Ile Asn Gln Arg
            20                  25                  30

Ala Glu Phe Asp Phe Asn Gln Lys Leu Gln Gln Asn Ser Phe Asn His
        35                  40                  45

Asp Lys Glu Met Leu Gln Ala Gln Ile Gln Ala Thr Lys Gln Leu Gln
    50                  55                  60

Ala Asp Met Met Ala Ile Lys Gln Gly Val Leu Thr Ala Gly Gly Phe
65                  70                  75                  80

Ser Pro Thr Asp Ala Ala Arg Gly Ala Val Asn Ala Pro Met Thr Gln
                85                  90                  95
```

-continued

Ala Leu Asp Trp Asn Gly Thr Arg Tyr Trp Ala Pro Gly Ser Met Arg
100 105 110

Thr Thr Ser Tyr Ser Gly Arg Phe Thr Ser Thr Ala Pro Ala Arg Gln
115 120 125

Ala Asp Leu Gln His Thr Gln Asn Arg Pro Ser Ser Gly Ser Ser Val
130 135 140

Ser Ser Tyr Ala Thr Gln Ser Ser Arg Pro Thr Leu Thr Thr Thr Thr
145 150 155 160

Gly Ser Ser His Ser Thr Thr Ser Ser Asn Ser Thr Arg Ser Thr Asn
165 170 175

Leu Ser Gln Ser Thr Val Ser Arg Ala Ala Ser Arg Thr Ser Glu Trp
180 185 190

Val Arg Asp Gln Asn Arg Asn Leu Glu Pro Tyr Met His Gly Ala Leu
195 200 205

Gln Thr Ala Phe Val Thr Pro Pro Ser Ser Arg Ala Ser Asp Gly Thr
210 215 220

Val Ser Thr Val Pro Lys Gly Val Leu Asp Ser Trp Thr Pro Ala Phe
225 230 235 240

Asn Thr Arg Arg Gln Pro Leu Phe Ala His Leu Arg Lys Arg Gly Glu
245 250 255

Ser Gln Ala

<210> SEQ ID NO 29
<211> LENGTH: 7537
<212> TYPE: DNA
<213> ORGANISM: Snow Mountain Virus

<400> SEQUENCE: 29
gtgaatgaag atggcgtcta acgacgcttc cgctgccgct gctgtcaaca gcaacaacga 60
caacgcaaaa tcttcaagtg acggagtact atctagtatg gctgtcactt ttaaacgagc 120
ccttggggcc cggcctaaac agccgccccc gagggaaata ccacaaaggc ccccaaggcc 180
acccacccca gaactggtga aaaagatccc acctcccccg cccaacggag aagacgaacc 240
ggtcgttcat tatagtgcta aagatggcat aactgggctg cccgaactta caacagtgag 300
gcagccagaa gaggccgcta cagcattcag cgtcccaccc ctcgaccaga gagagaatag 360
ggacgctaaa gagccattga ccggcaccat cttggagatg tgggatggcg agatttacca 420
ttatggccta tatgtggagc gagggctggt gcttggcgtg cacaaaccac cagccgccat 480
cagcctcgct aaagttgagt taacacctct atctttgtat tggagaccag tgtacacccc 540
ccagtacctc atcgctcctg acaccctcag gaaactgcac ggggagttat ttccatacac 600
ggcctttgat aacaactgct atgccttctg ctgctgggtg ttggacttaa acgattcttg 660
gttgagcaga aggatgatac agagaacaac tggctttttc aggccttacc aagattggaa 720
taggaagccc ctccccacca tggatgactc caagttgaag aaggtggcca acatactttt 780
gtgtgccttg tcatcactat tcactagacc catcaaggac ataattggga aactcaggcc 840
tctcaatatc cttaacatcc tggcttcttg tgattggact ttcgcaggta tagtggaatc 900
tctaattctc ctagctgaac tcttcggagt tttctggaca cccccagatg tgtctgcgat 960
gatcgccccc ttactgggtg actacgagct gcaaggaccc gaagatcttg ctgtggaact 1020
tgtaccgata gtaatggggg ggataggatt ggtgttgggg ttcaccaagg aaaagattgg 1080
gaagatgctg tcatctgccg cttccaccct gaggacctgc aaagaccttg gcgcctatgg 1140
gctggaaatt ctgaaactgg tcatgaaatg gtttttccca aagaaagaag aggcaaacga 1200

-continued

```
gcttgcgatg gtgagggcta ttgaggacgc agtcctagat ctcgaggcta ttgagaacaa   1260

ccatatgaca gctctactca aagacaaaga tagcctcgcg acatacatga ggactcttga   1320

tttggaggaa gaaaaggcca gaaagctctc cactaagtcc gcttcacctg atatagtggg   1380

cacgatcaac gccctgctgg ctagaattgc cgctgctcgt tcccttgtac acagggccaa   1440

ggaagaactg tccagcaggc taaggccagt tgttgtgatg atatctggca aacctggcat   1500

cgggaagacc catctggcta gagaattggc aaagaagatc gctataaccc tttcaggaga   1560

ccagagggta ggcctcatcc cccgcaacgg agtcgaccac tgggatgctt acaagggtga   1620

gagagtcgtt ctctgggacg attatgggat gagtaacccc gtccatgatg ccctaagact   1680

ccaagaactt gctgacacct gccctttgac cctaaactgt gacagaattg agaacaaggg   1740

caaggtcttt gacagtgatg ccataatcat cacaaccaac ctggctaacc cagctccact   1800

tgattatgtc aactttgaag cttgctccag gcgcattgac ttccttgtgt atgccgatgc   1860

acctgacgtt gagaaagcga agcgcgactt cccgggacaa cctgacatgt ggaagagcgc   1920

ttatagtccc gacttctcac acatcaagct aatgctggct ccccagggtg gttttgacaa   1980

aaatggcaac accccacacg ggaaaggtgt catgaagacc ctcacaacag gctccctcat   2040

tgcccgtgct tcagggctcc tccatgaacg attggatgaa ttcgaactac aaggacccaa   2100

cctcacaact ttcaactttg accgtaataa aatacaggct tttaggcagc ttgccgctga   2160

aaacaaatat ggcctggtgg acacaatgag agtgggtgga caactcaagg gtgtcagaac   2220

tataccagaa ctcaagcagg ccctcaagaa catattaatc aaaaggtgcc agatagtgta   2280

tggtggcagc acctatacac ttgaatctga tggcaaaggg aatgtgaaag tggaaaaagt   2340

gcaaaatacc aacatccaaa tcaacaacga gctagctggt gctttacacc acctccgatg   2400

cgctaggatc aggtactatg ttaaatgtgt tcaggaggct ctatattcca tcatccaaat   2460

tgctggggcc gcgtttgtaa ccacgcgcat tgtgaagcgc atgaacatac aaaacttgtg   2520

gtcaaggcct ccagtaggag atgcggagga ggtcactagc caggatggtt gcccaaagcc   2580

caaagatgat gaggagttcg tcatctcgtc tagtgacatc acgcctgaag gcaagaaagg   2640

aaagaacaag actggccgcg gcaagaaaca cacagccttc tcgagcaagg gtctcagtga   2700

tgaggagtac gatgagtaca aaagaatcag ggaagaaagg aatggtaagt actccataga   2760

agaatacctt caggacagag acaagtatta tgaggaagtg gccatagcca gggcaactga   2820

ggaagacttc tgtgaggaag aagaagccaa gatccgacag aggatattta ggccaacgag   2880

gaagcaacgc aaggaggaga gggcttccct tggccttgtc actggctcag agatcagaaa   2940

gagaaaccca gacgacttca aacctaaagg aaagctgtgg gctgatgatg aaagggtcgt   3000

tgactataat gagaaactca gttttgaggc ccccccgagc atctggtcaa ggatagtcaa   3060

ctttgggtca ggatgggggt tctgggtgtc ccctagcctg tttattacat caacccatgt   3120

tataccccaa ggcactcagg aattctttgg tgtacccatc aagcagattc agattcacaa   3180

atcaggggag ttctgccgcc tgagattccc taaatcaatc agaactgctg taacaggcat   3240

gatcctagaa gagggggccc cagaaggaac cgtggtctca ctactcatca agagaccaac   3300

cggtgagctc atgcccctgg cagccagaat gggcacccat gcgactatga aaatccaagg   3360

tcgcacggtt ggaggtcaga tgggtatgtt gctaacaggg tccaatgcta aaagcatgga   3420

tttgggcacg acacctggtg actgtggctg cccctatatt tataagagag gcaatgacta   3480

cgtggtcatc ggcgtgcaca cagccgctgc tcgcggaggt aacactgtca tctgtgcaac   3540

ccagggcagt gaaggtgagg ccacgctcga aggcggtgat aacaaaggca cctactgtgg   3600
```

-continued

```
agctccaata ctaggccctg gtaacgctcc caagctcagc accaagacta aattctggag   3660
gtcctccaca gtgccactcc cacccgggac ctatgaacca gcttacttag gtggcaagga   3720
ccccagggtg aagggtggac cttcactaca acaagtcatg agagaccagc taaaaccatt   3780
cactgagcct aggggcaaac cacccaagcc aagtgtgctg gaagctgcca agaagaccat   3840
tatcaatgtg ttggagcaaa caatagatcc cccccaaaaa tggtcatttt cacaagcatg   3900
tgcgtcgctt gataaaacca cctccagcgg ccaccccccac cacatacgga agaacgattg   3960
ctggaatggg gagtctttta caggaaaatt ggcagatcaa gcatcaaaag ctaacctaat   4020
gtatgaggaa ggaaagaaca tgaccccagt ctacacaggg gccctcaagg atgagctggt   4080
caagactgac aagatctatg ggcagatcaa gaaaaggctt ctttggggct ctgacttggc   4140
aacaatgatc cgttgtgcgc gggcgtttgg agggttaatg gatgagctca aggcccattg   4200
cgtaacactc cctgtcaggg ttgggatgaa catgaatgag gatggaccca taatttttga   4260
aaagcactcc aggttctcat accactatga tgcagattac tcacgctggg actcaaccca   4320
acagagggca gtgctagctg cagccttgga aatcatggta aaattctcac cagaaccaca   4380
tttggcccaa attgttgcag aggatctcct agcccccagt gtgatggatg taggtgattt   4440
caaaataaca attaatgagg gactgccctc gggagtaccc tgcacatcac agtggaattc   4500
catcgcccac tggctcctca cactctgcgc actatctgaa gtcacaaacc tggctcctga   4560
catcatacaa gctaactcct tgttctcttt ctatggtgat gatgaaatcg taagtactga   4620
cataaaatta gacccagaga aactcacagc aaaactcaaa gaatacggac tcaaaccaac   4680
ccgcccggac aaaactgaag gacccctgat catatccgag gacttgaatg gtttgacctt   4740
tctgcggcgg accgtgaccc gtgatccagc tgggtggttt ggcaagttgg accagagttc   4800
aattctcagg cagatatact ggactagggg ccccaaccat gaggacccgt ccgaaacaat   4860
gataccacac tcccagaggc ctatacagct gatgtctctt ttgggtgaag cagccttgca   4920
tggtccaaca ttttacacca aaatcagtaa actggtcatc acagagctga aggaaggtgg   4980
catggatttt tacgtgccca gacaggaacc catgttcagg tggatgagat tctcagattt   5040
gagcacgtgg gagggcgatc gcaatctggc tcccagtttt gtgaatgaag atggcgtcga   5100
atgacgccgc tccatctact gatggtgcag ccggcctcgt gccagaaagt aataatgagg   5160
tcatggctct tgagcccgtg gctggtgctg ccttggcagc cccggtcacc ggtcaaacaa   5220
atattataga cccttggatt agagcaaatt ttgtccaggc ccctaatggt gaatttacag   5280
tttctccccg taatgcccct ggtgaagtgc tattaaatct agaattgggt ccagaattaa   5340
atccttatct ggcacattta gcaagaatgt acaacgggta tgccggtggg atggaggtgc   5400
aggtcatgct agctgggaac gcgttcacag ctggcaaatt ggtcttcgct gctgtaccac   5460
ctcatttccc ggttgaaaac cttagtccac agcaaattac catgttccct catgtgatta   5520
tagatgttag gactttggaa cctgttttat tgccactccc cgatgttaga aataatttct   5580
tccattataa tcaaaaagat gatcctaaga tgagaattgt ggctatgctt tatactcccc   5640
tcaggtccaa tggttctggt gatgatgtgt tcacagtctc ttgcagggtg ttgactagac   5700
cctcccctga ttttgatttt acatacctgg taccaccaac agtggaatcc aaaacaaaac   5760
cattcaccct tccaattctt acacttgggg agctttccaa ttctagattt ccagtgtcca   5820
tagatcagat gtacactagc cccaatgaag tcatatctgt gcagtgccag aatggaaggt   5880
gcacactgga tggggagctc caaggaacaa cacagctcca agttagtggc atttgtgcat   5940
tcaaaggaga agtgaccgct cacttgcagg acaatgatca cctatacaac atcaccatca   6000
```

-continued

```
caaacttgaa tgggtcccct tttgatccct ctgaggacat ccccgccccc ctgggtgtgc   6060
ccgactttca gggaagagtc tttggtgtca tcactcaaag agacaaacag aatgccgctg   6120
ggcaaagcca gccggcaaac aggggacacg atgctgtggt ccccacttac acagcccagt   6180
ataccccaaa attgggtcag gttcaaattg gcacatggca gaccgacgat cttaaagtca   6240
accaaccagt caaattcacc ccagtcggtc tcaatgacac agaacatttc aatcagtggg   6300
tggtccctag gtacgctggt gctttaaatc taaacacaaa tcttgccccc tctgttgctc   6360
cagtgtttcc aggggagcgt ctgctcttct ttagatcata cctccccctt aagggtggtt   6420
atggaaaccc agctattgat tgcctgctac cacaagagtg ggtgcagcat ttttatcagg   6480
aagcagcccc ctcaatgagt gaggtagccc ttgtcagata catcaatccg gacactggcc   6540
gggcgctgtt tgaggccaaa ctccacagag ctggtttcat gacagtctcg agtaacacca   6600
gtgctccggt ggttgtgcct gccaacggat acttcagatt tgactcttgg gtgaaccaat   6660
tttattctct tgcccccatg ggaactggaa atgggcgtag aaggattcag tgatggctgg   6720
agcttttgta gctggtctcg cgggggatgt gctcagcaat gggctcagct cactaattaa   6780
tgcaggtgct aatgcaataa atcagagagc agaatttgat tttaatcaga aattacagca   6840
aaattctttt aatcatgata aggagatgtt gcaggctcag attcaggcaa ctaagcagct   6900
gcaggcagac atgatggcta taaagcaggg ggttctgacc gctggcggct tttcccctac   6960
tgatgcagcc agaggcgctg tgaacgcgcc catgacacag gcgctggatt ggaatggcac   7020
aaggtattgg gcaccaggct ccatgaggac tacatcctac tctgggaggt tcacatcgac   7080
cgccccggca aggcaggccg atcttcaaca cactcaaaat cggccttcga gtggctcttc   7140
tgtgtcctct tatgccactc aatcttcaag accaactcta accacaacca cagggtcctc   7200
acatagtaca acctcatcca attcgacccg tagcacaaac ctttcccagt cgacggtctc   7260
tagggctgca tccaggacta gtgagtgggt tagagatcaa aatagaaatt tggaacccta   7320
catgcatggt gccttacaga cagcctttgt caccccacct tccagcaggg catctgacgg   7380
gacagtctca accgtcccca aaggtgtttt ggactcctgg acacctgcgt tcaacacccg   7440
caggcagccg ctttttgcac acctccgtaa gaggggggag tcacaagctt agtgaaaagg   7500
tgaaaaattt actttaaatg aattgattct acctttt                            7537
```

<210> SEQ ID NO 30
<211> LENGTH: 1629
<212> TYPE: DNA
<213> ORGANISM: Snow Mountain Virus

<400> SEQUENCE: 30

```
atgaagatgg cgtcgaatga cgccgctcca tctactgatg gtgcagccgg cctcgtgcca     60
gaaagtaata atgaggtcat ggctcttgag cccgtggctg gtgctgcctt ggcagccccg    120
gtcaccggtc aaacaaatat tatagaccct tggattagag caaattttgt ccaggcccct    180
aatggtgaat ttacagtttc tccccgtaat gcccctggtg aagtgctatt aaatctagaa    240
ttgggtccag aattaaatcc ttatctggca catttagcaa gaatgtacaa cgggtatgcc    300
ggtgggatgg aggtgcaggt catgctagct gggaacgcgt tcacagctgg caaattggtc    360
ttcgctgctg taccacctca tttcccggtt gaaaacctta gtccacagca aattaccatg    420
ttccctcatg tgattataga tgttaggact ttggaacctg ttttattgcc actccccgat    480
gttagaaata atttcttcca ttataatcaa aaagatgatc ctaagatgag aattgtggct    540
atgctttata ctcccctcag gtccaatggt tctggtgatg atgtgttcac agtctcttgc    600
```

-continued agggtgttga ctagaccctc ccctgatttt gattttacat acctggtacc accaacagtg 660
gaatccaaaa caaaaccatt cacccttcca attcttacac ttggggagct ttccaattct 720
agatttccag tgtccataga tcagatgtac actagcccca atgaagtcat atctgtgcag 780
tgccagaatg gaaggtgcac actggatggg gagctccaag gaacaacaca gctccaagtt 840
agtggcattt gtgcattcaa aggagaagtg accgctcact tgcaggacaa tgatcaccta 900
tacaacatca ccatcacaaa cttgaatggg tccccttttg atccctctga ggacatcccc 960
gcccccctgg gtgtgcccga ctttcaggga agagtctttg gtgtcatcac tcaaagagac 1020
aaacagaatg ccgctgggca aagccagccg gcaaacaggg gacacgatgc tgtggtcccc 1080
acttacacag cccagtatac ccccaaaattg ggtcaggttc aaattggcac atggcagacc 1140
gacgatctta aagtcaacca accagtcaaa ttcaccccag tcggtctcaa tgacacagaa 1200
catttcaatc agtgggtggt ccctaggtac gctggtgctt taaatctaaa cacaaatctt 1260 gcccccctctg ttgctccagt gtttccaggg gagcgtctgc tcttctttag atcataccte 1320 ccccttaagg gtggttatgg aaacccagct attgattgcc tgctaccaca agagtgggtg 1380
cagcattttt atcaggaagc agccccctca atgagtgagg tagcccttgt cagatacatc 1440
aatccggaca ctggccgggc gctgtttgag gccaaactcc acagagctgg tttcatgaca 1500
gtctcgagta acaccagtgc tccggtggtt gtgcctgcca acggatactt cagatttgac 1560
tcttgggtga accaatttta ttctcttgcc cccatgggaa ctggaaatgg gcgtagaagg 1620
attcagtga 1629

<210> SEQ ID NO 31
<211> LENGTH: 780
<212> TYPE: DNA
<213> ORGANISM: Snow Mountain Virus

<400> SEQUENCE: 31
atggctggag cttttgtagc tggtctcgcg ggggatgtgc tcagcaatgg gctcagctca 60
ctaattaatg caggtgctaa tgcaataaat cagagagcag aatttgattt taatcagaaa 120
ttacagcaaa attcttttaa tcatgataag gagatgttgc aggctcagat tcaggcaact 180
aagcagctgc aggcagacat gatggctata aagcaggggg ttctgaccgc tggcggcttt 240
tcccctactg atgcagccag aggcgctgtg aacgcgccca tgacacaggc gctggattgg 300
aatggcacaa ggtattgggc accaggctcc atgaggacta catcctactc tgggaggttc 360
acatcgaccg ccccggcaag gcaggccgat cttcaacaca ctcaaaatcg gccttcgagt 420
ggctcttctg tgtcctctta tgccactcaa tcttcaagac caactctaac cacaaccaca 480
gggtcctcac atagtacaac ctcatccaat tcgacccgta gcacaaacct ttcccagtcg 540
acggtctcta gggctgcatc caggactagt gagtgggtta gagatcaaaa tagaaatttg 600
gaaccctaca tgcatggtgc cttacagaca gcctttgtca ccccaccttc cagcagggca 660
tctgacggga cagtctcaac cgtccccaaa ggtgttttgg actcctggac acctgcgttc 720
aacacccgca ggcagccgct tttgcacac ctccgtaaga ggggggagtc acaagcttag 780

<210> SEQ ID NO 32
<211> LENGTH: 5100
<212> TYPE: PRT
<213> ORGANISM: Snow Mountain Virus -continued

<400> SEQUENCE: 32

Ala Thr Gly Ala Ala Gly Ala Thr Gly Gly Cys Gly Thr Cys Thr Ala
1 5 10 15

Ala Cys Gly Ala Cys Gly Cys Thr Thr Cys Cys Gly Cys Thr Gly Cys
20 25 30

Cys Gly Cys Thr Gly Cys Thr Gly Thr Cys Ala Ala Cys Ala Gly Cys
35 40 45

Ala Ala Cys Ala Ala Cys Gly Ala Cys Ala Ala Cys Gly Cys Ala Ala
50 55 60

Ala Ala Thr Cys Thr Thr Cys Ala Ala Gly Thr Gly Ala Cys Gly Gly
65 70 75 80

Ala Gly Thr Ala Cys Thr Ala Thr Cys Thr Ala Gly Thr Ala Thr Gly
85 90 95

Gly Cys Thr Gly Thr Cys Ala Cys Thr Thr Thr Thr Ala Ala Ala Cys
100 105 110

Gly Ala Gly Cys Cys Cys Thr Thr Gly Gly Gly Gly Cys Cys Cys Gly
115 120 125

Gly Cys Cys Thr Ala Ala Ala Cys Ala Gly Cys Cys Gly Cys Cys Cys
130 135 140

Cys Cys Gly Ala Gly Gly Gly Ala Ala Ala Thr Ala Cys Cys Ala Cys
145 150 155 160

Ala Ala Ala Gly Gly Cys Cys Cys Cys Cys Ala Ala Gly Gly Cys Cys
165 170 175

Ala Cys Cys Cys Ala Cys Cys Cys Cys Ala Gly Ala Ala Cys Thr Gly
180 185 190

Gly Thr Gly Ala Ala Ala Ala Ala Gly Ala Thr Cys Cys Cys Ala Cys
195 200 205

Cys Thr Cys Cys Cys Cys Cys Gly Cys Cys Cys Ala Ala Cys Gly Gly
210 215 220

Ala Gly Ala Ala Gly Ala Cys Gly Ala Ala Cys Cys Gly Gly Thr Cys
225 230 235 240

Gly Thr Thr Cys Ala Thr Thr Ala Thr Ala Gly Thr Gly Cys Thr Ala
245 250 255

Ala Ala Gly Ala Thr Gly Gly Cys Ala Thr Ala Ala Cys Thr Gly Gly
260 265 270

Gly Cys Thr Gly Cys Cys Cys Gly Ala Ala Cys Thr Thr Ala Cys Ala
275 280 285

Ala Cys Ala Gly Thr Gly Ala Gly Gly Cys Ala Gly Cys Cys Ala Gly
290 295 300

Ala Ala Gly Ala Gly Gly Cys Cys Gly Cys Thr Ala Cys Ala Gly Cys
305 310 315 320

Ala Thr Thr Cys Ala Gly Cys Gly Thr Cys Cys Cys Ala Cys Cys Cys
325 330 335

Cys Thr Cys Gly Ala Cys Cys Ala Gly Ala Gly Ala Gly Ala Gly Ala
340 345 350

Ala Thr Ala Gly Gly Gly Ala Cys Gly Cys Thr Ala Ala Ala Gly Ala
355 360 365

Gly Cys Cys Ala Thr Thr Gly Ala Cys Cys Gly Gly Cys Ala Cys Cys
370 375 380

Ala Thr Cys Thr Thr Gly Gly Ala Gly Ala Thr Gly Thr Gly Gly Gly
385 390 395 400

Ala Thr Gly Gly Cys Gly Ala Gly Ala Thr Thr Thr Ala Cys Cys Ala
405 410 415

-continued

```
Thr Thr Ala Thr Gly Gly Cys Cys Thr Ala Thr Ala Thr Gly Thr Gly
            420                 425                 430

Gly Ala Gly Cys Gly Ala Gly Gly Gly Cys Thr Gly Gly Thr Gly Cys
        435                 440                 445

Thr Thr Gly Gly Cys Gly Thr Gly Cys Ala Cys Ala Ala Ala Cys Cys
    450                 455                 460

Ala Cys Cys Ala Gly Cys Cys Gly Cys Cys Ala Thr Cys Ala Gly Cys
465                 470                 475                 480

Cys Thr Cys Gly Cys Thr Ala Ala Ala Gly Thr Thr Gly Ala Gly Thr
                485                 490                 495

Thr Ala Ala Cys Ala Cys Cys Thr Cys Thr Ala Thr Cys Thr Thr Thr
            500                 505                 510

Gly Thr Ala Thr Thr Gly Gly Ala Gly Ala Cys Cys Ala Gly Thr Gly
        515                 520                 525

Thr Ala Cys Ala Cys Cys Cys Cys Cys Cys Ala Gly Thr Ala Cys Cys
    530                 535                 540

Thr Cys Ala Thr Cys Gly Cys Thr Cys Cys Thr Gly Ala Cys Ala Cys
545                 550                 555                 560

Cys Cys Thr Cys Ala Gly Gly Ala Ala Ala Cys Thr Gly Cys Ala Cys
                565                 570                 575

Gly Gly Gly Gly Ala Gly Thr Thr Ala Thr Thr Thr Cys Cys Ala Thr
            580                 585                 590

Ala Cys Ala Cys Gly Gly Cys Cys Thr Thr Thr Gly Ala Thr Ala Ala
        595                 600                 605

Cys Ala Ala Cys Thr Gly Cys Thr Ala Thr Gly Cys Cys Thr Thr Cys
    610                 615                 620

Thr Gly Cys Thr Gly Cys Thr Gly Gly Gly Thr Gly Thr Thr Gly Gly
625                 630                 635                 640

Ala Cys Thr Thr Ala Ala Ala Cys Gly Ala Thr Thr Cys Thr Thr Gly
                645                 650                 655

Gly Thr Thr Gly Ala Gly Cys Ala Gly Ala Ala Gly Gly Ala Thr Gly
            660                 665                 670

Ala Thr Ala Cys Ala Gly Ala Gly Ala Ala Cys Ala Ala Cys Thr Gly
        675                 680                 685

Gly Cys Thr Thr Thr Thr Thr Cys Ala Gly Gly Cys Cys Thr Thr Ala
    690                 695                 700

Cys Cys Ala Ala Gly Ala Thr Thr Gly Gly Ala Ala Thr Ala Gly Gly
705                 710                 715                 720

Ala Ala Gly Cys Cys Cys Cys Thr Cys Cys Cys Cys Ala Cys Cys Ala
                725                 730                 735

Thr Gly Gly Ala Thr Gly Ala Cys Thr Cys Cys Ala Ala Gly Thr Thr
            740                 745                 750

Gly Ala Ala Gly Ala Ala Gly Gly Thr Gly Gly Cys Cys Ala Ala Cys
        755                 760                 765

Ala Thr Ala Cys Thr Thr Thr Thr Gly Thr Gly Thr Gly Cys Cys Thr
    770                 775                 780

Thr Gly Thr Cys Ala Thr Cys Ala Cys Thr Ala Thr Thr Cys Ala Cys
785                 790                 795                 800

Thr Ala Gly Ala Cys Cys Cys Ala Thr Cys Ala Ala Gly Gly Ala Cys
                805                 810                 815

Ala Thr Ala Ala Thr Thr Gly Gly Gly Ala Ala Ala Cys Thr Cys Ala
            820                 825                 830
```

-continued

```
Gly Gly Cys Cys Thr Cys Thr Cys Ala Ala Thr Ala Thr Cys Cys Thr
        835                 840                 845

Thr Ala Ala Cys Ala Thr Cys Cys Thr Gly Gly Cys Thr Thr Cys Thr
    850                 855                 860

Thr Gly Thr Gly Ala Thr Thr Gly Gly Ala Cys Thr Thr Thr Cys Gly
865                 870                 875                 880

Cys Ala Gly Gly Thr Ala Thr Ala Gly Thr Gly Gly Ala Ala Thr Cys
                885                 890                 895

Thr Cys Thr Ala Ala Thr Thr Cys Thr Cys Cys Thr Ala Gly Cys Thr
            900                 905                 910

Gly Ala Ala Cys Thr Cys Thr Thr Cys Gly Gly Ala Gly Thr Thr Thr
        915                 920                 925

Thr Cys Thr Gly Gly Ala Cys Ala Cys Cys Cys Cys Cys Ala Gly Ala
    930                 935                 940

Thr Gly Thr Gly Thr Cys Thr Gly Cys Gly Ala Thr Gly Ala Thr Cys
945                 950                 955                 960

Gly Cys Cys Cys Cys Cys Thr Thr Ala Cys Thr Gly Gly Gly Thr Gly
                965                 970                 975

Ala Cys Thr Ala Cys Gly Ala Gly Cys Thr Gly Cys Ala Ala Gly Gly
            980                 985                 990

Ala Cys Cys Cys Gly Ala Ala Gly  Ala Thr Cys Thr Thr  Gly Cys Thr
        995                 1000                1005

Gly Thr  Gly Gly Ala Ala Cys  Thr Thr Gly Thr Ala  Cys Cys Gly
    1010                1015                1020

Ala Thr  Ala Gly Thr Ala Ala  Thr Gly Gly Gly Gly  Gly Gly Gly
    1025                1030                1035

Ala Thr  Ala Gly Gly Ala Thr  Thr Gly Gly Thr Gly  Thr Thr Gly
    1040                1045                1050

Gly Gly  Gly Thr Thr Cys Ala  Cys Cys Ala Ala Gly  Gly Ala Ala
    1055                1060                1065

Ala Ala  Gly Ala Thr Thr Gly  Gly Gly Ala Ala Gly  Ala Thr Gly
    1070                1075                1080

Cys Thr  Gly Thr Cys Ala Thr  Cys Thr Gly Cys Cys  Gly Cys Thr
    1085                1090                1095

Thr Cys  Cys Ala Cys Cys Cys  Thr Gly Ala Gly Gly  Ala Cys Cys
    1100                1105                1110

Thr Gly  Cys Ala Ala Ala Gly  Ala Cys Cys Thr Thr  Gly Gly Cys
    1115                1120                1125

Gly Cys  Cys Thr Ala Thr Gly  Gly Gly Cys Thr Gly  Gly Ala Ala
    1130                1135                1140

Ala Thr  Thr Cys Thr Gly Ala  Ala Ala Cys Thr Gly  Gly Thr Cys
    1145                1150                1155

Ala Thr  Gly Ala Ala Ala Thr  Gly Gly Thr Thr Thr  Thr Thr Cys
    1160                1165                1170

Cys Cys  Ala Ala Ala Gly Ala  Ala Ala Gly Ala Ala  Gly Ala Gly
    1175                1180                1185

Gly Cys  Ala Ala Ala Cys Gly  Ala Gly Cys Thr Thr  Gly Cys Gly
    1190                1195                1200

Ala Thr  Gly Gly Thr Gly Ala  Gly Gly Gly Cys Thr  Ala Thr Thr
    1205                1210                1215

Gly Ala  Gly Gly Ala Cys Gly  Cys Ala Gly Thr Cys  Cys Thr Ala
    1220                1225                1230
```

-continued

```
Gly Ala  Thr Cys Thr Cys Gly  Ala Gly Gly Cys Thr  Ala Thr Thr
    1235                 1240                 1245

Gly Ala  Gly Ala Ala Cys Ala  Ala Cys Cys Ala Thr  Ala Thr Gly
    1250                 1255                 1260

Ala Cys  Ala Gly Cys Thr Cys  Thr Ala Cys Thr Cys  Ala Ala Ala
    1265                 1270                 1275

Gly Ala  Cys Ala Ala Ala Gly  Ala Thr Ala Gly Cys  Cys Thr Cys
    1280                 1285                 1290

Gly Cys  Gly Ala Cys Ala Thr  Ala Cys Ala Thr Gly  Ala Gly Gly
    1295                 1300                 1305

Ala Cys  Thr Cys Thr Thr Gly  Ala Thr Thr Thr Gly  Gly Ala Gly
    1310                 1315                 1320

Gly Ala  Ala Gly Ala Ala Ala  Ala Gly Gly Cys Cys  Ala Gly Ala
    1325                 1330                 1335

Ala Ala  Gly Cys Thr Cys Thr  Cys Cys Ala Cys Thr  Ala Ala Gly
    1340                 1345                 1350

Thr Cys  Cys Gly Cys Thr Thr  Cys Ala Cys Cys Thr  Gly Ala Thr
    1355                 1360                 1365

Ala Thr  Ala Gly Thr Gly Gly  Gly Cys Ala Cys Gly  Ala Thr Cys
    1370                 1375                 1380

Ala Ala  Cys Gly Cys Cys Cys  Thr Gly Cys Thr Gly  Gly Cys Thr
    1385                 1390                 1395

Ala Gly  Ala Ala Thr Thr Gly  Cys Cys Gly Cys Thr  Gly Cys Thr
    1400                 1405                 1410

Cys Gly  Thr Thr Cys Cys Cys  Thr Thr Gly Thr Ala  Cys Ala Cys
    1415                 1420                 1425

Ala Gly  Gly Gly Cys Cys Ala  Ala Gly Gly Ala Ala  Gly Ala Ala
    1430                 1435                 1440

Cys Thr  Gly Thr Cys Cys Ala  Gly Cys Ala Gly Gly  Cys Thr Ala
    1445                 1450                 1455

Ala Gly  Gly Cys Cys Ala Gly  Thr Thr Gly Thr Thr  Gly Thr Gly
    1460                 1465                 1470

Ala Thr  Gly Ala Thr Ala Thr  Cys Thr Gly Gly Cys  Ala Ala Ala
    1475                 1480                 1485

Cys Cys  Thr Gly Gly Cys Ala  Thr Cys Gly Gly Gly  Ala Ala Gly
    1490                 1495                 1500

Ala Cys  Cys Cys Ala Thr Cys  Thr Gly Gly Cys Thr  Ala Gly Ala
    1505                 1510                 1515

Gly Ala  Ala Thr Thr Gly Gly  Cys Ala Ala Ala Gly  Ala Ala Gly
    1520                 1525                 1530

Ala Thr  Cys Gly Cys Thr Ala  Thr Ala Ala Cys Cys  Cys Thr Thr
    1535                 1540                 1545

Thr Cys  Ala Gly Gly Ala Gly  Ala Cys Cys Ala Gly  Ala Gly Gly
    1550                 1555                 1560

Gly Thr  Ala Gly Gly Cys Cys  Thr Cys Ala Thr Cys  Cys Cys Cys
    1565                 1570                 1575

Cys Gly  Cys Ala Ala Cys Gly  Gly Ala Gly Thr Cys  Gly Ala Cys
    1580                 1585                 1590

Cys Ala  Cys Thr Gly Gly Gly  Ala Thr Gly Cys Thr  Thr Ala Cys
    1595                 1600                 1605

Ala Ala  Gly Gly Gly Thr Gly  Ala Gly Ala Gly Ala  Gly Thr Cys
    1610                 1615                 1620
```

-continued

```
Gly Thr  Thr Cys Thr Cys Thr  Gly Gly Gly Ala Cys  Gly Ala Thr
    1625                 1630                 1635

Thr Ala  Thr Gly Gly Gly Ala  Thr Gly Ala Gly Thr  Ala Ala Cys
    1640                 1645                 1650

Cys Cys  Cys Gly Thr Cys Cys  Ala Thr Gly Ala Thr  Gly Cys Cys
    1655                 1660                 1665

Cys Thr  Ala Ala Gly Ala Cys  Thr Cys Cys Ala Ala  Gly Ala Ala
    1670                 1675                 1680

Cys Thr  Thr Gly Cys Thr Gly  Ala Cys Ala Cys Cys  Thr Gly Cys
    1685                 1690                 1695

Cys Cys  Thr Thr Thr Gly Ala  Cys Cys Cys Thr Ala  Ala Ala Cys
    1700                 1705                 1710

Thr Gly  Thr Gly Ala Cys Ala  Gly Ala Ala Thr Thr  Gly Ala Gly
    1715                 1720                 1725

Ala Ala  Cys Ala Ala Gly Gly  Gly Cys Ala Ala Gly  Gly Thr Cys
    1730                 1735                 1740

Thr Thr  Thr Gly Ala Cys Ala  Gly Thr Gly Ala Thr  Gly Cys Cys
    1745                 1750                 1755

Ala Thr  Ala Ala Thr Cys Ala  Thr Cys Ala Cys Ala  Ala Cys Cys
    1760                 1765                 1770

Ala Ala  Cys Cys Thr Gly Gly  Cys Thr Ala Ala Cys  Cys Cys Ala
    1775                 1780                 1785

Gly Cys  Thr Cys Cys Ala Cys  Thr Thr Gly Ala Thr  Thr Ala Thr
    1790                 1795                 1800

Gly Thr  Cys Ala Ala Cys Thr  Thr Thr Gly Ala Ala  Gly Cys Thr
    1805                 1810                 1815

Thr Gly  Cys Thr Cys Cys Ala  Gly Gly Cys Gly Cys  Ala Thr Thr
    1820                 1825                 1830

Gly Ala  Cys Thr Thr Cys Cys  Thr Thr Gly Thr Gly  Thr Ala Thr
    1835                 1840                 1845

Gly Cys  Cys Gly Ala Thr Gly  Cys Ala Cys Cys Thr  Gly Ala Cys
    1850                 1855                 1860

Gly Thr  Thr Gly Ala Gly Ala  Ala Ala Gly Cys Gly  Ala Ala Gly
    1865                 1870                 1875

Cys Gly  Cys Gly Ala Cys Thr  Thr Cys Cys Cys Gly  Gly Gly Ala
    1880                 1885                 1890

Cys Ala  Ala Cys Cys Thr Gly  Ala Cys Ala Thr Gly  Thr Gly Gly
    1895                 1900                 1905

Ala Ala  Gly Ala Gly Cys Gly  Cys Thr Thr Ala Thr  Ala Gly Thr
    1910                 1915                 1920

Cys Cys  Cys Gly Ala Cys Thr  Thr Cys Thr Cys Ala  Cys Ala Cys
    1925                 1930                 1935

Ala Thr  Cys Ala Ala Gly Cys  Thr Ala Ala Thr Gly  Cys Thr Gly
    1940                 1945                 1950

Gly Cys  Thr Cys Cys Cys Cys  Ala Gly Gly Gly Thr  Gly Gly Thr
    1955                 1960                 1965

Thr Thr  Thr Gly Ala Cys Ala  Ala Ala Ala Ala Thr  Gly Gly Cys
    1970                 1975                 1980

Ala Ala  Cys Ala Cys Cys Cys  Cys Ala Cys Ala Cys  Gly Gly Gly
    1985                 1990                 1995

Ala Ala  Ala Gly Gly Thr Gly  Thr Cys Ala Thr Gly  Ala Ala Gly
    2000                 2005                 2010
```

-continued

```
Ala Cys  Cys Cys Thr Cys Ala  Cys Ala Ala Cys Ala  Gly Gly Cys
    2015                 2020                 2025

Thr Cys  Cys Cys Thr Cys Ala  Thr Thr Gly Cys Cys  Cys Gly Thr
    2030                 2035                 2040

Gly Cys  Thr Thr Cys Ala Gly  Gly Gly Cys Thr Cys  Cys Thr Cys
    2045                 2050                 2055

Cys Ala  Thr Gly Ala Ala Cys  Gly Ala Thr Thr Gly  Gly Ala Thr
    2060                 2065                 2070

Gly Ala  Ala Thr Thr Cys Gly  Ala Ala Cys Thr Ala  Cys Ala Ala
    2075                 2080                 2085

Gly Gly  Ala Cys Cys Cys Ala  Ala Cys Cys Thr Cys  Ala Cys Ala
    2090                 2095                 2100

Ala Cys  Thr Thr Thr Cys Ala  Ala Cys Thr Thr Thr  Gly Ala Cys
    2105                 2110                 2115

Cys Gly  Thr Ala Ala Thr Ala  Ala Ala Ala Thr Ala  Cys Ala Gly
    2120                 2125                 2130

Gly Cys  Thr Thr Thr Thr Ala  Gly Gly Cys Ala Gly  Cys Thr Thr
    2135                 2140                 2145

Gly Cys  Cys Gly Cys Thr Gly  Ala Ala Ala Ala Cys  Ala Ala Ala
    2150                 2155                 2160

Thr Ala  Thr Gly Gly Cys Cys  Thr Gly Gly Thr Gly  Gly Ala Cys
    2165                 2170                 2175

Ala Cys  Ala Ala Thr Gly Ala  Gly Ala Gly Thr Gly  Gly Gly Thr
    2180                 2185                 2190

Gly Gly  Ala Cys Ala Ala Cys  Thr Cys Ala Ala Gly  Gly Gly Thr
    2195                 2200                 2205

Gly Thr  Cys Ala Gly Ala Ala  Cys Thr Ala Thr Ala  Cys Cys Ala
    2210                 2215                 2220

Gly Ala  Ala Cys Thr Cys Ala  Ala Gly Cys Ala Gly  Gly Cys Cys
    2225                 2230                 2235

Cys Thr  Cys Ala Ala Gly Ala  Ala Cys Ala Thr Ala  Thr Thr Ala
    2240                 2245                 2250

Ala Thr  Cys Ala Ala Ala Ala  Gly Gly Thr Gly Cys  Cys Ala Gly
    2255                 2260                 2265

Ala Thr  Ala Gly Thr Gly Thr  Ala Thr Gly Gly Thr  Gly Gly Cys
    2270                 2275                 2280

Ala Gly  Cys Ala Cys Cys Thr  Ala Thr Ala Cys Ala  Cys Thr Thr
    2285                 2290                 2295

Gly Ala  Ala Thr Cys Thr Gly  Ala Thr Gly Gly Cys  Ala Ala Ala
    2300                 2305                 2310

Gly Gly  Gly Ala Ala Thr Gly  Thr Gly Ala Ala Ala  Gly Thr Gly
    2315                 2320                 2325

Gly Ala  Ala Ala Ala Ala Gly  Thr Gly Cys Ala Ala  Ala Ala Thr
    2330                 2335                 2340

Ala Cys  Cys Ala Ala Cys Ala  Thr Cys Cys Ala Ala  Ala Thr Cys
    2345                 2350                 2355

Ala Ala  Cys Ala Ala Cys Gly  Ala Gly Cys Thr Ala  Gly Cys Thr
    2360                 2365                 2370

Gly Gly  Thr Gly Cys Thr Thr  Thr Ala Cys Ala Cys  Cys Ala Cys
    2375                 2380                 2385

Cys Thr  Cys Cys Gly Ala Thr  Gly Cys Gly Cys Thr  Ala Gly Gly
    2390                 2395                 2400
```

-continued

```
Ala Thr  Cys Ala Gly Gly Thr  Ala Cys Thr Ala Thr  Gly Thr Thr
    2405                 2410                 2415

Ala Ala  Ala Thr Gly Thr Gly  Thr Thr Cys Ala Gly  Gly Ala Gly
    2420                 2425                 2430

Gly Cys  Thr Cys Thr Ala Thr  Ala Thr Thr Cys Cys  Ala Thr Cys
    2435                 2440                 2445

Ala Thr  Cys Cys Ala Ala Ala  Thr Thr Gly Cys Thr  Gly Gly Gly
    2450                 2455                 2460

Gly Cys  Cys Gly Cys Gly Thr  Thr Thr Gly Thr Ala  Ala Cys Cys
    2465                 2470                 2475

Ala Cys  Gly Cys Gly Cys Ala  Thr Thr Gly Thr Gly  Ala Ala Gly
    2480                 2485                 2490

Cys Gly  Cys Ala Thr Gly Ala  Ala Cys Ala Thr Ala  Cys Ala Ala
    2495                 2500                 2505

Ala Ala  Cys Thr Thr Gly Thr  Gly Gly Thr Cys Ala  Ala Gly Gly
    2510                 2515                 2520

Cys Cys  Thr Cys Cys Ala Gly  Thr Ala Gly Gly Ala  Gly Ala Thr
    2525                 2530                 2535

Gly Cys  Gly Gly Ala Gly Gly  Ala Gly Gly Thr Cys  Ala Cys Thr
    2540                 2545                 2550

Ala Gly  Cys Cys Ala Gly Gly  Ala Thr Gly Gly Thr  Thr Gly Cys
    2555                 2560                 2565

Cys Cys  Ala Ala Ala Gly Cys  Cys Cys Ala Ala Ala  Gly Ala Thr
    2570                 2575                 2580

Gly Ala  Thr Gly Ala Gly Gly  Ala Gly Thr Thr Cys  Gly Thr Cys
    2585                 2590                 2595

Ala Thr  Cys Thr Cys Gly Thr  Cys Thr Ala Gly Thr  Gly Ala Cys
    2600                 2605                 2610

Ala Thr  Cys Ala Cys Gly Cys  Cys Thr Gly Ala Ala  Gly Gly Cys
    2615                 2620                 2625

Ala Ala  Gly Ala Ala Ala Gly  Gly Ala Ala Ala Gly  Ala Ala Cys
    2630                 2635                 2640

Ala Ala  Gly Ala Cys Thr Gly  Gly Cys Cys Gly Cys  Gly Gly Cys
    2645                 2650                 2655

Ala Ala  Gly Ala Ala Ala Cys  Ala Cys Ala Cys Ala  Gly Cys Cys
    2660                 2665                 2670

Thr Thr  Cys Thr Cys Gly Ala  Gly Cys Ala Ala Gly  Gly Gly Thr
    2675                 2680                 2685

Cys Thr  Cys Ala Gly Thr Gly  Ala Thr Gly Ala Gly  Gly Ala Gly
    2690                 2695                 2700

Thr Ala  Cys Gly Ala Thr Gly  Ala Gly Thr Ala Cys  Ala Ala Ala
    2705                 2710                 2715

Ala Gly  Ala Ala Thr Cys Ala  Gly Gly Gly Ala Ala  Gly Ala Ala
    2720                 2725                 2730

Ala Gly  Gly Ala Ala Thr Gly  Gly Thr Ala Ala Gly  Thr Ala Cys
    2735                 2740                 2745

Thr Cys  Cys Ala Thr Ala Gly  Ala Ala Gly Ala Ala  Thr Ala Cys
    2750                 2755                 2760

Cys Thr  Thr Cys Ala Gly Gly  Ala Cys Ala Gly Ala  Gly Ala Cys
    2765                 2770                 2775

Ala Ala  Gly Thr Ala Thr Thr  Ala Thr Gly Ala Gly  Gly Ala Ala
    2780                 2785                 2790
```

-continued

```
Gly Thr  Gly Gly Cys Cys Ala  Thr Ala Gly Cys Cys  Ala Gly Gly
    2795                 2800                 2805

Gly Cys  Ala Ala Cys Thr Gly  Ala Gly Gly Ala Ala  Gly Ala Cys
    2810                 2815                 2820

Thr Thr  Cys Thr Gly Thr Gly  Ala Gly Gly Ala Ala  Gly Ala Ala
    2825                 2830                 2835

Gly Ala  Ala Gly Cys Cys Ala  Ala Gly Ala Thr Cys  Cys Gly Ala
    2840                 2845                 2850

Cys Ala  Gly Ala Gly Gly Ala  Thr Ala Thr Thr Thr  Ala Gly Gly
    2855                 2860                 2865

Cys Cys  Ala Ala Cys Gly Ala  Gly Gly Ala Ala Gly  Cys Ala Ala
    2870                 2875                 2880

Cys Gly  Cys Ala Ala Gly Gly  Ala Gly Gly Ala Gly  Ala Gly Gly
    2885                 2890                 2895

Gly Cys  Thr Thr Cys Cys Cys  Thr Thr Gly Gly Cys  Cys Thr Thr
    2900                 2905                 2910

Gly Thr  Cys Ala Cys Thr Gly  Gly Cys Thr Cys Ala  Gly Ala Gly
    2915                 2920                 2925

Ala Thr  Cys Ala Gly Ala Ala  Ala Gly Ala Gly Ala  Ala Ala Cys
    2930                 2935                 2940

Cys Cys  Ala Gly Ala Cys Gly  Ala Cys Thr Thr Cys  Ala Ala Ala
    2945                 2950                 2955

Cys Cys  Thr Ala Ala Ala Gly  Gly Ala Ala Ala Gly  Cys Thr Gly
    2960                 2965                 2970

Thr Gly  Gly Gly Cys Thr Gly  Ala Thr Gly Ala Thr  Gly Ala Ala
    2975                 2980                 2985

Ala Gly  Gly Gly Thr Cys Gly  Thr Thr Gly Ala Cys  Thr Ala Thr
    2990                 2995                 3000

Ala Ala  Thr Gly Ala Gly Ala  Ala Ala Cys Thr Cys  Ala Gly Thr
    3005                 3010                 3015

Thr Thr  Thr Gly Ala Gly Gly  Cys Cys Cys Cys Cys  Cys Cys Gly
    3020                 3025                 3030

Ala Gly  Cys Ala Thr Cys Thr  Gly Gly Thr Cys Ala  Ala Gly Gly
    3035                 3040                 3045

Ala Thr  Ala Gly Thr Cys Ala  Ala Cys Thr Thr Thr  Gly Gly Gly
    3050                 3055                 3060

Thr Cys  Ala Gly Gly Ala Thr  Gly Gly Gly Gly Gly  Thr Thr Cys
    3065                 3070                 3075

Thr Gly  Gly Gly Thr Gly Thr  Cys Cys Cys Cys Thr  Ala Gly Cys
    3080                 3085                 3090

Cys Thr  Gly Thr Thr Thr Ala  Thr Thr Ala Cys Ala  Thr Cys Ala
    3095                 3100                 3105

Ala Cys  Cys Cys Ala Thr Gly  Thr Thr Ala Thr Ala  Cys Cys Cys
    3110                 3115                 3120

Cys Ala  Ala Gly Gly Cys Ala  Cys Thr Cys Ala Gly  Gly Ala Ala
    3125                 3130                 3135

Thr Thr  Cys Thr Thr Thr Gly  Gly Thr Gly Thr Ala  Cys Cys Cys
    3140                 3145                 3150

Ala Thr  Cys Ala Ala Gly Cys  Ala Gly Ala Thr Thr  Cys Ala Gly
    3155                 3160                 3165

Ala Thr  Thr Cys Ala Cys Ala  Ala Ala Thr Cys Ala  Gly Gly Gly
    3170                 3175                 3180
```

-continued

```
Gly Ala  Gly Thr Thr Cys Thr  Gly Cys Cys Gly Cys  Cys Thr Gly
    3185                3190                3195

Ala Gly  Ala Thr Thr Cys Cys  Cys Thr Ala Ala Ala  Thr Cys Ala
    3200                3205                3210

Ala Thr  Cys Ala Gly Ala Ala  Cys Thr Gly Cys Thr  Gly Thr Ala
    3215                3220                3225

Ala Cys  Ala Gly Gly Cys Ala  Thr Gly Ala Thr Cys  Cys Thr Ala
    3230                3235                3240

Gly Ala  Ala Gly Ala Gly Gly  Gly Gly Gly Cys Cys  Cys Cys Ala
    3245                3250                3255

Gly Ala  Ala Gly Gly Ala Ala  Cys Cys Gly Thr Gly  Gly Thr Cys
    3260                3265                3270

Thr Cys  Ala Cys Thr Ala Cys  Thr Cys Ala Thr Cys  Ala Ala Gly
    3275                3280                3285

Ala Gly  Ala Cys Cys Ala Ala  Cys Cys Gly Gly Thr  Gly Ala Gly
    3290                3295                3300

Cys Thr  Cys Ala Thr Gly Cys  Cys Cys Cys Thr Gly  Gly Cys Ala
    3305                3310                3315

Gly Cys  Cys Ala Gly Ala Ala  Thr Gly Gly Gly Cys  Ala Cys Cys
    3320                3325                3330

Cys Ala  Thr Gly Cys Gly Ala  Cys Thr Ala Thr Gly  Ala Ala Ala
    3335                3340                3345

Ala Thr  Cys Cys Ala Ala Gly  Gly Thr Cys Gly Cys  Ala Cys Gly
    3350                3355                3360

Gly Thr  Thr Gly Gly Ala Gly  Gly Thr Cys Ala Gly  Ala Thr Gly
    3365                3370                3375

Gly Gly  Thr Ala Thr Gly Thr  Thr Gly Cys Thr Ala  Ala Cys Ala
    3380                3385                3390

Gly Gly  Gly Thr Cys Cys Ala  Ala Thr Gly Cys Thr  Ala Ala Ala
    3395                3400                3405

Ala Gly  Cys Ala Thr Gly Gly  Ala Thr Thr Thr Gly  Gly Gly Cys
    3410                3415                3420

Ala Cys  Gly Ala Cys Ala Cys  Cys Thr Gly Gly Thr  Gly Ala Cys
    3425                3430                3435

Thr Gly  Thr Gly Gly Cys Thr  Gly Cys Cys Cys Cys  Thr Ala Thr
    3440                3445                3450

Ala Thr  Thr Thr Ala Thr Ala  Ala Gly Ala Gly Ala  Gly Gly Cys
    3455                3460                3465

Ala Ala  Thr Gly Ala Cys Thr  Ala Cys Gly Thr Gly  Gly Thr Cys
    3470                3475                3480

Ala Thr  Cys Gly Gly Cys Gly  Thr Gly Cys Ala Cys  Ala Cys Ala
    3485                3490                3495

Gly Cys  Cys Gly Cys Thr Gly  Cys Thr Cys Gly Cys  Gly Gly Ala
    3500                3505                3510

Gly Gly  Thr Ala Ala Cys Ala  Cys Thr Gly Thr Cys  Ala Thr Cys
    3515                3520                3525

Thr Gly  Thr Gly Cys Ala Ala  Cys Cys Cys Ala Gly  Gly Gly Cys
    3530                3535                3540

Ala Gly  Thr Gly Ala Ala Gly  Gly Thr Gly Ala Gly  Gly Cys Cys
    3545                3550                3555

Ala Cys  Gly Cys Thr Cys Gly  Ala Ala Gly Gly Cys  Gly Gly Thr
    3560                3565                3570
```

-continued

```
Gly Ala  Thr Ala Ala Cys Ala  Ala Ala Gly Gly Cys  Ala Cys Cys
    3575                 3580                 3585

Thr Ala  Cys Thr Gly Thr Gly  Gly Ala Gly Cys Thr  Cys Cys Ala
    3590                 3595                 3600

Ala Thr  Ala Cys Thr Ala Gly  Gly Cys Cys Cys Thr  Gly Gly Thr
    3605                 3610                 3615

Ala Ala  Cys Gly Cys Thr Cys  Cys Cys Ala Ala Gly  Cys Thr Cys
    3620                 3625                 3630

Ala Gly  Cys Ala Cys Cys Ala  Ala Gly Ala Cys Thr  Ala Ala Ala
    3635                 3640                 3645

Thr Thr  Cys Thr Gly Gly Ala  Gly Gly Thr Cys Cys  Thr Cys Cys
    3650                 3655                 3660

Ala Cys  Ala Gly Thr Gly Cys  Cys Ala Cys Thr Cys  Cys Cys Ala
    3665                 3670                 3675

Cys Cys  Cys Gly Gly Gly Ala  Cys Cys Thr Ala Thr  Gly Ala Ala
    3680                 3685                 3690

Cys Cys  Ala Gly Cys Thr Thr  Ala Cys Thr Thr Ala  Gly Gly Thr
    3695                 3700                 3705

Gly Gly  Cys Ala Ala Gly Gly  Ala Cys Cys Cys Cys  Ala Gly Gly
    3710                 3715                 3720

Gly Thr  Gly Ala Ala Gly Gly  Gly Thr Gly Gly Ala  Cys Cys Thr
    3725                 3730                 3735

Thr Cys  Ala Cys Thr Ala Cys  Ala Ala Cys Ala Ala  Gly Thr Cys
    3740                 3745                 3750

Ala Thr  Gly Ala Gly Ala Gly  Ala Cys Cys Ala Gly  Cys Thr Ala
    3755                 3760                 3765

Ala Ala  Ala Cys Cys Ala Thr  Thr Cys Ala Cys Thr  Gly Ala Gly
    3770                 3775                 3780

Cys Cys  Thr Ala Gly Gly Gly  Gly Cys Ala Ala Ala  Cys Cys Ala
    3785                 3790                 3795

Cys Cys  Cys Ala Ala Gly Cys  Cys Ala Ala Gly Thr  Gly Thr Gly
    3800                 3805                 3810

Cys Thr  Gly Gly Ala Ala Gly  Cys Thr Gly Cys Cys  Ala Ala Gly
    3815                 3820                 3825

Ala Ala  Gly Ala Cys Cys Ala  Thr Thr Ala Thr Cys  Ala Ala Thr
    3830                 3835                 3840

Gly Thr  Gly Thr Thr Gly Gly  Ala Gly Cys Ala Ala  Ala Cys Ala
    3845                 3850                 3855

Ala Thr  Ala Gly Ala Thr Cys  Cys Cys Cys Cys Cys  Cys Ala Ala
    3860                 3865                 3870

Ala Ala  Ala Thr Gly Gly Thr  Cys Ala Thr Thr Thr  Thr Cys Ala
    3875                 3880                 3885

Cys Ala  Ala Gly Cys Ala Thr  Gly Thr Gly Cys Gly  Thr Cys Gly
    3890                 3895                 3900

Cys Thr  Thr Gly Ala Thr Ala  Ala Ala Ala Cys Cys  Ala Cys Cys
    3905                 3910                 3915

Thr Cys  Cys Ala Gly Cys Gly  Gly Cys Cys Ala Cys  Cys Cys Cys
    3920                 3925                 3930

Cys Ala  Cys Cys Ala Cys Ala  Thr Ala Cys Gly Gly  Ala Ala Gly
    3935                 3940                 3945

Ala Ala  Cys Gly Ala Thr Thr  Gly Cys Thr Gly Gly  Ala Ala Thr
    3950                 3955                 3960
```

-continued

```
Gly Gly  Gly Gly Ala Gly Thr  Cys Thr Thr Thr Thr  Ala Cys Ala
    3965                 3970                 3975

Gly Gly  Ala Ala Ala Ala Thr  Thr Gly Gly Cys Ala  Gly Ala Thr
    3980                 3985                 3990

Cys Ala  Ala Gly Cys Ala Thr  Cys Ala Ala Ala Ala  Gly Cys Thr
    3995                 4000                 4005

Ala Ala  Cys Cys Thr Ala Ala  Thr Gly Thr Ala Thr  Gly Ala Gly
    4010                 4015                 4020

Gly Ala  Ala Gly Gly Ala Ala  Ala Gly Ala Ala Cys  Ala Thr Gly
    4025                 4030                 4035

Ala Cys  Cys Cys Cys Ala Gly  Thr Cys Thr Ala Cys  Ala Cys Ala
    4040                 4045                 4050

Gly Gly  Gly Gly Cys Cys Cys  Thr Cys Ala Ala Gly  Gly Ala Thr
    4055                 4060                 4065

Gly Ala  Gly Cys Thr Gly Gly  Thr Cys Ala Ala Gly  Ala Cys Thr
    4070                 4075                 4080

Gly Ala  Cys Ala Ala Gly Ala  Thr Cys Thr Ala Thr  Gly Gly Gly
    4085                 4090                 4095

Cys Ala  Gly Ala Thr Cys Ala  Ala Gly Ala Ala Ala  Ala Gly Gly
    4100                 4105                 4110

Cys Thr  Thr Cys Thr Thr Thr  Gly Gly Gly Gly Cys  Thr Cys Thr
    4115                 4120                 4125

Gly Ala  Cys Thr Thr Gly Gly  Cys Ala Ala Cys Ala  Ala Thr Gly
    4130                 4135                 4140

Ala Thr  Cys Cys Gly Thr Thr  Gly Thr Gly Cys Gly  Cys Gly Gly
    4145                 4150                 4155

Gly Cys  Gly Thr Thr Thr Gly  Gly Ala Gly Gly Gly  Thr Thr Ala
    4160                 4165                 4170

Ala Thr  Gly Gly Ala Thr Gly  Ala Gly Cys Thr Cys  Ala Ala Gly
    4175                 4180                 4185

Gly Cys  Cys Cys Ala Thr Thr  Gly Cys Gly Thr Ala  Ala Cys Ala
    4190                 4195                 4200

Cys Thr  Cys Cys Cys Thr Gly  Thr Cys Ala Gly Gly  Gly Thr Thr
    4205                 4210                 4215

Gly Gly  Gly Ala Thr Gly Ala  Ala Cys Ala Thr Gly  Ala Ala Thr
    4220                 4225                 4230

Gly Ala  Gly Gly Ala Thr Gly  Gly Ala Cys Cys Cys  Ala Thr Ala
    4235                 4240                 4245

Ala Thr  Thr Thr Thr Thr Gly  Ala Ala Ala Ala Gly  Cys Ala Cys
    4250                 4255                 4260

Thr Cys  Cys Ala Gly Gly Thr  Thr Cys Thr Cys Ala  Thr Ala Cys
    4265                 4270                 4275

Cys Ala  Cys Thr Ala Thr Gly  Ala Thr Gly Cys Ala  Gly Ala Thr
    4280                 4285                 4290

Thr Ala  Cys Thr Cys Ala Cys  Gly Cys Thr Gly Gly  Gly Ala Cys
    4295                 4300                 4305

Thr Cys  Ala Ala Cys Cys Cys  Ala Ala Cys Ala Gly  Ala Gly Gly
    4310                 4315                 4320

Gly Cys  Ala Gly Thr Gly Cys  Thr Ala Gly Cys Thr  Gly Cys Ala
    4325                 4330                 4335

Gly Cys  Cys Thr Thr Gly Gly  Ala Ala Ala Thr Cys  Ala Thr Gly
    4340                 4345                 4350
```

-continued

```
Gly Thr  Ala Ala Ala Ala Thr  Thr Cys Thr Cys Ala  Cys Cys Ala
    4355                 4360                 4365

Gly Ala  Ala Cys Cys Ala Cys  Ala Thr Thr Thr Gly  Gly Cys Cys
    4370                 4375                 4380

Cys Ala  Ala Ala Thr Thr Gly  Thr Thr Gly Cys Ala  Gly Ala Gly
    4385                 4390                 4395

Gly Ala  Thr Cys Thr Cys Cys  Thr Ala Gly Cys Cys  Cys Cys Cys
    4400                 4405                 4410

Ala Gly  Thr Gly Thr Gly Ala  Thr Gly Gly Ala Thr  Gly Thr Ala
    4415                 4420                 4425

Gly Gly  Thr Gly Ala Thr Thr  Thr Cys Ala Ala Ala  Ala Thr Ala
    4430                 4435                 4440

Ala Cys  Ala Ala Thr Thr Ala  Ala Thr Gly Ala Gly  Gly Gly Ala
    4445                 4450                 4455

Cys Thr  Gly Cys Cys Cys Thr  Cys Gly Gly Gly Ala  Gly Thr Ala
    4460                 4465                 4470

Cys Cys  Cys Thr Gly Cys Ala  Cys Ala Thr Cys Ala  Cys Ala Gly
    4475                 4480                 4485

Thr Gly  Gly Ala Ala Thr Thr  Cys Cys Ala Thr Cys  Gly Cys Cys
    4490                 4495                 4500

Cys Ala  Cys Thr Gly Gly Cys  Thr Cys Cys Thr Cys  Ala Cys Ala
    4505                 4510                 4515

Cys Thr  Cys Thr Gly Cys Gly  Cys Ala Cys Thr Ala  Thr Cys Thr
    4520                 4525                 4530

Gly Ala  Ala Gly Thr Cys Ala  Cys Ala Ala Ala Cys  Cys Thr Gly
    4535                 4540                 4545

Gly Cys  Thr Cys Cys Thr Gly  Ala Cys Ala Thr Cys  Ala Thr Ala
    4550                 4555                 4560

Cys Ala  Ala Gly Cys Thr Ala  Ala Cys Thr Cys Cys  Thr Thr Gly
    4565                 4570                 4575

Thr Thr  Cys Thr Cys Thr Thr  Thr Cys Thr Ala Thr  Gly Gly Thr
    4580                 4585                 4590

Gly Ala  Thr Gly Ala Thr Gly  Ala Ala Ala Thr Cys  Gly Thr Ala
    4595                 4600                 4605

Ala Gly  Thr Ala Cys Thr Gly  Ala Cys Ala Thr Ala  Ala Ala Ala
    4610                 4615                 4620

Thr Thr  Ala Gly Ala Cys Cys  Cys Ala Gly Ala Gly  Ala Ala Ala
    4625                 4630                 4635

Cys Thr  Cys Ala Cys Ala Gly  Cys Ala Ala Ala Ala  Cys Thr Cys
    4640                 4645                 4650

Ala Ala  Ala Gly Ala Ala Thr  Ala Cys Gly Gly Ala  Cys Thr Cys
    4655                 4660                 4665

Ala Ala  Ala Cys Cys Ala Ala  Cys Cys Cys Gly Cys  Cys Cys Gly
    4670                 4675                 4680

Gly Ala  Cys Ala Ala Ala Ala  Cys Thr Gly Ala Ala  Gly Gly Ala
    4685                 4690                 4695

Cys Cys  Cys Cys Thr Gly Ala  Thr Cys Ala Thr Ala  Thr Cys Cys
    4700                 4705                 4710

Gly Ala  Gly Gly Ala Cys Thr  Thr Gly Ala Ala Thr  Gly Gly Thr
    4715                 4720                 4725

Thr Thr  Gly Ala Cys Cys Thr  Thr Thr Cys Thr Gly  Cys Gly Gly
    4730                 4735                 4740
```

-continued

```
Cys Gly Gly Ala Cys Cys Gly Thr Gly Ala Cys Cys Cys Gly Thr
    4745                 4750                 4755

Gly Ala Thr Cys Cys Ala Gly Cys Thr Gly Gly Gly Thr Gly Gly
    4760                 4765                 4770

Thr Thr Thr Gly Gly Cys Ala Ala Gly Thr Thr Gly Gly Ala Cys
    4775                 4780                 4785

Cys Ala Gly Ala Gly Thr Thr Cys Ala Ala Thr Thr Cys Thr Cys
    4790                 4795                 4800

Ala Gly Gly Cys Ala Gly Ala Thr Ala Thr Ala Cys Thr Gly Gly
    4805                 4810                 4815

Ala Cys Thr Ala Gly Gly Gly Gly Cys Cys Cys Cys Ala Ala Cys
    4820                 4825                 4830

Cys Ala Thr Gly Ala Gly Gly Ala Cys Cys Cys Gly Thr Cys Cys
    4835                 4840                 4845

Gly Ala Ala Ala Cys Ala Ala Thr Gly Ala Thr Ala Cys Cys Ala
    4850                 4855                 4860

Cys Ala Cys Thr Cys Cys Cys Ala Gly Ala Gly Gly Cys Cys Thr
    4865                 4870                 4875

Ala Thr Ala Cys Ala Gly Cys Thr Gly Ala Thr Gly Thr Cys Thr
    4880                 4885                 4890

Cys Thr Thr Thr Thr Gly Gly Gly Thr Gly Ala Ala Gly Cys Ala
    4895                 4900                 4905

Gly Cys Cys Thr Thr Gly Cys Ala Thr Gly Gly Thr Cys Cys Ala
    4910                 4915                 4920

Ala Cys Ala Thr Thr Thr Thr Ala Cys Ala Cys Cys Ala Ala Ala
    4925                 4930                 4935

Ala Thr Cys Ala Gly Thr Ala Ala Ala Cys Thr Gly Gly Thr Cys
    4940                 4945                 4950

Ala Thr Cys Ala Cys Ala Gly Ala Gly Cys Thr Gly Ala Ala Gly
    4955                 4960                 4965

Gly Ala Ala Gly Gly Thr Gly Gly Cys Ala Thr Gly Gly Ala Thr
    4970                 4975                 4980

Thr Thr Thr Thr Ala Cys Gly Thr Gly Cys Cys Cys Ala Gly Ala
    4985                 4990                 4995

Cys Ala Gly Gly Ala Ala Cys Cys Cys Ala Thr Gly Thr Thr Cys
    5000                 5005                 5010

Ala Gly Gly Thr Gly Gly Ala Thr Gly Ala Gly Ala Thr Thr Cys
    5015                 5020                 5025

Thr Cys Ala Gly Ala Thr Thr Thr Gly Ala Gly Cys Ala Cys Gly
    5030                 5035                 5040

Thr Gly Gly Gly Ala Gly Gly Gly Cys Gly Ala Thr Cys Gly Cys
    5045                 5050                 5055

Ala Ala Thr Cys Thr Gly Gly Cys Thr Cys Cys Cys Ala Gly Thr
    5060                 5065                 5070

Thr Thr Thr Gly Thr Gly Ala Ala Thr Gly Ala Ala Gly Ala Thr
    5075                 5080                 5085

Gly Gly Cys Gly Thr Cys Gly Ala Ala Thr Gly Ala
    5090                 5095                 5100
```